United States Patent
Reddy et al.

(10) Patent No.: US 8,227,431 B2
(45) Date of Patent: Jul. 24, 2012

(54) NUCLEOSIDE DERIVATIVES

(75) Inventors: Bandi Parthasaradhi Reddy, Andhra Pradesh (IN); Vedula Manohar Sharma, Andhra Pradesh (IN); Kura Rathnakar Reddy, Andhra Pradesh (IN); Musku Madhanmohan Reddy, Andhra Pradesh (IN); Jennepalli Sreenu, Andhra Pradesh (IN); Aryasomayajula Ratnakar, Andhra Pradesh (IN)

(73) Assignee: Hetero Drugs Limited (IN)

( * ) Notice: Subject to any disclaimer, the term of this patent is extended or adjusted under 35 U.S.C. 154(b) by 365 days.

(21) Appl. No.: 12/402,601

(22) Filed: Mar. 12, 2009

(65) Prior Publication Data

US 2009/0233879 A1    Sep. 17, 2009

(30) Foreign Application Priority Data

Mar. 17, 2008 (IN) .............................. 653/CHE/2008
Feb. 16, 2009 (IN) .............................. 333/CHE/2009

(51) Int. Cl.
*A01N 43/04* (2006.01)
*A61K 31/70* (2006.01)

(52) U.S. Cl. ................ 514/43; 514/42; 514/45; 514/49; 536/25.3; 536/26.1; 536/27.1; 536/27.11; 536/27.13; 536/28.1

(58) Field of Classification Search .................... None
See application file for complete search history.

(56) References Cited

U.S. PATENT DOCUMENTS

| | | |
|---|---|---|
| 7,192,936 B2 | 3/2007 | LaColla et al. |
| 7,547,704 B2 | 6/2009 | LaColla et al. |
| 2002/0147160 A1 | 10/2002 | Bhat et al. |
| 2004/0259934 A1 | 12/2004 | Olsen et al. |
| 2007/0042940 A1 | 2/2007 | LaColla et al. |
| 2007/0042990 A1 | 2/2007 | Gosselin et al. |
| 2009/0105186 A1 | 4/2009 | Matthes et al. |

FOREIGN PATENT DOCUMENTS

| | | |
|---|---|---|
| WO | 9816184 A2 | 4/1998 |
| WO | 9816186 A2 | 4/1998 |
| WO | 9914226 A2 | 3/1999 |
| WO | 0066604 A2 | 11/2000 |
| WO | 0190121 A2 | 11/2001 |
| WO | 02057287 A2 | 7/2002 |
| WO | 03039523 A2 | 3/2003 |
| WO | 03062256 A1 | 7/2003 |
| WO | 2004002999 A2 | 1/2004 |
| WO | 2004014312 A2 | 2/2004 |
| WO | 2004106356 A1 | 12/2004 |
| WO | 2005003147 A2 | 1/2005 |
| WO | 2005021568 A2 | 3/2005 |
| WO | 2006066080 A1 | 6/2006 |
| WO | 2008005542 A3 | 1/2008 |
| WO | 2009067409 A1 | 5/2009 |

OTHER PUBLICATIONS analogue. Dictionary.com. Dictionary.com Unabridged. Random House, Inc. http://dictionary.reference.com/browse/analogue (accessed: May 8, 2011).*
International Search Report for PCT/IB2009/000537 dated Mar. 16, 2009.
Tsutomu Moridawa, et al. Radical Cyclization to Fluorinated Double Bonds: 5-Exo Ring Closure of Bromocetals Derived From Fluoroallyl Alcohols, Tetrahedrom Letters. vol. 28, No. 6, pp. 671-674, 1987.
Jeremy L. Clark, et al. Synthesis and Antiviral Activity of 2-Deoxy-2-Fluoro-2-C-Methyl Purine Nucleosides as Inhibitors of Hepatitis C Virus RNA Replication, Bioorganic & Medicinal Chemistry Letters 16 (2006) 1712-1715.
Nour Lahmar, et al. A Convenient Synthesis of y-Functionalized Cyclopentenones, Beilstein Journal of Organic Chemistry 2005, 1, No. 11.
Eugene V. Babaeu, et al. Efficient Synthesis of 5-Substituted 2-Aryl-6-Cyanoindolizines Via Nucleophilic Substitution Reactions, Beilstein Journal of Organic Chemistry 2005, 1, No. 9.

* cited by examiner

*Primary Examiner* — Patrick Lewis
(74) *Attorney, Agent, or Firm* — Caesar, Rivise, Bernstein, Cohen & Pokotilow, Ltd.

(57) ABSTRACT

The present patent application relates to the novel nucleoside derivatives and novel intermediates, which are useful to antiviral, anti tumor and immunomodulatory activity, method of treating diseases, conditions and/or disorders modulated by viral infections with them, and processes for preparing them.

18 Claims, No Drawings

NUCLEOSIDE DERIVATIVES

This application claims the benefit of Indian Provisional Patent Application Nos. 653/CHE/2008, filed Mar. 17, 2008 and 333/CHE/2009 filed Feb. 16, 2009, all of which are incorporated herein by reference in their entirety.

FIELD OF THE INVENTION

The present patent application relates to the novel nucleoside derivatives and novel intermediates, which are useful to antiviral, anti tumor and immunomodulatory activity.

BACKGROUND OF THE INVENTION

Infectious viral diseases are recognized as an important medical problem. Progress against infectious viral disease requires the development of drugs with selective anti viral activity while remaining benign to normal cell lines. Number of antiviral agents, anti tumor, and immunomodulatory compounds available in the market and or in discovery are nucleoside analogs. In general these compounds are structural analogs of the naturally occurring nucleosides. Structural modification in either the purine or pyrimidine base nucleus and/or the sugar component results in a synthetically modified nucleoside derivative which, when for example incorporated into a viral nucleic acid forming process, acts to disrupt further synthesis of viral nucleic acid. Effectiveness of these antiviral agents depends on selective conversion by viral enzymes, but not by host enzymes, to the corresponding nucleotide analog which is then converted to the triphosphate and incorporation into viral nucleic acid occurs. A problem with this antiviral strategy has been the emergence of certain viral strains whose enzymes poorly promote phosphorylation of nucleoside analogs. To circumvent this problem, there is a need to make newer analogs with different structural variants of both sugar moiety and base moiety of nucleosides. The success of various synthetic nucleosides in inhibiting the replication of virus in-vitro and in-vivo has led a number of researchers to design and test nucleosides with novel modified sugar moieties.

Recently several publications were appeared in the literature on C-2 substituted nucleosides. For example, a paper published in Journal of medicinal chemistry, 48 (17), 5504-5508:2005 discloses nucleoside compounds with novel C-2 substituted 5-carbon sugar component (S-I)

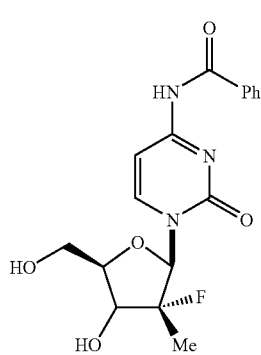

(S-I)

Other patent publications, PCT Int. Appl. No.'s, 2007075876, 5 Jul. 2007 and 2007065829, 14 Jun. 2007 disclose process for preparing a synthetic intermediate for preparation of branched nucleoside compounds (S-II & S-III).

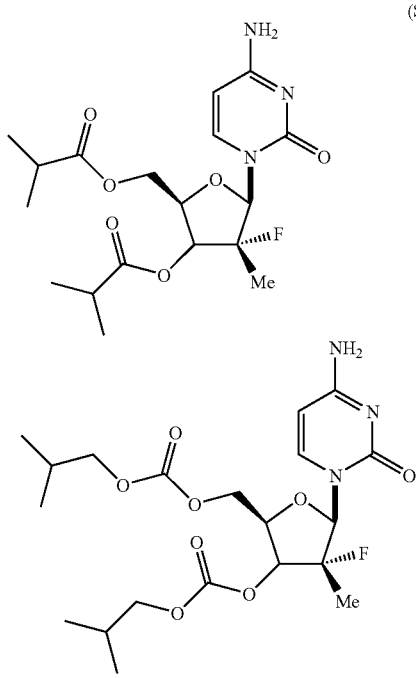

(S-II & S-III)

Other publications appeared in Tetrahedron Letters, 28(6), 671-4; 1987, Journal of Fluorine Chemistry, 35(2), 287-94; 1987, Beilstein Journal of Organic chemistry 1 (October) 2005, disclosed 2-halo, 2-C substituted pentose sugars Novel nucleosides for example (S-IV) was published in Journal of carbohydrate chemistry, 25(6), 461-470:2006

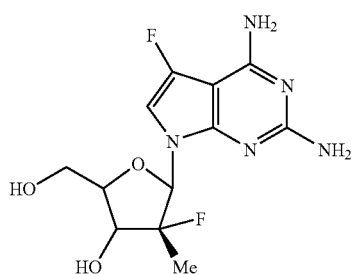

(S-IV)

Synthesis of purine nucleosides with 2-fluoro-2-methyl pentose derivatives (for example,

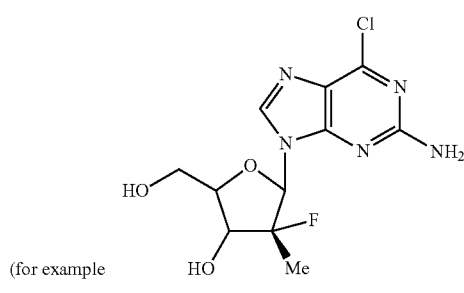

(for example    )

was published in *Bioorganic & Medicinal Chemistry Letters*, 16, (6), 1712-1715, 2006, Faming Zhuanli Shenquing Gongkai Shuomingshu, 1712409, 28 Dec. 2005 disclosed following type of compounds

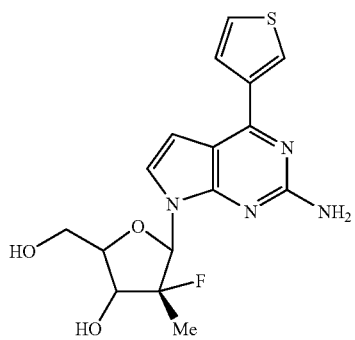

(S-V)

It is thus believed antivirals may be relevant with respect to, for example, HIV, HCV, and HBV, AIDS, and inflammatory disease, respiratory disorders (including adult respiratory distress syndrome (ARDS), bronchitis, chronic bronchitis, chronic obstructive pulmonary disease, cystic fibrosis, asthma, emphysema, rhinitis, chronic sinusitis and other bacterial infections associated with viral diseases. PCT Publications Nos. WO 01/07646, WO 01/65937, WO 03/37908, WO 98/46238, WO 95/02071, WO 2005/021568, WO 2005/009418, WO 2005/034971, WO 06/110656, WO 06/027628, WO 05/026114 and WO 08/063600; U.S. patent application/patent Nos. 4,598,095, US 2002/0068757, US 2005/0124623 and US 2007/0225249; EP patent application/patent Nos. EP 0989862 and EP 0724650 disclose antivirals for treatment of various diseases mediated by viral infections.

There are certain structural classes of nucleoside compounds that were explored intensively for their therapeutic activities. For example, the patent publications WO 2000/066604 describes L-ribo-Locked Nucleic Acids Analog Duplexes; WO 98/16184 and WO 98/16186 are describe purine L-nucleosides and monocyclic L-nucleosides respectively; WO 2008/005542 describes antiviral phosphinate compounds; WO 99/14226 and WO 03/039523 are describe oligonucleotide analogues; WO 03/062256 describes adenosine analogs; WO 04/014312 describes short oligonucleotides; WO 04/080466 describes cytidine analogs; US 2004/0259934 describes coronaviridae-nucleoside compounds; and WO 04/106356 describes functionalized nucleotide derivatives.

Given the fact of the world wide epidemic level of viral diseases, there is a strong need for new effective drugs for treatment of diseases, conditions and/or disorders mediated by viral infections.

SUMMARY OF THE INVENTION

The present patent application relates to compounds of the formula (I):

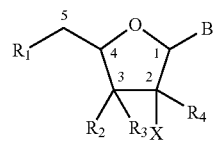

I wherein,
B can be Nitrogen heterocycle of from C3 to C15, such as optionally substituted purine, pyrimidine, pyridine, pyrrole, indole, imidazole, pyrazole, quinazoline, pyridizine, pyrezine, cinnoline, phthalazin, quinoxaline, xanthine, hypoxanthine, adenine, guanine, cytosine, uracil, thymine, pteridine, 5-azacytidine, 5-azauracil, triazolopyridine, imidazolopyridine, imidazolotriazine, pyrrolopyrimidine, pyrazolopyrimidine; the heterocycle may be bound to the sugar moiety in the nucleoside through any available atom including ring nitrogen or ring carbon atom;

X can be halogen;

$R_4$ can be alkyl group;

$R_2$ and $R_3$ are independently can be selected from OH, alkyl, alkenyl, halogen, alkynyl, cycloalkyl, $N_3$, $CF_3$, $NH_2$, RCONHCH(Ra)C(O)O, $NH_2CH(R^a)C(O)O$ (wherein $R^a$ can be H, alkyl or benezyl) or CN; $R_2$ and $R_3$ can be together form oxo (=O) group;

$R_1$ can be H, OH, —{P(O)(OH)O-}nR, alkyl, hydrogen, acyl, aryl, alkyl carbonyloxy, aryl carbonyloxy, silyl, RCONHCH(Ra)C(O)O, $NH_2CH(R^a)C(O)O$ (wherein $R^a$ can be H, alkyl or benezyl), heterocycloalkyl, or sulfonyl;

R can be alkyl, hydrogen, acyl, aryl, alkyl carbonyloxy, aryl carbonyloxy, or heterocycloalkyl;

$R_1$, $R_2$, $R_3$, $R_4$, and R are independently can be further substituted wherever appropriate by a group like halogen, alkyl, alkenyl, alkynyl, aryl, alkylaryl, aralkyl, cycloalkyl, heterocyclyl, heterocycloakyl, hydroxy, amino, cyano, azido, carbonyl, oxycarbonyl, sulfonyl, sulfonyloxy, or carbonyloxy.

Pharmaceutically acceptable salts of the compounds of the formula (I) are also contemplated. Likewise, pharmaceutically acceptable solvates, including hydrates, of the compounds of the formula (I) are contemplated.

It should be understood that the formula (I) structurally encompasses all stereoisomers, including enatiomers and diastereomers, which may be contemplated from the chemical structure of the genus described herein.

Also contemplated are prodrugs of the compounds of the formula (I), including ester prodrugs.

According to one embodiment, there is provided a compound of formula (I), wherein $R_1$ is —OH, —OBz, butanoyloxy, pentanoyloxy, (CH3)3COONHCH(CH3)C(O)O, and $NH_2CH(CH3)C(O)O$.

According to one embodiment, there is provided a compound of formula (I), wherein $R_2$ is $CH_3$.

According to one embodiment, there is provided a compound of formula (I), wherein $R_3$ is —OH, —OBz and —OAc, butanoyloxy, pentanoyloxy, (CH3)3COONHCH (CH3)C(O)O, and $NH_2CH(CH3)C(O)O$.

According to one embodiment, there is provided a compound of formula (I), wherein $R_4$ is $CH_3$.

According to one embodiment, there is provided a compound of formula (I), wherein $R^a$ is $CH_3$, isopropyl, isobutyl, and benzyl.

According to one embodiment, there is provided a compound of formula (I), wherein C1 of sugar moiety is bonded to the ring Nitrogen atom of optionally substituted B. In this embodiment, preferably, B is a pyrimidine, purine or an equivalent.

According to one embodiment, there is provided a compound of formula (I), wherein B is optionally substituted purine. In this embodiment, preferably, B is 6-oxo purine, 6-chloro purine and 6-amino purine, wherein amino group of 6-amino purine is optionally substituted.

According to one embodiment, there is provided a compound of formula (I), wherein B is optionally substituted Pyrimidine.

According to one embodiment, there is provided a compound of formula (I), wherein B is optionally substituted Pyrimidine. In this embodiment, preferably, B is optionally substituted uracil, thiamine and cytosine.

The present patent application also concerned compounds of formula (IA):

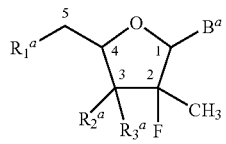

wherein, $B^a$ can be Nitrogen heterocycle of from C3 to C15, such as optionally substituted purine, pyrimidine (wherein purine base is selected from adenine or guanine; pyrimidine base is selected from cytosine, uracil, or thymine) pteridine, triazolopyridine, imidazolopyridine, imidazolotriazine, pyrrolopyrimidine, or pyrazolopyrimidine; Nitrogen heterocycle may be bound to the sugar moiety in the nucleoside through any available ring Nitrogen atom;

$R_2^a$ and $R_3^a$ independently can be selected from OH, methyl, $CH_3C(O)O$, $CH_3CH(CH_3)C(O)O$, $CH_3CH2CH2CH2C(O)O$, $PhC(O)O$, or $NH_2CH(R^a)C(O)O$ (wherein $R^a$ can be H, alkyl, or benezyl);

$R_1^a$ can be OH, $CH_3C(O)O$, $PhC(O)O$, $CH_3CH_2CH_2C(O)O$, $CH_3CH(CH_3)C(O)O$, $CH_3CH_2CH_2CH_2C(O)O$ or $NH_2CH(R^a)C(O)O$ (wherein $R^a$ can be H, alkyl, or benezyl).

Pharmaceutically acceptable salts of the compounds of the formula (IA) are also contemplated. Likewise, pharmaceutically acceptable solvates, including hydrates, of the compounds of the formula (IA) are contemplated.

It should be understood that the formula (IA) structurally encompasses all stereoisomers, including enatiomers and diastereomers, which may be contemplated from the chemical structure of the genus described herein.

Also contemplated are prodrugs of the compounds of the formula (IA), including ester prodrugs.

The present patent application also concerned intermediates of 5-carbon sugar compounds of formula (II) with substitution at 2-position:

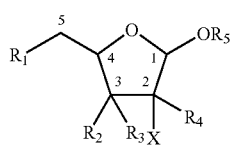

wherein, $R_5$ can be alkyl, hydrogen, acyl, aryl, alkyl carbonyloxy, aryl carbonyloxy, silyl, sulfonyl, or $OR_5$ together represent as halogen;

X can be halogen;

$R_4$ can be alkyl group;

$R_2$ and $R_3$ independently can be selected from OH, alkyl, alkenyl, halogen, alkynyl, cycloalkyl, $N_3$, $CF_3$, $NH_2$, or CN; $R_2$ and $R_3$ can be together form oxo (=O) group;

$R_1$ can be H, OH, —{P(O)(OH)O-}nR, alkyl, hydrogen, acyl, benzoyl, aryl, alkyl carbonyloxy, aryl carbonyloxy, silyl, heterocycloalkyl, sulfonyl, RCONHCH(Ra)C(O)O, or $NH_2CH(R^a)C(O)O$ (wherein $R^a$ can be H, alkyl, or benezyl);

R can be alkyl, hydrogen, acyl, aryl, alkyl carbonyloxy, aryl carbonyloxy, or heterocycloalkyl;

$R_1$, $R_2$, $R_3$, $R_4$, $R_5$ and R are independently can be further substituted wherever appropriate by a group like halogen, alkyl, alkenyl, alkynyl, aryl, alkylaryl, aralkyl, cycloalkyl, heterocyclyl, heterocycloakyl, hydroxy, amino, cyano, azido, carbonyl, oxycarbonyl, sulfonyl, sulfonyloxy, or carbonyloxy.

Pharmaceutically acceptable salts of the compounds of the formula (II) are also contemplated. Likewise, pharmaceutically acceptable solvates, including hydrates, of the compounds of the formula (II) are contemplated.

It should be understood that the formula (II) structurally encompasses all stereoisomers, including enatiomers and diastereomers, which may be contemplated from the chemical structure of the genus described herein.

Also contemplated are prodrugs of the compounds of the formula (II), including ester prodrugs.

According to one embodiment, there is provided compounds of formula (II):

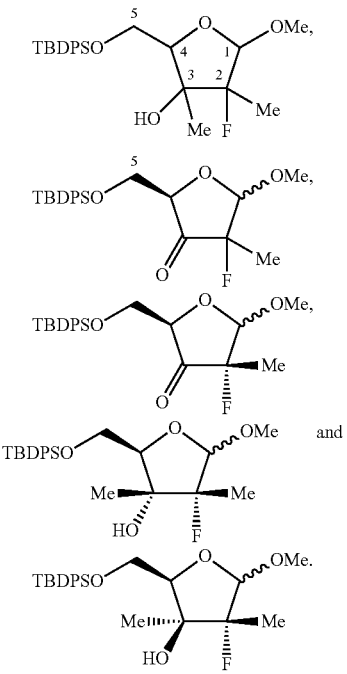

According to one embodiment, there is also provided a compound of formula (II), wherein the structures of two diastereomers are represented by

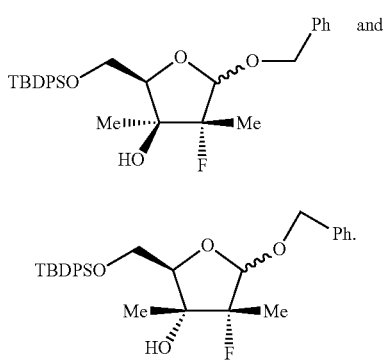

Another preferred embodiment of the present invention is a compound of Formula (IIA),

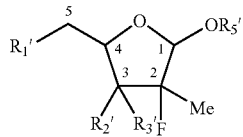

wherein,

R$_1$' can be OH, O—CH2-Ph, O-t-butyldiphenylsilyl, O-Me;

R$_2$' and R$_3$' independently can be selected from hydrogen, methyl, or hydroxyl; R$_2$' and R$_3$' can be together form oxo (=O) group;

R$_5$' can be hydroxyl, O—CH2-Ph, O-t-butyldiphenylsilyl, O-Me, O—C(O)CH$_3$, or O-trimethylsilyl.

Pharmaceutically acceptable salts of the compounds of the formula (IIA) are also contemplated. Likewise, pharmaceutically acceptable solvates, including hydrates, of the compounds of the formula (IIA) are contemplated.

It should be understood that the formula (IIA) structurally encompasses all stereoisomers, including enatiomers and diastereomers, which may be contemplated from the chemical structure of the genus described herein.

Also contemplated are prodrugs of the compounds of the formula (IIA), including ester prodrugs.

Below are the representative compounds, which are illustrative in nature only and are not intended to limit to the scope of the invention (Nomenclature has been generated from Chem. Draw Ultra 9.0 version):

((2R,4R)-3-(benzoyloxy)-5-(6-chloro-9H-purin-9-yl)-4-fluoro-3,4-dimethyltetrahydrofuran-2-yl)methyl benzoate (Compound 1), (2R,4R)-5-(6-amino-9H-purin-9-yl)-4-fluoro-2-(hydroxymethyl)-3,4-dimethyltetrahydrofuran-3-ol (Compound 2A), (2R,4R)-4-fluoro-2-(hydroxymethyl)-5-(6-methoxy-9H-purin-9-yl)-3,4-dimethyltetrahydrofuran-3-ol (Compound 2B), ((2R,4R)-3-acetoxy-5-(6-chloro-9H-purin-9-yl)-4-fluoro-3,4-dimethyltetrahydrofuran-2-yl)methyl benzoate (Compound 3), ((2R,4R)-3-acetoxy-5-(6-(cyclopropylamino)-9H-purin-9-yl)-4-fluoro-3,4-dimethyltetrahydrofuran-2-yl)methyl benzoate (Compound 4), ((2R,4R)-3-acetoxy-4-fluoro-5-(6-(4-fluorobenzylamino)-9H-purin-9-yl)-3,4-dimethyltetrahydrofuran-2-yl)methyl benzoate (Compound 5), ((2R,4R)-3-acetoxy-5-(6-(cyclobutylamino)-9H-purin-9-yl)-4-fluoro-3,4-dimethyltetrahydrofuran-2-yl)methyl benzoate (Compound 6), ((2R,4R)-3-acetoxy-4-fluoro-5-(6-(furan-2-ylmethylamino)-9H-purin-9-yl)-3,4-dimethyltetrahydrofuran-2-yl)methyl benzoate (Compound 7), ((2R,4R)-3-acetoxy-4-fluoro-5-(6-(isobutylamino)-9H-purin-9-yl)-3,4-dimethyltetrahydrofuran-2-yl)methyl benzoate (Compound 8), ((2R,4R)-3-acetoxy-4-fluoro-5-(6-(3-methoxybenzylamino)-9H-purin-9-yl)-3,4-dimethyltetrahydrofuran-2-yl)methyl benzoate (Compound 9), ((2R,4R)-3-acetoxy-5-(6-(3-chlorobenzylamino)-9H-purin-9-yl)-4-fluoro-3,4-dimethyltetrahydrofuran-2-yl)methyl benzoate (Compound 10), ((2R,4R)-3-acetoxy-4-fluoro-5-(6-(2-methoxybenzylamino)-9H-purin-9-yl)-3,4-dimethyltetrahydrofuran-2-yl)methyl benzoate (Compound 11), ((2R,4R)-3-acetoxy-5-(6-(2-chlorobenzylamino)-9H-purin-9-yl)-4-fluoro-3,4-dimethyltetrahydrofuran-2-yl)methyl benzoate (Compound 12), ((2R,4R)-3-acetoxy-4-fluoro-3,4-dimethyl-5-(6-morpholino-9H-purin-9-yl)tetrahydrofuran-2-yl)methyl benzoate (Compound 13), ((2R,4R)-3-acetoxy-5-(6-(cycloheptylamino)-9H-purin-9-yl)-4-fluoro-3,4-dimethyltetrahydrofuran-2-yl)methyl benzoate (Compound 14), (2R,4R)-5-(6-(cycloheptylamino)-9H-purin-9-yl)-4-fluoro-2-(hydroxymethyl)-3,4-dimethyltetrahydrofuran-3-ol (Compound 15), (2R,4R)-5-(6-(cyclopropylamino)-9H-purin-9-yl)-4-fluoro-2-(hydroxymethyl)-3,4-dimethyltetrahydrofuran-3-ol (Compound 16), ((2R,4R)-3-acetoxy-5-(6-(cyclopentylamino)-9H-purin-9-yl)-4-fluoro-3,4-dimethyltetrahydrofuran-2-yl)methyl benzoate (Compound 17), ((2R,4R)-3-acetoxy-5-(6-(cyclohexylamino)-9H-purin-9-yl)-4-fluoro-3,4-dimethyltetrahydrofuran-2-yl)methyl benzoate (Compound 18), ((2R,4R)-3-acetoxy-5-(2,4-dioxo-3,4-dihydropyrimidin-1(2H)-yl)-4-fluoro-3,4-dimethyltetrahydrofuran-2-yl)methyl benzoate (Compound 19), ((2R,4R)-3-acetoxy-4-fluoro-3,4-dimethyl-5-(5-methyl-2,4-dioxo-3,4-dihydropyrimidin-1(2H)-yl)tetrahydrofuran-2-yl)methyl acetate (Compound 20), ((2R,4R)-3-acetoxy-5-(4-benzamido-2-oxopyrimidin-1(2H)-yl)-4-fluoro-3,4-dimethyltetrahydrofuran-2-yl)methyl benzoate (Compound 21), 1-((2R,4R)-3-fluoro-4-hydroxy-5-(hydroxymethyl)-3,4-dimethyltetrahydrofuran-2-yl)pyrimidine-2,4(1H,3H)-dione (Compound 22), 4-amino-1-((2R,4R)-3-fluoro-4-hydroxy-5-(hydroxymethyl)-3,4-dimethyltetrahydrofuran-2-yl)pyrimidin-2(1H)-one (Compound 23), 1-((2R,4R)-3-fluoro-4-hydroxy-5-(hydroxymethyl)-3,4-dimethyltetrahydrofuran-2-yl)-5-methylpyrimidine-2,4(1H,3H)-dione (Compound 24), ((2R,4R)-3-acetoxy-5-(6-(cyclopropylmethylamino)-9H-purin-9-yl)-4-fluoro-3,4-dimethyltetrahydrofuran-2-yl) methyl benzoate (Compound 25), ((2R,4R)-3-acetoxy-5-(2-amino-6-chloro-9H-purin-9-yl)-4-fluoro-3,4-dimethyltetrahydrofuran-2-yl)methyl benzoate (Compound 26), (2R,4R)-5-(6-(cyclopentylamino)-9H-purin-9-yl)-4-fluoro-2-(hydroxymethyl)-3,4-dimethyltetrahydrofuran-3-ol (Compound 27), (2R,4R)-5-(6-(cyclohexylamino)-9H-purin-9-yl)-4-fluoro-2-(hydroxymethyl)-3,4-dimethyltetrahydrofuran-3-ol (Compound 28), ((2R,4R)-3-acetoxy-5-(6-(benzylamino)-9H-purin-9-yl)-4-fluoro-3,4-dimethyltetrahydrofuran-2-yl)methyl benzoate (Compound 29), (2R,4R)-5-(6-(cyclopropylmethylamino)-9H-purin-9-yl)-4-fluoro-2-(hydroxymethyl)-3,4-dimethyltetrahydrofuran-3-ol (Compound 30), ((2R,4R)-5-(2,4-dioxo-3,4-dihydropyrimidin-1(2H)-yl)-4-fluoro-3-hydroxy-3,4-dimethyltetrahydrofuran-2-yl)methyl butyrate (Compound 31), ((2R,4R)-5-(2,4-dioxo-3,4-dihydropyrimidin-1(2H)-yl)-4-fluoro-3-hydroxy-3,4-dimethyltetrahydrofuran-2-yl)methyl pentanoate (Compound 32), ((2R,4R)-3-acetoxy-4-fluoro-3,4-dimethyl-5-(6-oxo-1H-purin-9(6H)-yl)tetrahydrofuran-2-yl)methyl benzoate (Compound 33), 9-((3R,5R)-3-fluoro-4-hydroxy-5-(hydroxymethyl)-3,4-dimethyltetrahydrofuran-2-yl)-1H-purin-6(9H)-one (Compound 34), ((2R,4R)-3-acetoxy-4-fluoro-3,4-dimethyl-5-(5-methyl-2,4-dioxo-3,4-dihydropyrimidin-1(2H)-yl)tetrahydrofuran-2-yl)methyl benzoate (Compound 35), ((2R,4R)-5-(2,4-dioxo-3,4-dihydropyrimidin-1(2H)-yl)-4-fluoro-3-hydroxy-3,4-dimethyltetrahydrofuran-2-yl)methyl isobutyrat (Compound No. 36), (2R,4R)-4-fluoro-2-(hydroxymethyl)-3,4-dimethyl-5-(6-morpholino-9H-purin-9-yl)tetrahydrofuran-3-ol (Compound No. 37), ((2R,4R)-3-acetoxy-4-fluoro-5-(5-fluoro-2,4-dioxo-3,4-dihydropyrimidin-1(2H)-yl)-3,4-dimethyltetrahydrofuran-2-yl)methyl benzoate (Compound No. 38), 5-fluoro-1-((3R,5R)-3-fluoro-4-hydroxy-5-(hydroxymethyl)-3,4-dimethyltetrahydrofuran-2-yl)pyrimidine-2,4(1H,3H)-dione (Compound No. 39), ((2R,4R)-4-fluoro-3-hydroxy-3,4-dimethyl-5-(6-morpholino-9H-purin-9-yl)tetrahydrofuran-2-yl)methyl pentanoate (Compound No. 40), ((2R,4R)-4-fluoro-3-hydroxy-3,4-dimethyl-5-(6-morpholino-9H-purin-9-yl)tetrahydrofuran-2-yl)methyl butyrate (Compound No. 41), ((2R,4R)-4-fluoro-3-hydroxy-3,4-dimethyl-5-(6-morpholino-9H-purin-9-yl)tetrahydrofuran-2-yl)methyl isobutyrate (Compound No. 42), (2R,4R)-5-(6-(3-chlorobenzylamino)-9H-purin-9-yl)-4-fluoro-2-(hydroxymethyl)-3,4-dimethyltetrahydrofuran-3-ol (Compound No. 43), (2R,4R)-4-fluoro-5-(6-(furan-2-ylmethylamino)-9H-purin-9-yl)-2-(hydroxymethyl)-3,4-dimethyltetrahydrofuran-3-ol (Compound No. 44), (2R,4R)-5-(6-(2-chlorobenzylamino)-9H-purin-9-yl)-4-fluoro-2-(hydroxymethyl)-3,4-dimethyltetrahydrofuran-3-ol (Compound No. 45), (2R,4R)-5-(6-(cyclobutylamino)-9H-purin-9-yl)-4-fluoro-2-(hydroxymethyl)-3,4-dimethyltetrahydrofuran-3-ol (Compound No. 46), (2S)-((2R,4R)-4-fluoro-3-hydroxy-3,4-dimethyl-5-(5-methyl-2,4-dioxo-3,4-dihydropyrimidin-1(2H)-yl)tetrahydrofuran-2-yl)methyl 2-(tert-butoxycarbonylamino)propanoate (Compound No. 47), ((2R,4R)-4-fluoro-3-hydroxy-3,4-dimethyl-5-(5-methyl-2,4-dioxo-3,4-dihydropyrimidin-1(2H)-yl)tetrahydrofuran-2-yl)methyl 2-aminopropanoate (Compound No. 48), or pharmaceutically acceptable salts, solvates, including hydrates and prodrugs of compounds are also contemplated.

Determination of Absolute Stereochemistry:

In one embodiment structure of compounds of present invention has determined by single crystal X-ray crystallography by growing crystals from single or mixed solvents suitable for diffraction studies.

Below are the some more representative compounds, which are illustrative in nature only and are not intended to limit to the scope of the invention (Nomenclature has been generated from Chem. Draw Ultra 9.0 version):

((2R,3R,4R,5R)-3-(benzoyloxy)-5-(6-chloro-9H-purin-9-yl)-4-fluoro-3,4-dimethyltetrahydrofuran-2-yl)methyl benzoate, ((2R,3R,4R,5S)-3-(benzoyloxy)-5-(6-chloro-9H-purin-9-yl)-4-fluoro-3,4-dimethyltetrahydrofuran-2-yl)methyl benzoate, ((2R,3S,4R,5R)-3-(benzoyloxy)-5-(6-chloro-9H-purin-9-yl)-4-fluoro-3,4-dimethyltetrahydrofuran-2-yl)methyl benzoate, ((2R,3S,4R,5S)-3-(benzoyloxy)-5-(6-chloro-9H-purin-9-yl)-4-fluoro-3,4-dimethyltetrahydrofuran-2-yl)methyl benzoate, (2R,3R,4R,5R)-5-(6-amino-9H-purin-9-yl)-4-fluoro-2-(hydroxymethyl)-3,4-dimethyltetrahydrofuran-3-ol, (2R,3R,4R,5S)-5-(6-amino-9H-purin-9-yl)-4-fluoro-2-(hydroxymethyl)-3,4-dimethyltetrahydrofuran-3-ol, (2R,3S,4R,5R)-5-(6-amino-9H-purin-9-yl)-4-fluoro-2-(hydroxymethyl)-3,4-dimethyltetrahydrofuran-3-ol, (2R,3S,4R,5S)-5-(6-amino-9H-purin-9-yl)-4-fluoro-2-(hydroxymethyl)-3,4-dimethyltetrahydrofuran-3-ol, (2R,3R,4R,5R)-4-fluoro-2-(hydroxymethyl)-5-(6-methoxy-9H-purin-9-yl)-3,4-dimethyltetrahydrofuran-3-ol, (2R,3R,4R,5S)-4-fluoro-2-(hydroxymethyl)-5-(6-methoxy-9H-purin-9-yl)-3,4-dimethyltetrahydrofuran-3-ol, (2R,3S,4R,5R)-4-fluoro-2-(hydroxymethyl)-5-(6-methoxy-9H-purin-9-yl)-3,4-dimethyltetrahydrofuran-3-ol, (2R,3S,4R,5S)-4-fluoro-2-(hydroxymethyl)-5-(6-methoxy-9H-purin-9-yl)-3,4-dimethyltetrahydrofuran-3-ol, ((2R,3R,4R,5R)-3-acetoxy-5-(6-chloro-9H-purin-9-yl)-4-fluoro-3,4-dimethyltetrahydrofuran-2-yl)methyl benzoate, ((2R,3R,4R,5S)-3-acetoxy-5-(6-chloro-9H-purin-9-yl)-4-fluoro-3,4-dimethyltetrahydrofuran-2-yl)methyl benzoate, ((2R,3S,4R,5R)-3-acetoxy-5-(6-chloro-9H-purin-9-yl)-4-fluoro-3,4-dimethyltetrahydrofuran-2-yl)methyl benzoate, ((2R,3S,4R,5S)-3-acetoxy-5-(6-chloro-9H-purin-9-yl)-4-fluoro-3,4-dimethyltetrahydrofuran-2-yl)methyl benzoate, ((2R,3R,4R,5R)-3-acetoxy-5-(6-(cyclopropylamino)-9H-purin-9-yl)-4-fluoro-3,4-dimethyltetrahydrofuran-2-yl)methyl benzoate, ((2R,3R,4R,5S)-3-acetoxy-5-(6-(cyclopropylamino)-9H-purin-9-yl)-4-fluoro-3,4-dimethyltetrahydrofuran-2-yl)methyl benzoate, ((2R,3S,4R,5R)-3-acetoxy-5-(6-(cyclopropylamino)-9H-purin-9-yl)-4-fluoro-3,4-dimethyltetrahydrofuran-2-yl)methyl benzoate, ((2R,3S,4R,5S)-3-acetoxy-5-(6-(cyclopropylamino)-9H-purin-9-yl)-4-fluoro-3,4-dimethyltetrahydrofuran-2-yl)methyl benzoate, ((2R,3R,4R,5R)-3-acetoxy-4-fluoro-5-(6-(4-fluorobenzylamino)-9H-purin-9-yl)-3,4-dimethyltetrahydrofuran-2-yl)methyl benzoate, ((2R,3R,4R,5S)-3-acetoxy-4-fluoro-5-(6-(4-fluorobenzylamino)-9H-purin-9-yl)-3,4-dimethyltetrahydrofuran-2-yl)methyl benzoate, ((2R,3S,4R,5R)-3-acetoxy-4-fluoro-5-(6-(4-fluorobenzylamino)-9H-purin-9-yl)-3,4-dimethyltetrahydrofuran-2-yl)methyl benzoate, ((2R,3S,4R,5S)-3-acetoxy-4-fluoro-5-(6-(4-fluorobenzylamino)-9H-purin-9-yl)-3,4-dimethyltetrahydrofuran-2-yl)methyl benzoate, ((2R,3R,4R,5R)-3-acetoxy-5-(6-(cyclobutylamino)-9H-purin-9-yl)-4-fluoro-3,4-dimethyltetrahydrofuran-2-yl)methyl benzoate, ((2R,3R,4R,5S)-3-acetoxy-5-(6-(cyclobutylamino)-9H-purin-9-yl)-4-fluoro-3,4-dimethyltetrahydrofuran-2-yl)methyl benzoate, ((2R,3S,4R,5R)-3-acetoxy-5-(6-(cyclobutylamino)-9H-purin-9-yl)-4-fluoro-3,4-dimethyltetrahydrofuran-2-yl)methyl benzoate, ((2R,3S,4R,5S)-3-acetoxy-5-(6-(cyclobutylamino)-9H-purin-9-yl)-4-fluoro-3,4-dimethyltetrahydrofuran-2-yl)methyl benzoate,
((2R,3R,4R,5R)-3-acetoxy-4-fluoro-5-(6-(furan-2-ylmethylamino)-9H-purin-9-yl)-3,4-dimethyltetrahydrofuran-2-yl)methyl benzoate,
((2R,3R,4R,5S)-3-acetoxy-4-fluoro-5-(6-(furan-2-ylmethylamino)-9H-purin-9-yl)-3,4-dimethyltetrahydrofuran-2-yl)methyl benzoate,
((2R,3S,4R,5R)-3-acetoxy-4-fluoro-5-(6-(furan-2-ylmethylamino)-9H-purin-9-yl)-3,4-dimethyltetrahydrofuran-2-yl)methyl benzoate,
((2R,3S,4R,5S)-3-acetoxy-4-fluoro-5-(6-(furan-2-ylmethylamino)-9H-purin-9-yl)-3,4-dimethyltetrahydrofuran-2-yl)methyl benzoate,
((2R,3R,4R,5R)-3-acetoxy-4-fluoro-5-(6-(isobutylamino)-9H-purin-9-yl)-3,4-dimethyltetrahydrofuran-2-yl)methyl benzoate,
((2R,3R,4R,5S)-3-acetoxy-4-fluoro-5-(6-(isobutylamino)-9H-purin-9-yl)-3,4-dimethyltetrahydrofuran-2-yl)methyl benzoate,
((2R,3S,4R,5R)-3-acetoxy-4-fluoro-5-(6-(isobutylamino)-9H-purin-9-yl)-3,4-dimethyltetrahydrofuran-2-yl)methyl benzoate,
((2R,3S,4R,5S)-3-acetoxy-4-fluoro-5-(6-(isobutylamino)-9H-purin-9-yl)-3,4-dimethyltetrahydrofuran-2-yl)methyl benzoate,
((2R,3R,4R,5R)-3-acetoxy-4-fluoro-5-(6-(3-methoxybenzylamino)-9H-purin-9-yl)-3,4-dimethyltetrahydrofuran-2-yl)methyl benzoate,
((2R,3R,4R,5S)-3-acetoxy-4-fluoro-5-(6-(3-methoxybenzylamino)-9H-purin-9-yl)-3,4-dimethyltetrahydrofuran-2-yl)methyl benzoate,
((2R,3S,4R,5R)-3-acetoxy-4-fluoro-5-(6-(3-methoxybenzylamino)-9H-purin-9-yl)-3,4-dimethyltetrahydrofuran-2-yl)methyl benzoate,
((2R,3S,4R,5S)-3-acetoxy-4-fluoro-5-(6-(3-methoxybenzylamino)-9H-purin-9-yl)-3,4-dimethyltetrahydrofuran-2-yl)methyl benzoate,
((2R,3R,4R,5R)-3-acetoxy-5-(6-(3-chlorobenzylamino)-9H-purin-9-yl)-4-fluoro-3,4-dimethyltetrahydrofuran-2-yl)methyl benzoate,
((2R,3R,4R,5S)-3-acetoxy-5-(6-(3-chlorobenzylamino)-9H-purin-9-yl)-4-fluoro-3,4-dimethyltetrahydrofuran-2-yl)methyl benzoate,
((2R,3S,4R,5R)-3-acetoxy-5-(6-(3-chlorobenzylamino)-9H-purin-9-yl)-4-fluoro-3,4-dimethyltetrahydrofuran-2-yl)methyl benzoate,
((2R,3S,4R,5S)-3-acetoxy-5-(6-(3-chlorobenzylamino)-9H-purin-9-yl)-4-fluoro-3,4-dimethyltetrahydrofuran-2-yl)methyl benzoate,
((2R,3R,4R,5R)-3-acetoxy-4-fluoro-5-(6-(2-methoxybenzylamino)-9H-purin-9-yl)-3,4-dimethyltetrahydrofuran-2-yl)methyl benzoate,
((2R,3R,4R,5S)-3-acetoxy-4-fluoro-5-(6-(2-methoxybenzylamino)-9H-purin-9-yl)-3,4-dimethyltetrahydrofuran-2-yl)methyl benzoate,
((2R,3S,4R,5R)-3-acetoxy-4-fluoro-5-(6-(2-methoxybenzylamino)-9H-purin-9-yl)-3,4-dimethyltetrahydrofuran-2-yl)methyl benzoate,
((2R,3S,4R,5S)-3-acetoxy-4-fluoro-5-(6-(2-methoxybenzylamino)-9H-purin-9-yl)-3,4-dimethyltetrahydrofuran-2-yl)methyl benzoate,
((2R,3R,4R,5R)-3-acetoxy-5-(6-(2-chlorobenzylamino)-9H-purin-9-yl)-4-fluoro-3,4-dimethyltetrahydrofuran-2-yl)methyl benzoate,
((2R,3R,4R,5S)-3-acetoxy-5-(6-(2-chlorobenzylamino)-9H-purin-9-yl)-4-fluoro-3,4-dimethyltetrahydrofuran-2-yl)methyl benzoate,
((2R,3S,4R,5R)-3-acetoxy-5-(6-(2-chlorobenzylamino)-9H-purin-9-yl)-4-fluoro-3,4-dimethyltetrahydrofuran-2-yl)methyl benzoate,
((2R,3S,4R,5S)-3-acetoxy-5-(6-(2-chlorobenzylamino)-9H-purin-9-yl)-4-fluoro-3,4-dimethyltetrahydrofuran-2-yl)methyl benzoate,
((2R,3R,4R,5R)-3-acetoxy-4-fluoro-3,4-dimethyl-5-(6-morpholino-9H-purin-9-yl)tetrahydrofuran-2-yl)methyl benzoate,
((2R,3R,4R,5S)-3-acetoxy-4-fluoro-3,4-dimethyl-5-(6-morpholino-9H-purin-9-yl)tetrahydrofuran-2-yl)methyl benzoate,
((2R,3S,4R,5R)-3-acetoxy-4-fluoro-3,4-dimethyl-5-(6-morpholino-9H-purin-9-yl)tetrahydrofuran-2-yl)methyl benzoate,
((2R,3S,4R,5S)-3-acetoxy-4-fluoro-3,4-dimethyl-5-(6-morpholino-9H-purin-9-yl)tetrahydrofuran-2-yl)methyl benzoate,
((2R,3R,4R,5R)-3-acetoxy-5-(6-(cycloheptylamino)-9H-purin-9-yl)-4-fluoro-3,4-dimethyltetrahydrofuran-2-yl)methyl benzoate,
((2R,3R,4R,5S)-3-acetoxy-5-(6-(cycloheptylamino)-9H-purin-9-yl)-4-fluoro-3,4-dimethyltetrahydrofuran-2-yl)methyl benzoate,
((2R,3S,4R,5R)-3-acetoxy-5-(6-(cycloheptylamino)-9H-purin-9-yl)-4-fluoro-3,4-dimethyltetrahydrofuran-2-yl)methyl benzoate,
((2R,3S,4R,5S)-3-acetoxy-5-(6-(cycloheptylamino)-9H-purin-9-yl)-4-fluoro-3,4-dimethyltetrahydrofuran-2-yl)methyl benzoate,
(2R,3R,4R,5R)-5-(6-(cycloheptylamino)-9H-purin-9-yl)-4-fluoro-2-(hydroxymethyl)-3,4-dimethyltetrahydrofuran-3-ol,
(2R,3R,4R,5S)-5-(6-(cycloheptylamino)-9H-purin-9-yl)-4-fluoro-2-(hydroxymethyl)-3,4-dimethyltetrahydrofuran-3-ol,
(2R,3S,4R,5R)-5-(6-(cycloheptylamino)-9H-purin-9-yl)-4-fluoro-2-(hydroxymethyl)-3,4-dimethyltetrahydrofuran-3-ol,
(2R,3S,4R,5S)-5-(6-(cycloheptylamino)-9H-purin-9-yl)-4-fluoro-2-(hydroxymethyl)-3,4-dimethyltetrahydrofuran-3-ol,
(2R,3R,4R,5R)-5-(6-(cyclopropylamino)-9H-purin-9-yl)-4-fluoro-2-(hydroxymethyl)-3,4-dimethyltetrahydrofuran-3-ol,
(2R,3R,4R,5S)-5-(6-(cyclopropylamino)-9H-purin-9-yl)-4-fluoro-2-(hydroxymethyl)-3,4-dimethyltetrahydrofuran-3-ol,
(2R,3S,4R,5R)-5-(6-(cyclopropylamino)-9H-purin-9-yl)-4-fluoro-2-(hydroxymethyl)-3,4-dimethyltetrahydrofuran-3-ol,
(2R,3S,4R,5S)-5-(6-(cyclopropylamino)-9H-purin-9-yl)-4-fluoro-2-(hydroxymethyl)-3,4-dimethyltetrahydrofuran-3-ol,
((2R,3R,4R,5R)-3-acetoxy-5-(6-(cyclopentylamino)-9H-purin-9-yl)-4-fluoro-3,4-dimethyltetrahydrofuran-2-yl)methyl benzoate,
((2R,3R,4R,5S)-3-acetoxy-5-(6-(cyclopentylamino)-9H-purin-9-yl)-4-fluoro-3,4-dimethyltetrahydrofuran-2-yl)methyl benzoate,
((2R,3S,4R,5R)-3-acetoxy-5-(6-(cyclopentylamino)-9H-purin-9-yl)-4-fluoro-3,4-dimethyltetrahydrofuran-2-yl)methyl benzoate, ((2R,3S,4R,5S)-3-acetoxy-5-(6-(cyclopentylamino)-9H-purin-9-yl)-4-fluoro-3,4-dimethyltetrahydrofuran-2-yl)methyl benzoate,
((2R,3R,4R,5R)-3-acetoxy-5-(6-(cyclohexylamino)-9H-purin-9-yl)-4-fluoro-3,4-dimethyltetrahydrofuran-2-yl)methyl benzoate,
((2R,3R,4R,5S)-3-acetoxy-5-(6-(cyclohexylamino)-9H-purin-9-yl)-4-fluoro-3,4-dimethyltetrahydrofuran-2-yl)methyl benzoate,
((2R,3S,4R,5R)-3-acetoxy-5-(6-(cyclohexylamino)-9H-purin-9-yl)-4-fluoro-3,4-dimethyltetrahydrofuran-2-yl)methyl benzoate,
((2R,3S,4R,5S)-3-acetoxy-5-(6-(cyclohexylamino)-9H-purin-9-yl)-4-fluoro-3,4-dimethyltetrahydrofuran-2-yl)methyl benzoate,
((2R,3R,4R,5R)-3-acetoxy-5-(2,4-dioxo-3,4-dihydropyrimidin-1(2H)-yl)-4-fluoro-3,4-dimethyltetrahydrofuran-2-yl)methyl benzoate,
((2R,3R,4R,5S)-3-acetoxy-5-(2,4-dioxo-3,4-dihydropyrimidin-1(2H)-yl)-4-fluoro-3,4-dimethyltetrahydrofuran-2-yl)methyl benzoate,
((2R,3S,4R,5R)-3-acetoxy-5-(2,4-dioxo-3,4-dihydropyrimidin-1(2H)-yl)-4-fluoro-3,4-dimethyltetrahydrofuran-2-yl)methyl benzoate,
((2R,3S,4R,5S)-3-acetoxy-5-(2,4-dioxo-3,4-dihydropyrimidin-1(2H)-yl)-4-fluoro-3,4-dimethyltetrahydrofuran-2-yl)methyl benzoate,
((2R,3R,4R,5R)-3-acetoxy-4-fluoro-3,4-dimethyl-5-(5-methyl-2,4-dioxo-3,4-dihydropyrimidin-1(2H)-yl)tetrahydrofuran-2-yl)methyl acetate,
((2R,3R,4R,5S)-3-acetoxy-4-fluoro-3,4-dimethyl-5-(5-methyl-2,4-dioxo-3,4-dihydropyrimidin-1(2H)-yl)tetrahydrofuran-2-yl)methyl acetate,
((2R,3S,4R,5R)-3-acetoxy-4-fluoro-3,4-dimethyl-5-(5-methyl-2,4-dioxo-3,4-dihydropyrimidin-1(2H)-yl)tetrahydrofuran-2-yl)methyl acetate,
((2R,3S,4R,5S)-3-acetoxy-4-fluoro-3,4-dimethyl-5-(5-methyl-2,4-dioxo-3,4-dihydropyrimidin-1(2H)-yl)tetrahydrofuran-2-yl)methyl acetate,
((2R,3R,4R,5R)-3-acetoxy-5-(4-benzamido-2-oxopyrimidin-1(2H)-yl)-4-fluoro-3,4-dimethyltetrahydrofuran-2-yl)methyl benzoate,
((2R,3R,4R,5S)-3-acetoxy-5-(4-benzamido-2-oxopyrimidin-1(2H)-yl)-4-fluoro-3,4-dimethyltetrahydrofuran-2-yl)methyl benzoate,
((2R,3S,4R,5R)-3-acetoxy-5-(4-benzamido-2-oxopyrimidin-1(2H)-yl)-4-fluoro-3,4-dimethyltetrahydrofuran-2-yl)methyl benzoate,
((2R,3S,4R,5S)-3-acetoxy-5-(4-benzamido-2-oxopyrimidin-1(2H)-yl)-4-fluoro-3,4-dimethyltetrahydrofuran-2-yl)methyl benzoate,
1-((2R,3R,4R,5R)-3-fluoro-4-hydroxy-5-(hydroxymethyl)-3,4-dimethyltetrahydrofuran-2-yl)pyrimidine-2,4(1H,3H)-dione,
1-((2R,3R,4R,5S)-3-fluoro-4-hydroxy-5-(hydroxymethyl)-3,4-dimethyltetrahydrofuran-2-yl)pyrimidine-2,4(1H,3H)-dione,
1-((2R,3S,4R,5R)-3-fluoro-4-hydroxy-5-(hydroxymethyl)-3,4-dimethyltetrahydrofuran-2-yl)pyrimidine-2,4(1H,3H)-dione,
1-((2R,3S,4R,5S)-3-fluoro-4-hydroxy-5-(hydroxymethyl)-3,4-dimethyltetrahydrofuran-2-yl)pyrimidine-2,4(1H,3H)-dione,
4-amino-1-((2R,3R,4R,5R)-3-fluoro-4-hydroxy-5-(hydroxymethyl)-3,4-dimethyltetrahydrofuran-2-yl)pyrimidin-2(1H)-one,
4-amino-1-((2R,3R,4R,5S)-3-fluoro-4-hydroxy-5-(hydroxymethyl)-3,4-dimethyltetrahydrofuran-2-yl)pyrimidin-2(1H)-one,
4-amino-1-((2R,3S,4R,5R)-3-fluoro-4-hydroxy-5-(hydroxymethyl)-3,4-dimethyltetrahydrofuran-2-yl)pyrimidin-2(1H)-one,
4-amino-1-((2R,3S,4R,5S)-3-fluoro-4-hydroxy-5-(hydroxymethyl)-3,4-dimethyltetrahydrofuran-2-yl)pyrimidin-2(1H)-one,
1-((2R,3R,4R,5R)-3-fluoro-4-hydroxy-5-(hydroxymethyl)-3,4-dimethyltetrahydrofuran-2-yl)-5-methylpyrimidine-2,4(1H,3H)-dione,
1-((2R,3R,4R,5S)-3-fluoro-4-hydroxy-5-(hydroxymethyl)-3,4-dimethyltetrahydrofuran-2-yl)-5-methylpyrimidine-2,4(1H,3H)-dione,
1-((2R,3S,4R,5R)-3-fluoro-4-hydroxy-5-(hydroxymethyl)-3,4-dimethyltetrahydrofuran-2-yl)-5-methylpyrimidine-2,4(1H,3H)-dione,
1-((2R,3S,4R,5S)-3-fluoro-4-hydroxy-5-(hydroxymethyl)-3,4-dimethyltetrahydrofuran-2-yl)-5-methylpyrimidine-2,4(1H,3H)-dione,
((2R,3R,4R,5R)-3-acetoxy-5-(6-(cyclopropylmethylamino)-9H-purin-9-yl)-4-fluoro-3,4-dimethyltetrahydrofuran-2-yl)methyl benzoate,
((2R,3R,4R,5S)-3-acetoxy-5-(6-(cyclopropylmethylamino)-9H-purin-9-yl)-4-fluoro-3,4-dimethyltetrahydrofuran-2-yl)methyl benzoate,
((2R,3S,4R,5R)-3-acetoxy-5-(6-(cyclopropylmethylamino)-9H-purin-9-yl)-4-fluoro-3,4-dimethyltetrahydrofuran-2-yl)methyl benzoate,
((2R,3S,4R,5S)-3-acetoxy-5-(6-(cyclopropylmethylamino)-9H-purin-9-yl)-4-fluoro-3,4-dimethyltetrahydrofuran-2-yl)methyl benzoate,
((2R,3R,4R,5R)-3-acetoxy-5-(2-amino-6-chloro-9H-purin-9-yl)-4-fluoro-3,4-dimethyltetrahydrofuran-2-yl)methyl benzoate,
((2R,3R,4R,5S)-3-acetoxy-5-(2-amino-6-chloro-9H-purin-9-yl)-4-fluoro-3,4-dimethyltetrahydrofuran-2-yl)methyl benzoate,
((2R,3S,4R,5R)-3-acetoxy-5-(2-amino-6-chloro-9H-purin-9-yl)-4-fluoro-3,4-dimethyltetrahydrofuran-2-yl)methyl benzoate,
((2R,3S,4R,5S)-3-acetoxy-5-(2-amino-6-chloro-9H-purin-9-yl)-4-fluoro-3,4-dimethyltetrahydrofuran-2-yl)methyl benzoate,
(2R,3R,4R,5R)-5-(6-(cyclopentylamino)-9H-purin-9-yl)-4-fluoro-2-(hydroxymethyl)-3,4-dimethyltetrahydrofuran-3-ol,
(2R,3R,4R,5S)-5-(6-(cyclopentylamino)-9H-purin-9-yl)-4-fluoro-2-(hydroxymethyl)-3,4-dimethyltetrahydrofuran-3-ol,
(2R,3S,4R,5R)-5-(6-(cyclopentylamino)-9H-purin-9-yl)-4-fluoro-2-(hydroxymethyl)-3,4-dimethyltetrahydrofuran-3-ol,
(2R,3S,4R,5S)-5-(6-(cyclopentylamino)-9H-purin-9-yl)-4-fluoro-2-(hydroxymethyl)-3,4-dimethyltetrahydrofuran-3-ol,
(2R,3R,4R,5R)-5-(6-(cyclohexylamino)-9H-purin-9-yl)-4-fluoro-2-(hydroxymethyl)-3,4-dimethyltetrahydrofuran-3-ol,
(2R,3R,4R,5S)-5-(6-(cyclohexylamino)-9H-purin-9-yl)-4-fluoro-2-(hydroxymethyl)-3,4-dimethyltetrahydrofuran-3-ol,
(2R,3S,4R,5R)-5-(6-(cyclohexylamino)-9H-purin-9-yl)-4-fluoro-2-(hydroxymethyl)-3,4-dimethyltetrahydrofuran-3-ol, (2R,3S,4R,5S)-5-(6-(cyclohexylamino)-9H-purin-9-yl)-4-fluoro-2-(hydroxymethyl)-3,4-dimethyltetrahydrofuran-3-ol, ((2R,3R,4R,5R)-3-acetoxy-5-(6-(benzylamino)-9H-purin-9-yl)-4-fluoro-3,4-dimethyltetrahydrofuran-2-yl)methyl benzoate, ((2R,3R,4R,5S)-3-acetoxy-5-(6-(benzylamino)-9H-purin-9-yl)-4-fluoro-3,4-dimethyltetrahydrofuran-2-yl)methyl benzoate, ((2R,3S,4R,5R)-3-acetoxy-5-(6-(benzylamino)-9H-purin-9-yl)-4-fluoro-3,4-dimethyltetrahydrofuran-2-yl)methyl benzoate, ((2R,3S,4R,5S)-3-acetoxy-5-(6-(benzylamino)-9H-purin-9-yl)-4-fluoro-3,4-dimethyltetrahydrofuran-2-yl)methyl benzoate, (2R,3R,4R,5R)-5-(6-(cyclopropylmethylamino)-9H-purin-9-yl)-4-fluoro-2-(hydroxymethyl)-3,4-dimethyltetrahydrofuran-3-ol, (2R,3R,4R,5S)-5-(6-(cyclopropylmethylamino)-9H-purin-9-yl)-4-fluoro-2-(hydroxymethyl)-3,4-dimethyltetrahydrofuran-3-ol, (2R,3S,4R,5R)-5-(6-(cyclopropylmethylamino)-9H-purin-9-yl)-4-fluoro-2-(hydroxymethyl)-3,4-dimethyltetrahydrofuran-3-ol, (2R,3S,4R,5S)-5-(6-(cyclopropylmethylamino)-9H-purin-9-yl)-4-fluoro-2-(hydroxymethyl)-3,4-dimethyltetrahydrofuran-3-ol, ((2R,3R,4R,5R)-5-(2,4-dioxo-3,4-dihydropyrimidin-1(2H)-yl)-4-fluoro-3-hydroxy-3,4-dimethyltetrahydrofuran-2-yl)methyl butyrate, ((2R,3R,4R,5S)-5-(2,4-dioxo-3,4-dihydropyrimidin-1(2H)-yl)-4-fluoro-3-hydroxy-3,4-dimethyltetrahydrofuran-2-yl)methyl butyrate, ((2R,3S,4R,5R)-5-(2,4-dioxo-3,4-dihydropyrimidin-1(2H)-yl)-4-fluoro-3-hydroxy-3,4-dimethyltetrahydrofuran-2-yl)methyl butyrate, ((2R,3S,4R,5S)-5-(2,4-dioxo-3,4-dihydropyrimidin-1(2H)-yl)-4-fluoro-3-hydroxy-3,4-dimethyltetrahydrofuran-2-yl)methyl butyrate, ((2R,3R,4R,5R)-5-(2,4-dioxo-3,4-dihydropyrimidin-1(2H)-yl)-4-fluoro-3-hydroxy-3,4-dimethyltetrahydrofuran-2-yl)methyl pentanoate, ((2R,3R,4R,5S)-5-(2,4-dioxo-3,4-dihydropyrimidin-1(2H)-yl)-4-fluoro-3-hydroxy-3,4-dimethyltetrahydrofuran-2-yl)methyl pentanoate, ((2R,3S,4R,5R)-5-(2,4-dioxo-3,4-dihydropyrimidin-1(2H)-yl)-4-fluoro-3-hydroxy-3,4-dimethyltetrahydrofuran-2-yl)methyl pentanoate, ((2R,3S,4R,5S)-5-(2,4-dioxo-3,4-dihydropyrimidin-1(2H)-yl)-4-fluoro-3-hydroxy-3,4-dimethyltetrahydrofuran-2-yl)methyl pentanoate, ((2R,3R,4R,5R)-3-acetoxy-4-fluoro-3,4-dimethyl-5-(6-oxo-1H-purin-9(6H)-yl)tetrahydrofuran-2-yl)methyl benzoate, ((2R,3R,4R,5S)-3-acetoxy-4-fluoro-3,4-dimethyl-5-(6-oxo-1H-purin-9(6H)-yl)tetrahydrofuran-2-yl)methyl benzoate, ((2R,3S,4R,5R)-3-acetoxy-4-fluoro-3,4-dimethyl-5-(6-oxo-1H-purin-9(6H)-yl)tetrahydrofuran-2-yl)methyl benzoate, ((2R,3S,4R,5S)-3-acetoxy-4-fluoro-3,4-dimethyl-5-(6-oxo-1H-purin-9(6H)-yl)tetrahydrofuran-2-yl)methyl benzoate, 9-((2R,3R,4R,5R)-3-fluoro-4-hydroxy-5-(hydroxymethyl)-3,4-dimethyltetrahydrofuran-2-yl)-1H-purin-6(9H)-one, 9-((2R,3R,4S,5R)-3-fluoro-4-hydroxy-5-(hydroxymethyl)-3,4-dimethyltetrahydrofuran-2-yl)-1H-purin-6(9H)-one, 9-((2S,3R,4R,5R)-3-fluoro-4-hydroxy-5-(hydroxymethyl)-3,4-dimethyltetrahydrofuran-2-yl)-1H-purin-6(9H)-one, 9-((2S,3R,4S,5R)-3-fluoro-4-hydroxy-5-(hydroxymethyl)-3,4-dimethyltetrahydrofuran-2-yl)-1H-purin-6(9H)-one, ((2R,3R,4R,5R)-3-acetoxy-4-fluoro-3,4-dimethyl-5-(5-methyl-2,4-dioxo-3,4-dihydropyrimidin-1(2H)-yl)tetrahydrofuran-2-yl)methyl benzoate, ((2R,3R,4R,5S)-3-acetoxy-4-fluoro-3,4-dimethyl-5-(5-methyl-2,4-dioxo-3,4-dihydropyrimidin-1(2H)-yl)tetrahydrofuran-2-yl)methyl benzoate, ((2R,3S,4R,5R)-3-acetoxy-4-fluoro-3,4-dimethyl-5-(5-methyl-2,4-dioxo-3,4-dihydropyrimidin-1(2H)-yl)tetrahydrofuran-2-yl)methyl benzoate, ((2R,3S,4R,5S)-3-acetoxy-4-fluoro-3,4-dimethyl-5-(5-methyl-2,4-dioxo-3,4-dihydropyrimidin-1(2H)-yl)tetrahydrofuran-2-yl)methyl benzoate, ((2R,3R,4R,5R)-5-(2,4-dioxo-3,4-dihydropyrimidin-1(2H)-yl)-4-fluoro-3-hydroxy-3,4-dimethyltetrahydrofuran-2-yl)methyl isobutyrate, ((2R,3R,4R,5S)-5-(2,4-dioxo-3,4-dihydropyrimidin-1(2H)-yl)-4-fluoro-3-hydroxy-3,4-dimethyltetrahydrofuran-2-yl)methyl isobutyrate, ((2R,3S,4R,5R)-5-(2,4-dioxo-3,4-dihydropyrimidin-1(2H)-yl)-4-fluoro-3-hydroxy-3,4-dimethyltetrahydrofuran-2-yl)methyl isobutyrate, ((2R,3S,4R,5S)-5-(2,4-dioxo-3,4-dihydropyrimidin-1(2H)-yl)-4-fluoro-3-hydroxy-3,4-dimethyltetrahydrofuran-2-yl)methyl isobutyrate, (2R,3R,4R,5R)-4-fluoro-2-(hydroxymethyl)-3,4-dimethyl-5-(6-morpholino-9H-purin-9-yl)tetrahydrofuran-3-ol, (2R,3R,4R,5S)-4-fluoro-2-(hydroxymethyl)-3,4-dimethyl-5-(6-morpholino-9H-purin-9-yl)tetrahydrofuran-3-ol, (2R,3S,4R,5R)-4-fluoro-2-(hydroxymethyl)-3,4-dimethyl-5-(6-morpholino-9H-purin-9-yl)tetrahydrofuran-3-ol, (2R,3S,4R,5S)-4-fluoro-2-(hydroxymethyl)-3,4-dimethyl-5-(6-morpholino-9H-purin-9-yl)tetrahydrofuran-3-ol, ((2R,3R,4R,5R)-3-acetoxy-4-fluoro-5-(5-fluoro-2,4-dioxo-3,4-dihydropyrimidin-1(2H)-yl)-3,4-dimethyltetrahydrofuran-2-yl)methyl benzoate, ((2R,3R,4R,5S)-3-acetoxy-4-fluoro-5-(5-fluoro-2,4-dioxo-3,4-dihydropyrimidin-1(2H)-yl)-3,4-dimethyltetrahydrofuran-2-yl)methyl benzoate, ((2R,3S,4R,5R)-3-acetoxy-4-fluoro-5-(5-fluoro-2,4-dioxo-3,4-dihydropyrimidin-1(2H)-yl)-3,4-dimethyltetrahydrofuran-2-yl)methyl benzoate, ((2R,3S,4R,5S)-3-acetoxy-4-fluoro-5-(5-fluoro-2,4-dioxo-3,4-dihydropyrimidin-1(2H)-yl)-3,4-dimethyltetrahydrofuran-2-yl)methyl benzoate, 5-fluoro-1-((2R,3R,4R,5R)-3-fluoro-4-hydroxy-5-(hydroxymethyl)-3,4-dimethyltetrahydrofuran-2-yl)pyrimidine-2,4(1H,3H)-dione, 5-fluoro-1-((2R,3R,4S,5R)-3-fluoro-4-hydroxy-5-(hydroxymethyl)-3,4-dimethyltetrahydrofuran-2-yl)pyrimidine-2,4(1H,3H)-dione, 5-fluoro-1-((2S,3R,4R,5R)-3-fluoro-4-hydroxy-5-(hydroxymethyl)-3,4-dimethyltetrahydrofuran-2-yl)pyrimidine-2,4(1H,3H)-dione, 5-fluoro-1-((2S,3R,4S,5R)-3-fluoro-4-hydroxy-5-(hydroxymethyl)-3,4-dimethyltetrahydrofuran-2-yl)pyrimidine-2,4(1H,3H)-dione, ((2R,3R,4R,5R)-4-fluoro-3-hydroxy-3,4-dimethyl-5-(6-morpholino-9H-purin-9-yl)tetrahydrofuran-2-yl)methyl pentanoate, ((2R,3R,4R,5S)-4-fluoro-3-hydroxy-3,4-dimethyl-5-(6-morpholino-9H-purin-9-yl)tetrahydrofuran-2-yl)methyl pentanoate, ((2R,3S,4R,5R)-4-fluoro-3-hydroxy-3,4-dimethyl-5-(6-morpholino-9H-purin-9-yl)tetrahydrofuran-2-yl)methyl pentanoate,
((2R,3S,4R,5S)-4-fluoro-3-hydroxy-3,4-dimethyl-5-(6-morpholino-9H-purin-9-yl)tetrahydrofuran-2-yl)methyl pentanoate,
((2R,3R,4R,5R)-4-fluoro-3-hydroxy-3,4-dimethyl-5-(6-morpholino-9H-purin-9-yl)tetrahydrofuran-2-yl)methyl butyrate,
((2R,3R,4R,5S)-4-fluoro-3-hydroxy-3,4-dimethyl-5-(6-morpholino-9H-purin-9-yl)tetrahydrofuran-2-yl)methyl butyrate,
((2R,3S,4R,5R)-4-fluoro-3-hydroxy-3,4-dimethyl-5-(6-morpholino-9H-purin-9-yl)tetrahydrofuran-2-yl)methyl butyrate,
((2R,3S,4R,5S)-4-fluoro-3-hydroxy-3,4-dimethyl-5-(6-morpholino-9H-purin-9-yl)tetrahydrofuran-2-yl)methyl butyrate,
((2R,3R,4R,5R)-4-fluoro-3-hydroxy-3,4-dimethyl-5-(6-morpholino-9H-purin-9-yl)tetrahydrofuran-2-yl)methyl isobutyrate,
((2R,3R,4R,5S)-4-fluoro-3-hydroxy-3,4-dimethyl-5-(6-morpholino-9H-purin-9-yl)tetrahydrofuran-2-yl)methyl isobutyrate,
((2R,3S,4R,5R)-4-fluoro-3-hydroxy-3,4-dimethyl-5-(6-morpholino-9H-purin-9-yl)tetrahydrofuran-2-yl)methyl isobutyrate,
((2R,3S,4R,5S)-4-fluoro-3-hydroxy-3,4-dimethyl-5-(6-morpholino-9H-purin-9-yl)tetrahydrofuran-2-yl)methyl isobutyrate,
(2R,3R,4R,5R)-5-(6-(3-chlorobenzylamino)-9H-purin-9-yl)-4-fluoro-2-(hydroxymethyl)-3,4-dimethyltetrahydrofuran-3-ol,
(2R,3R,4R,5S)-5-(6-(3-chlorobenzylamino)-9H-purin-9-yl)-4-fluoro-2-(hydroxymethyl)-3,4-dimethyltetrahydrofuran-3-ol,
(2R,3S,4R,5R)-5-(6-(3-chlorobenzylamino)-9H-purin-9-yl)-4-fluoro-2-(hydroxymethyl)-3,4-dimethyltetrahydrofuran-3-ol,
(2R,3S,4R,5S)-5-(6-(3-chlorobenzylamino)-9H-purin-9-yl)-4-fluoro-2-(hydroxymethyl)-3,4-dimethyltetrahydrofuran-3-ol,
(2R,3R,4R,5R)-4-fluoro-5-(6-(furan-2-ylmethylamino)-9H-purin-9-yl)-2-(hydroxymethyl)-3,4-dimethyltetrahydrofuran-3-ol,
(2R,3R,4R,5S)-4-fluoro-5-(6-(furan-2-ylmethylamino)-9H-purin-9-yl)-2-(hydroxymethyl)-3,4-dimethyltetrahydrofuran-3-ol,
(2R,3S,4R,5R)-4-fluoro-5-(6-(furan-2-ylmethylamino)-9H-purin-9-yl)-2-(hydroxymethyl)-3,4-dimethyltetrahydrofuran-3-ol,
(2R,3S,4R,5S)-4-fluoro-5-(6-(furan-2-ylmethylamino)-9H-purin-9-yl)-2-(hydroxymethyl)-3,4-dimethyltetrahydrofuran-3-ol,
(2R,3R,4R,5R)-5-(6-(2-chlorobenzylamino)-9H-purin-9-yl)-4-fluoro-2-(hydroxymethyl)-3,4-dimethyltetrahydrofuran-3-ol,
(2R,3R,4R,5S)-5-(6-(2-chlorobenzylamino)-9H-purin-9-yl)-4-fluoro-2-(hydroxymethyl)-3,4-dimethyltetrahydrofuran-3-ol,
(2R,3S,4R,5R)-5-(6-(2-chlorobenzylamino)-9H-purin-9-yl)-4-fluoro-2-(hydroxymethyl)-3,4-dimethyltetrahydrofuran-3-ol,
(2R,3S,4R,5S)-5-(6-(2-chlorobenzylamino)-9H-purin-9-yl)-4-fluoro-2-(hydroxymethyl)-3,4-dimethyltetrahydrofuran-3-ol,
(2R,3R,4R,5R)-5-(6-(cyclobutylamino)-9H-purin-9-yl)-4-fluoro-2-(hydroxymethyl)-3,4-dimethyltetrahydrofuran-3-ol,
(2R,3R,4R,5S)-5-(6-(cyclobutylamino)-9H-purin-9-yl)-4-fluoro-2-(hydroxymethyl)-3,4-dimethyltetrahydrofuran-3-ol,
(2R,3S,4R,5R)-5-(6-(cyclobutylamino)-9H-purin-9-yl)-4-fluoro-2-(hydroxymethyl)-3,4-dimethyltetrahydrofuran-3-ol,
(2R,3S,4R,5S)-5-(6-(cyclobutylamino)-9H-purin-9-yl)-4-fluoro-2-(hydroxymethyl)-3,4-dimethyltetrahydrofuran-3-ol,
(2S)-((2R,3R,4R,5R)-4-fluoro-3-hydroxy-3,4-dimethyl-5-(5-methyl-2,4-dioxo-3,4-dihydropyrimidin-1(2H)-yl)tetrahydrofuran-2-yl)methyl 2-(tert-butoxycarbonylamino)propanoate,
(2S)-((2R,3R,4R,5S)-4-fluoro-3-hydroxy-3,4-dimethyl-5-(5-methyl-2,4-dioxo-3,4-dihydropyrimidin-1(2H)-yl)tetrahydrofuran-2-yl)methyl 2-(tert-butoxycarbonylamino)propanoate,
(2S)-((2R,3S,4R,5R)-4-fluoro-3-hydroxy-3,4-dimethyl-5-(5-methyl-2,4-dioxo-3,4-dihydropyrimidin-1(2H)-yl)tetrahydrofuran-2-yl)methyl 2-(tert-butoxycarbonylamino)propanoate,
(2S)-((2R,3S,4R,5S)-4-fluoro-3-hydroxy-3,4-dimethyl-5-(5-methyl-2,4-dioxo-3,4-dihydropyrimidin-1(2H)-yl)tetrahydrofuran-2-yl)methyl 2-(tert-butoxycarbonylamino)propanoate,
((2R,3R,4R,5R)-4-fluoro-3-hydroxy-3,4-dimethyl-5-(5-methyl-2,4-dioxo-3,4-dihydropyrimidin-1(2H)-yl)tetrahydrofuran-2-yl)methyl 2-aminopropanoate,
((2R,3R,4R,5S)-4-fluoro-3-hydroxy-3,4-dimethyl-5-(5-methyl-2,4-dioxo-3,4-dihydropyrimidin-1(2H)-yl)tetrahydrofuran-2-yl)methyl 2-aminopropanoate,
((2R,3S,4R,5R)-4-fluoro-3-hydroxy-3,4-dimethyl-5-(5-methyl-2,4-dioxo-3,4-dihydropyrimidin-1(2H)-yl)tetrahydrofuran-2-yl)methyl 2-aminopropanoate,
((2R,3S,4R,5S)-4-fluoro-3-hydroxy-3,4-dimethyl-5-(5-methyl-2,4-dioxo-3,4-dihydropyrimidin-1(2H)-yl)tetrahydrofuran-2-yl)methyl 2-aminopropanoate,
pharmaceutically acceptable salts, solvates, including hydrates and prodrugs of compounds are also contemplated.

The present patent application also provides a pharmaceutical composition that includes at least one compound of described herein and at least one pharmaceutically acceptable excipient (such as a pharmaceutically acceptable carrier or diluent). Preferably, the pharmaceutical composition comprises a therapeutically effective amount of at least one compound described herein. The compound(s) present in the composition may be associated with a pharmaceutically acceptable excipient (such as a carrier or a diluent) or may be diluted by a carrier, or enclosed within a carrier which may be in the form of a capsule, sachet, paper or other container.

The compounds and pharmaceutical compositions described herein are useful in the treatment of diseases, conditions and/or disorders mediated by viral infections.

The present patent application further provides a method of treating a disease, condition and/or disorder mediated by viral infections in a subject in need thereof by administering to the subject one or more compounds described herein in the amount effective to cause that infection.

Also provided herein are processes for preparing compounds described herein.

The invention provides a method for preventing, ameliorating or treating a viral mediated disease, disorder or syndrome in a subject in need thereof comprising administering to the subject a therapeutically effective amount of a compound of the invention. The invention further provides a method, wherein the viral mediated disease, disorder or syndrome is HIV infection, HBV, HCV, a retroviral infection genetically related to AIDS, respiratory disorders (including adult respiratory distress syndrome (ARDS)), and inflammatory disease. The invention further provides a method, wherein the disease, disorder or syndrome is selected from the group consisting of HIV infection, HBV, HCV, a retroviral infection genetically related to HIV, AIDS, inflammatory disease, respiratory disorders (including adult respiratory distress syndrome (ARDS), bronchitis, chronic bronchitis, chronic obstructive pulmonary disease, cystic fibrosis, asthma, emphysema, rhinitis and chronic sinusitis), inflammatory bowel disease (including Crohn's disease and ulcerative colitis), multiple sclerosis, rheumatoid arthritis, graft rejection, endometriosis, type I diabetes, renal diseases, chronic pancreatitis, inflammatory lung conditions, chronic heart failure and bacterial infections.

The invention provides a method of treating HCV in a subject in need thereof comprising administering to the subject a therapeutically effective amount of a compound according to the invention. A number of assays have been published in the literature to assess the anti HCV activity of the compounds. For example, in-vitro assays have been reported in Ferrary et. al., *journal of Virology*, 73, 1649-54, 1999; Ishii et. al., *Hepatology*, 29, 1227-35, 1999, Lohmannn, et. al., *journal of Biological Chemistry*, 274, 10807-815, 1999; and Yamashita et. al., *journal Biologiocal chemistry*, 273, 15479-486, 1998. Other relevant informatic assays published in WO 97/12033 and *Anti viral therapy*, 1996, 1 (supp 4), 18-24.

The invention provides a method of treating HBV in a subject in need thereof comprising administering to the subject a therapeutically effective amount of a compound according to the invention.

The invention provides a method of treating bacterial infection in a subject in need thereof comprising administering to the subject a therapeutically effective amount of a compound according to the invention.

The invention provides a process for the preparation of a compound of formula (II):

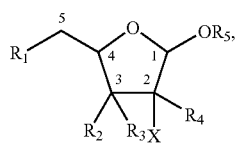

II wherein $R^4$ and X are as defined above, which process comprises the steps of (a) reducing the compounds of formula (A) with a reducing agent

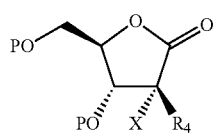

A to form a compound of formula (B)

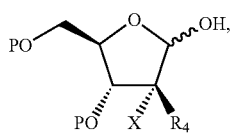

B (b) converting the compounds of formula (B) to the compounds of formula (C) and (D) by reacting with protecting agent

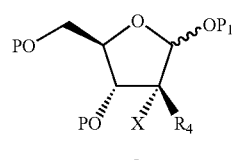

C

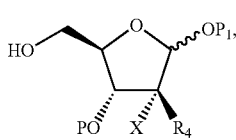

D (c) deprotecting the compounds of formula (C) and/or (D) under selective deprotecting conditions to form a compound of formula (E)

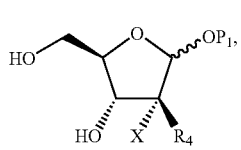

E (d) protecting the primary hydroxyl group of the compounds of formula (E) with a protecting agent to form a compound of formula (F),

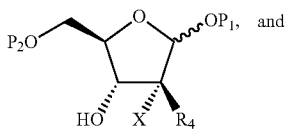

F (e) oxidising the compounds of formula (F) with an oxidising agent to form a compound of formula G

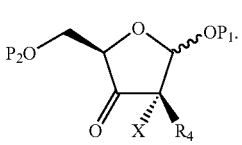

G

The invention provides a process for the preparation of a compound of formula (I):

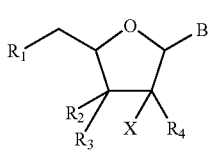

Formula (I)

wherein,

B is Nitrogen heterocycle of from C3 to C15, such as optionally substituted purine, pyrimidine, pyridine, pyrrole, indole, imidazole, pyrazole, quinazoline, pyridizine, pyrezine, cinnoline, phthalazin, quinoxaline, xanthine, hypoxanthine, adenine, guanine, cytosine, uracil, thymine, pteridine, 5-azacytidine, 5-azauracil, triazolopyridine, imidazolopyridine, imidazolotriazine, pyrrolopyrimidine, pyrazolopyrimidine; the heterocycle may be bound to the sugar moiety in the nucleoside through any available atom including ring nitrogen or ring carbon atom;

X can be halogen;

$R_4$ can be alkyl group;

$R_2$ and $R_3$ independently are selected from OH, alkyl, alkenyl, halogen, alkynyl, cycloalkyl, $N_3$, $CF_3$, $NH_2$, $NH_2$, RCONHCH(Ra)C(O)O, $NH_2CH(R^a)C(O)O$ (wherein $R^a$ can be H, alkyl, or benezyl) or CN; $R_2$ and $R_3$ can be together form oxo (=O) group;

$R_1$ is H, OH, —{P(O(OH)O-}nR, alkyl, hydrogen, acyl, aryl, alkyl carbonyloxy, aryl carbonyloxy, silyl, RCONHCH(Ra)C(O)O, $NH_2CH(R^a)C(O)O$ (wherein $R^a$ can be H, alkyl or benezyl), heterocycloalkyl, or sulfonyl;

R is alkyl, hydrogen, acyl, aryl, alkyl carbonyloxy, aryl carbonyloxy, or heterocycloalkyl;

$R_1$, $R_2$, $R_3$, $R_4$, and R independently are further substituted wherever appropriate by a group like halogen, alkyl, alkenyl, alkynyl, aryl, alkylaryl, aralkyl, cycloalkyl, heterocyclyl, heterocycloakyl, hydroxy, amino, cyano, azido, carbonyl, oxycarbonyl, sulfonyl, sulfonyloxy, or carbonyloxy, an analog thereof, a pharmaceutically acceptable salt thereof, a pharmaceutically acceptable solvate thereof, a pharmaceutically acceptable hydrate thereof, an N-oxide thereof, a tautomer thereof, a regioisomer thereof, a stereoisomer thereof, a prodrug thereof or a polymorph thereof, the process comprising the steps of:

(a) reacting the compounds of formula (G)

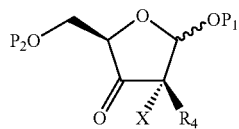

with $R_2$—MgX to form a compound of formula (H)

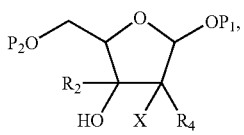

(b) deprotecting the $P_2$ group of the compounds of formula (H) to form a compound of formula (J)

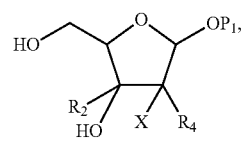

(c) reacting the compounds of formula (J) with $R_1/R_3$—Cl to form a compound of formula (K)

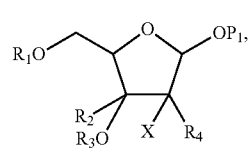

(d) deprotecting the $P_1$ group of the compounds of formula (K) followed by reacting with a suitable reagent (L is leaving group such as, O-acyl or O-silyl) to form a compound of formula (L)

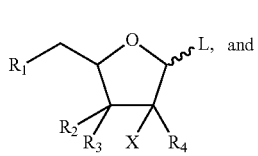

(e) treating the compounds of formula (L) with suitable base (B) (wherein, B is optionally substituted purine, pyrimidine, uracil, thiamine and cytosine) to form a compound of formula (I) in the presence of suitable coupling agent.

The invention provides a process for the preparation of compounds of formula a and a':

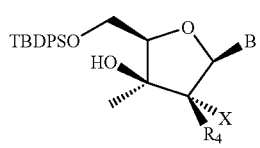

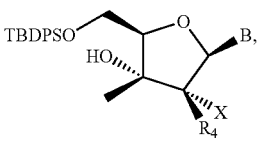

wherein,

B is Nitrogen heterocycle of from C3 to C15, such as optionally substituted purine, pyrimidine, pyridine, pyrrole, indole, imidazole, pyrazole, quinazoline, pyridizine, pyrezine, cinnoline, phthalazin, quinoxaline, xanthine, hypoxanthine, adenine, guanine, cytosine, uracil, thymine, pteridine, 5-azacytidine, 5-azauracil, triazolopyridine, imidazolopyridine, imidazolotriazine, pyrrolopyrimidine, pyrazolopyrimidine; the heterocycle may be bound to the sugar moiety in the nucleoside through any available atom including ring nitrogen or ring carbon atom;

X can be halogen;

$R_4$ can be alkyl group;

the process comprising the steps of:

(a) reducing the compound of formula (G):

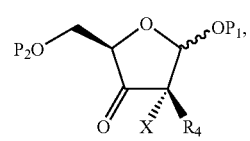

to form diastereomers of compounds of formulae T and U:

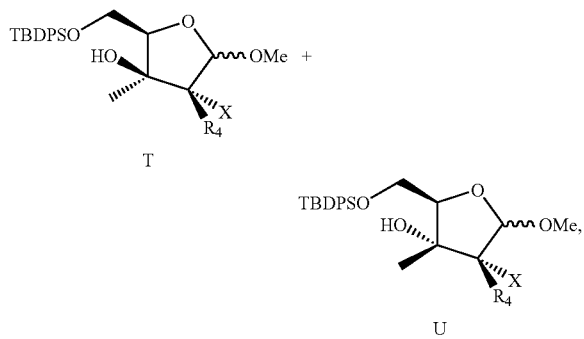

(b) demethylating the compounds of formulae T and U to form respectively hydroxy compounds of formulae W and X in one or more base:

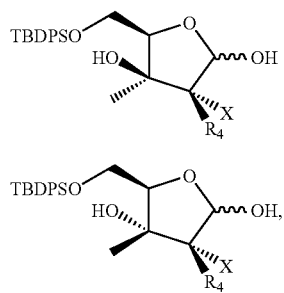

(c) treating hydroxy compounds of formulae W and X for selective protection to form respectively selective protected compounds of formulae Y and Z in one or more protecting groups and one or more base and one or more solvent:

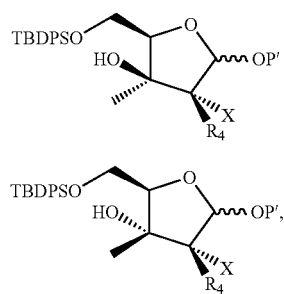

(d) reacting selective protected compounds of formulae Y and Z with suitable bases (B, for example, optionally substituted purine and pyrimidine) to form compounds of formulae a and a' in one or more coupling reagent and one or more solvent.

The invention provides pharmaceutical salts of the compounds of the invention wherein the salt is, for example, (a) an inorganic acid addition salt selected from hydrochloride, sulphate, phosphate and nitrate, or (b) an organic acid addition salt selected from acetate, oxalate, maleate, tartarate, citrate, mesylate, succinate, and cinnamate.

The invention provides pharmaceutical compositions comprising a compound according to the invention and a pharmaceutically acceptable excipient.

DETAILED DESCRIPTION OF THE INVENTION

The present patent application provides nucleoside derivatives, which may be used as antivirals and processes for the synthesis of these compounds. Pharmaceutically acceptable salts, pharmaceutically acceptable solvates, enantiomers, diastereomers, together with pharmaceutically acceptable carriers, excipients or diluents, which can be used for the treatment of diseases, condition and/or disorders mediated by viral infections, are also provided.

The Following Definitions Apply to the Terms as Used Herein

The terms "halogen" or "halo" includes fluorine, chlorine, bromine, or iodine.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl(isopropyl), n-butyl, n-pentyl, and 1,1-dimethylethyl (t-butyl).

The term "alkenyl" refers to an aliphatic hydrocarbon group containing a carbon-carbon double bond and which may be a straight or branched chain having from 2 to about 10 carbon atoms, e.g., ethenyl, 1-propenyl, 2-propenyl(allyl), iso-propenyl, 2-methyl-1-propenyl, 1-butenyl, and 2-butenyl.

The term "haloalkyl" is used to denote a group comprised of an alkyl group substituted with halogen atom, where alkyl group is as defined above and halogen is used to denote fluorine, chlorine, bromine or iodine, an example of such group is trifluoromethyl, difluoromethyl.

The term "acyl group" is used to denote a linear or branched aliphatic acyl group (preferably a $C_{2-6}$ alkanoyl group) or an aromatic acyl group, which contains 2 to 10 carbon atoms. Examples include an acetyl group, a propionyl group, a pivaloyl group, a butyryl group, an isobutyryl group, a valeryl group and a benzoyl group, with an acetyl group being preferred.

The term "alkoxy group" is used to denote a linear or branched alkoxy group containing 1 to 6 carbon atoms. Preferred are $C_{1-4}$ alkoxy groups including a methoxy group, an ethoxy group, a propoxy group, an isopropoxy group, a n-butoxy group, an isobutoxy group and a tert-butoxy group.

The term "alkoxycarbonyl group" is used to denote a structure composed of a linear or branched $C_{1-5}$ alkoxy group and a carbonyl group. Preferred are $C_{2-5}$ alkoxycarbonyl groups including a methoxycarbonyl group, an ethoxycarbonyl group, a propoxycarbonyl group, an isopropoxycarbonyl group and a butoxycarbonyl group. Among them, a methoxycarbonyl group is preferred.

The term "cycloalkyl" denotes a non-aromatic mono or multicyclic ring system of from 3 to about 12 carbon atoms, such as cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups and spirobicyclic groups, e.g., spiro (4,4) non-2-yl.

The term "cycloalkylalkyl" refers to a cyclic ring-containing radical having from 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl.

The term "cycloalkenyl" refers to a cyclic ring-containing radical having from 3 to about 8 carbon atoms with at least one carbon-carbon double bond, such as cyclopropenyl, cyclobutenyl, and cyclopentenyl.

The term "aryl" refers to an aromatic radical having from 6 to 14 carbon atoms such as phenyl, naphthyl, tetrahydronapthyl, indanyl, and biphenyl.

The term "arylalkyl" refers to an aryl group as defined above directly bonded to an alkyl group as defined above, e.g., —CH$_2$C$_6$H$_5$ and —C$_2$H$_5$C$_6$H$_5$.

"Substituted" refers to 1-3 substituents on the same position or on different positions with the same groups or different groups.

"Alkynyl" refers to alkynyl groups having from 2 to 6 carbon atoms and having at least one alkynyl saturation, example for such group includes acetylenyl, propargyl.

"Carbonyloxy" refers to a group such as —C(O)O.

"Silyl" refers to a group such as trimethylsilyl, triethylsilyl, triisopropylsilyl, dimethylisopropylsilyl, diethylisopropylsilyl, t-butyldimethylsilyl.

"sulfonyl", "sulfonyloxy" refers to the groups —SO2R6, where R6 is selected from the groups consisting of alkyl, aryl, heteroaryl, heterocyclyl.

"P{(O)(OH)O-}n R" refers to the groups —P(O)(OH)2, —P(O)(OH)OP(O)(OH)2 and —P(O)(OH)OP(O)(OH)OP(O)(OH)2 and also groups including R represents alkyl or aryl.

The terms "heterocyclyl" and "heterocyclic ring" refer to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, azetidinyl, acridinyl, carbazolyl, cinnolinyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl. The heterocyclic ring radical may be attached to the main structure at any heteroatom or carbon atom that results in the creation of a stable structure.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure.

The term "heteroaryl" refers to an aromatic heterocyclic ring radical. The heteroaryl ring radical may be attached to the main structure at any heteroatom or carbon atom that results in the creation of a stable structure.

The term "heteroarylalkyl" refers to a heteroaryl ring radical directly bonded to an alkyl group. The heteroarylalkyl radical may be attached to the main structure at any carbon atom in the alkyl group that results in the creation of a stable structure.

Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, haloalkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —COOR$^x$, —C(O)R$^x$, —C(S)R$^x$, —C(O)NR$^x$R$^y$, —C(O)ONR$^x$R$^y$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$, —NR$^x$C(S)R$^y$, —NR$^x$C(S)NR$^y$R$^z$, —SONR$^x$R$^y$, —SO$_2$NR$^x$R$^y$, —OR$^x$, —OR$^x$C(O)NR$^y$R$^z$, —OR$^x$C(O)OR$^y$, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^y$, —R$^x$OC(O)R$^y$, —SR$^x$, —SOR$^x$, —SO$_2$R$^x$, and —ONO$_2$, wherein R$^x$, R$^y$ and R$^z$ are independently selected from hydrogen, substituted or unsubstituted alkyl, haloalkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. The substituents in the aforementioned "substituted" groups cannot be further substituted. For example, when the substituent on "substituted alkyl" is "substituted aryl", the substituent on "substituted aryl" cannot be "substituted alkenyl".

The term "prodrug" means a compound that is transformed in vivo to yield a compound of Formula (I) (II) or (IIA) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "treating" or "treatment" of a state, disease, disorder or condition includes:

(1) preventing or delaying the appearance of clinical symptoms of the state, disease, disorder or condition developing in a subject that may be afflicted with or predisposed to the state, disease, disorder or condition but does not yet experience or display clinical or subclinical symptoms of the state, disease, disorder or condition;

(2) inhibiting the state, disease, disorder or condition, i.e., arresting or reducing the development of the state, disease, disorder or condition or at least one clinical or subclinical symptom thereof; or (3) relieving the state, disease, disorder or condition, i.e., causing regression of the state, disease, disorder or condition or at least one of its clinical or subclinical symptoms.

The benefit to a subject receiving treatment is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disease, disorder or condition, is sufficient to effect such treatment. The "therapeutically effective amount" will vary depending on the compound, the state, disease, disorder or condition and its severity and the age, weight, physical condition and responsiveness of the subject receiving treatment.

The compound described in the present patent application may form salts. Non-limiting examples of pharmaceutically acceptable salts forming part of this patent application include salts derived from inorganic bases salts of organic bases salts of chiral bases, salts of natural amino acids and salts of non-natural amino acids. Certain compounds of present patent application are capable of existing in stereoisomeric forms (e.g. diastereomers and enantiomers). With respect to the overall compounds described by the Formula (I), the present patent application extends to these stereoisomeric forms and to mixtures thereof. To the extent prior art teaches synthesis or separation of particular stereoisomers, the different stereoisomeric forms of the present patent application may be separated from one another by the method known in the art, or a given isomer may be obtained by stereospecific or asymmetric synthesis. Tautomeric forms and mixtures of compounds described herein are also contemplated.

Pharmaceutically acceptable solvates includes hydrates and other solvents of crystallization (such as alcohols). The compounds of the present invention may form solvates with low molecular weight solvents by methods known in the art.

Pharmaceutical Compositions

The pharmaceutical compositions provided in the present patent application include at least one compound described herein and at least one pharmaceutically acceptable excipient (such as a pharmaceutically acceptable carrier or diluent). Preferably, the contemplated pharmaceutical compositions include a compound(s) described herein in an amount sufficient to treat viral infection in a subject.

The subjects contemplated include, for example, a living cell and a mammal, including human mammal. The compound of the present invention may be associated with a pharmaceutically acceptable excipient (such as a carrier or a diluent) or be diluted by a carrier, or enclosed within a carrier which can be in the form of a capsule, sachet, paper or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as, for example, glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared, e.g., as described in *Remington: The Science and Practice of Pharmacy*, 20$^{th}$ Ed., 2003 (Lippincott Williams & Wilkins). For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be, for example, capsules, tablets, aerosols, solutions, suspensions or products for topical application.

The route of administration may be any route which effectively transports the active compound to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is preferred.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Preferable carriers for tablets, dragees, or capsules include lactose, cornstarch, and/or potato starch. A syrup or elixir can be used in cases where a sweetened vehicle can be employed.

A typical tablet that may be prepared by conventional tabletting techniques may contain: (1) Core: Active compound (as free compound or salt thereof), 250 mg colloidal silicon dioxide (Aerosil®), 1.5 mg microcrystalline cellulose (Avicel®), 70 mg modified cellulose gum (Ac-Di-Sol®), and 7.5 mg magnesium stearate; (2) Coating: HPMC, approx. 9 mg Mywacett 9-40 T and approx. 0.9 mg acylated monoglyceride Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Methods of Treatment

The present invention provides compounds and pharmaceutical formulations thereof that are useful in the treatment of diseases, conditions and/or disorders mediated by viral infections. The connection between therapeutic effect and antiviral is illustrated. For example, PCT publication Nos. WO 01//07646, WO 01/65957, or WO 03/037908; US publication Nos. U.S. Pat. No. 4,598,095 or US 2002/0068757; EP publication Nos. EP0989862 or EP 0724650; *Bioorganic & Medicinal Chemistry Letters*, 16, (6), 1712-1715, 2006, and references cited therein, all of which are incorporated herein by reference in their entirety and for the purpose stated.

The present patent application further provides a method of treating a disease, condition and/or disorder mediated by viral infections in a subject in need thereof by administering to the subject a therapeutically effective amount of a compound or a pharmaceutical composition of the present invention.

may be used as known in the art, are also within the scope of the present invention. All the stereo isomers of the compounds in these schemes, unless otherwise specified, are also encompassed within the scope of this invention.

It will be apparent to those skilled in the art, conventional protecting groups may be necessary to prevent certain functional groups from under going undesired reactions. Suitable conditions for protecting and de protecting particular functional groups are well known in the art. For example, numerous protecting groups are described in T. W. Greene and G. M. Wuts, Protecting groups in Organic Synthesis, Wiley, New York, 1999, and references cited therein.

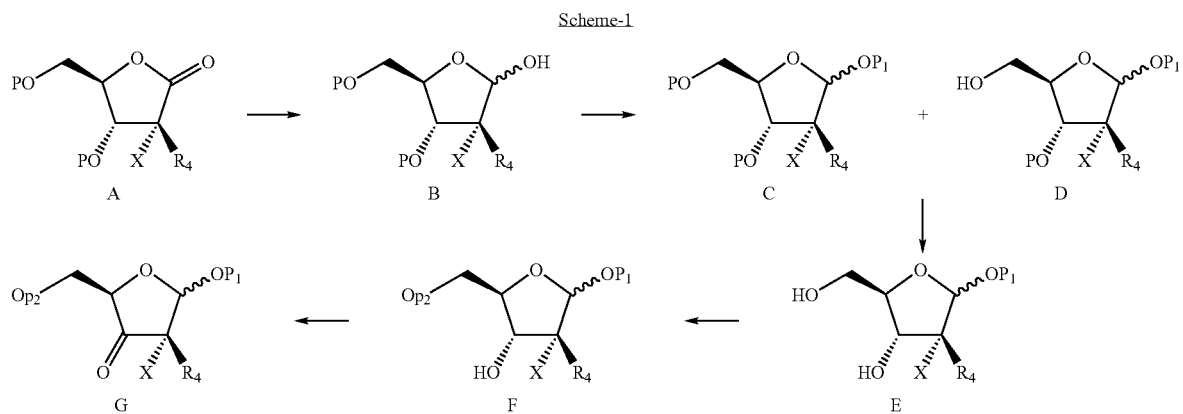

Scheme-1

Diseases, conditions, and/or disorders that are mediated by viral infections are believed to include, but are not limited to, HIV infection, HBV, HCV, a retroviral infection genetically related to HIV, AIDS, inflammatory disease, respiratory disorders (including adult respiratory distress syndrome (ARDS), bronchitis, chronic bronchitis, chronic obstructive pulmonary disease, cystic fibrosis, asthma, emphysema, rhinitis and chronic sinusitis), inflammatory bowel disease (including Crohn's disease and ulcerative colitis), multiple sclerosis, rheumatoid arthritis, graft rejection (in particular but not limited to kidney and lung allografts), endometriosis, type I diabetes, renal diseases, chronic pancreatitis, inflammatory lung conditions, chronic heart failure and bacterial infections (in particular but not limited to tuberculosis).

The compounds of the present invention can obtain more advantageous effects than additive effects in the prevention or treatment of the above diseases when using suitably in combination with the above drugs. Also, the administration dose can be decreased in comparison with administration of either drug alone, or adverse effects of co administrated drugs other than antiviral can be avoided or declined.

Methods of Preparation

The compounds described herein may be prepared by techniques known in the art. In addition, the compounds described herein may be prepared by following the reaction sequence as depicted in Scheme-1 to 3. Further, in the following schemes, where specific bases, acids, reagents, solvents, coupling agents, etc., are mentioned, it is understood that other bases, acids, reagents, solvents, coupling agents etc., known in the art may be used and are therefore included within the present invention. Variations in reaction conditions, for example, temperature and/or duration of the reaction, which The compounds of Formula (G) (wherein, X is a halogen, P is a protecting group (for example, benzoyl or acetyl), $P_1$ is protecting group (for example, alkyl, silyl groups, or sulfonyl group), $P_2$ is protecting group (for example, silyl groups) and $R_4$ is as defined above) can be prepared by the above procedure as described in Scheme 1. A mixture of substituted lactones of compounds of formula A can be reduced to form substituted lactols of compounds of formula B in one or more reagents such as, for example, lithium tri tert-butoxy aluminum hydride or the like and solvents such as, tetrahydro furan or the like. Substituted lactols of compounds of formula B can be protected with protecting reagent to form Substituted sugars of compounds of formula C and Substituted deprotected sugars of compounds of formula D in one or more reagents such as, for example, boron trifluoro etherate in methanol or the like. The mixture of compounds of formula C and D can be deprotected to form deprotected compounds of formula E in one or more bases such as, methanolic ammonia or the like. Deprotected compounds of formula E can be treated for selective protection to form selective protected compounds of formula F with one or more protecting reagents such as, for example, tert-Butyl(chloro)diphenyl silyl chloride or the like and one or more bases such as, for example, imidazole or the like and one or more solvents such as, dry chloromethane or the like. Selectively protected compounds of formula F can be oxidized to form oxo compounds of formula G in one or more reagents such as, for example, Des-Martin periodinane and one or more solvents such as, for example, dry chloromethane or the like.

Scheme-2

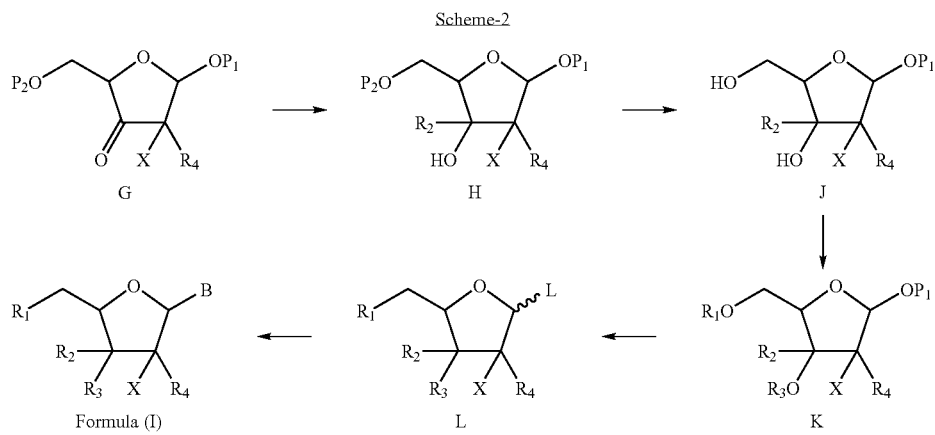

The compounds of Formula (I) (wherein, $R_1$, $R_2$, $R_3$, $R_4$, X and B are as defined above and L is a leaving group (for example, benzoyl or acetyl)) can be prepared by the above procedure as described in Scheme 2. A mixture of oxo compounds of formula G can be reacted with Grignard's reagents (such as, $R_2$—MgX or the like) to form compounds of formula H in one or more solvents such as, THF or dry ether or the like. There is a possibility of getting two different diastereomers of compounds of formula H in this particular step. The ratios of isomers may vary depending on the solvent used for the reaction, protecting groups present in the compound of formula G and other reaction conditions. These diastereomers can easily be separated by the methods known in the literature for example by using column chromatography. The $P_2$ group of compounds of formula H can be selectively deprotected to form hydroxyl compounds of formula J in one or more bases such as, tetra butyl ammonium fluoride or the like and solvents such as, tetrahydra furan or the like. The hydroxy compounds of formulae J can be treated with $R_1/R_3$—Cl (for example, $R_1/R_3$ is benzoyl) to form protected compounds of formula K in one or more reagents such as, N,N-Dimethylamino-pyridine or the like and in one or more solvents/bases such as, dichloromethane, triethylamine or the like. The compounds of formula K can be deprotected in one or more acids such as, sulphuric acid or the like followed by reacting with a suitable reagent (L is leaving group such as, O-acyl or O-silyl) to form compounds of formula L. The compounds of formula L can be treated with suitable bases (B, for example, optionally substituted purine and pyrimidine) to form compounds of formula (I) in the presence of one or more coupling reagents such as, Trimethylsilyl trifluoromethanesulfonate, N,O-Bis(trimethylsilyl)acetamide or the like and in one or more solvents such as, acetonitrile, ethanol, tinchloride or the like. Alternatively the compounds of formula K also can be treated with suitable bases (B, for example, optionally substituted purine and pyrimidine) to form compounds of formula (I) in similar conditions. Depending on the coupling conditions known in the art two different diastereomers of compounds of formula I can be formed. These can be separated by chromatography methods.

Scheme-3

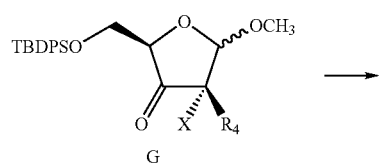

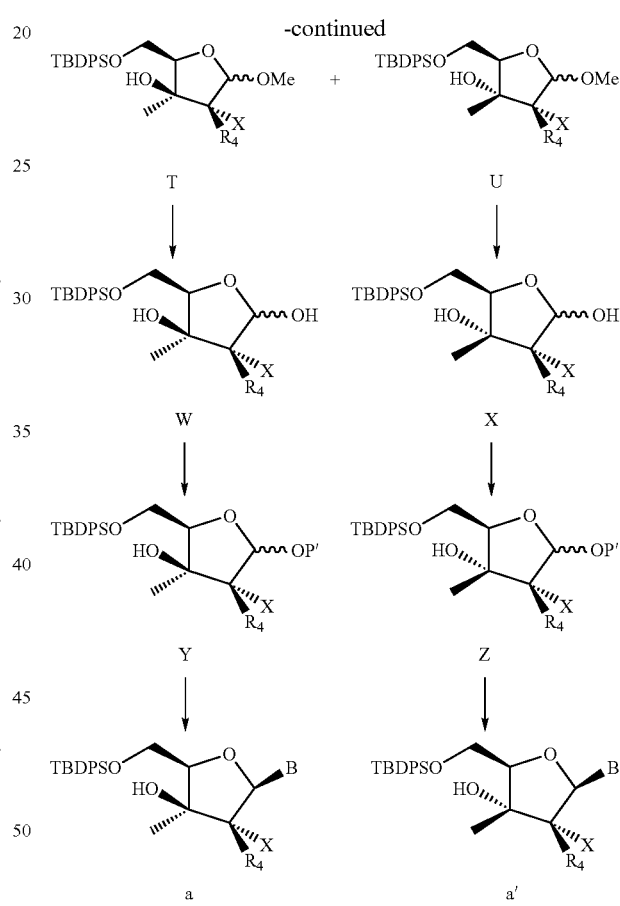

The compounds of Formulae a and a' (wherein, X is a halogen, P' is a protecting group (for example, benzoyl or acetyl), $R_4$ and B are as defined above) can be prepared by the above procedure as described in Scheme 2. A mixture of oxo compounds of formula G can be reduced to form diastereomers of compounds of formulae T and U in one or more reagents such as, for example, lithium tri tert-butoxy aluminum hydride or the like and solvents such as, tetrahydro furan or the like. The compounds of formulae T and U can be demethylated to form respectively hydroxy compounds of formulae W and X in one or more bases such as, for example, methanolic ammonia or the like. Hydroxy compounds of formulae W and X can be treated for selective protection to form respectively selective protected compounds of formulae Y and Z in one or more protecting groups such as, tert-Butyl (chloro)diphenyl silane or the like and one or more bases such as, for example, imidazole or the like and one or more solvents such as, for example, dry chloromethane or the like. Selective protected compounds of formulae Y and Z can be reacted with suitable bases (B, for example, optionally substituted purine and pyrimidine) to form compounds of formulae a and a' in one or more coupling reagents such as, for example, N,O-Bis(trimethylsilyl)acetamide or the like and in one or more solvents such as, for example, acetonitrile, tinchloride or the like.

Experimental

The present invention is further illustrated by the following examples, which are not to be construed in any way as imposing limitations upon the scope of this disclosure, but rather are intended to be illustrative only. On the contrary, it is to be clearly understood that resort may be had to various other embodiments, modifications, and equivalents thereof which, after reading the description herein, may suggest themselves to one of ordinary skill in the art without departing from the spirit of the present invention. Thus, the skilled artisan will appreciate how the experiments and Examples may be further implemented as disclosed by variously altering the following examples, substituents, reagents, or conditions.

Intermediates

Intermediate 1: Synthesis of ((2R,3R,4R)-3-benzoyloxy-4-fluoro-5-hydroxy-4-methyl-tetrahydrofuran-2-yl)methyl benzoate

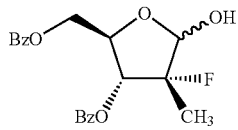

To a stirred solution of ((2R,3R,4R)-3-benzoyloxy-4-fluoro-4-methyl-5-oxo-tetrahydrofuran-2-yl)methyl benzoate (about 60 g, 161 mmol) in tetrahydrafuran (about 300 ml) cooled to about −10° C., then lithium tri tertiary butoxy aluminum hydride (about 241.9 ml, 241 mmol) was added and stirred at about 0° C. for 1 hour. Completion of the reaction was monitored by thin layer chromatography, quenched with saturated ammonium chloride solution. Tetrahydrafuran was removed under reduced pressure and the aqueous layer was extracted with ethyl acetate. The combined organic extracts were washed with water, brine and dried over sodium sulphate. The organic layer was removed under reduced pressure and the residue was purified by silica gel column chromatography using 16% ethyl acetate: hexane as eluent furnished title compound (about 60 g) as a colorless liquid. Yield: 99.46%; $^1$H NMR (300 MHz, CDCl$_3$): δ 8.11-8.00 (m, 4H), 7.61-7.37 (m, 6H), 5.65 (dd, 1H, J=23.4 Hz, 7.8 Hz, 7.5 Hz), 5.34 (dd, 1H, J=9.6 Hz, 2.7 Hz), 4.69-4.66 (m, 1H), 4.57-4.53 (m, 2H), 3.40 (brs, 1H, —OH), 1.60-1.56 (m, 3H, J=22.5); Mass: [M+Na]$^+$: 397 (100%); IR cm$^-$: 3439, 3070, 2940, 2868, 1733, 1729, 1453, 1274, 1115, 710.

Intermediate 2: Synthesis of ((2R,3R,4R)-3-benzoyloxy-4-fluoro-5-methoxy-4-methyl-tetrahydrofuran-2-yl)methyl benzoate (A)

Synthesis of (2R,3R,4R)-4-fluoro-2-(hydroxymethyl)-5-methoxy-4-methyl-tetrahydrofuran-3-yl benzoate (B)

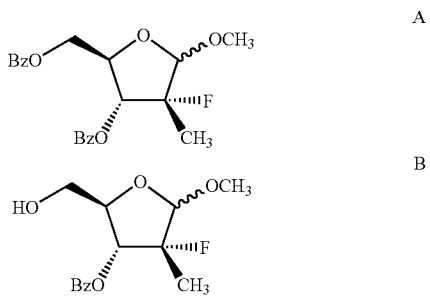

To a stirred solution of ((2R,3R,4R)-3-benzoyloxy-4-fluoro-5-hydroxy-4-methyl-tetrahydrofuran-2-yl)methyl benzoate (about 60 g, 160 mmol) in methanol (about 300 ml), boron trifluoro etherate (about 60.02 ml, 481 mmol) was added at room temperature then reaction mixture was heated to about 80° C. for about 5 hours. After that the reaction was quenched with saturated sodium bicarbonate solution, methanol was removed under reduced pressure, extracted with ethyl acetate. The combined organic extracts were washed with water, brine and dried over sodium sulphate. The organic layer was removed under reduced pressure and the residue was purified by silica gel column chromatography using 8% ethyl acetate: hexane as eluent furnished title compound A (17 g), and 15% ethyl acetate eluded title compound B (18 g) as a colorless liquid. Yield: Combined yield: 56.2%; Intermediate A: $^1$H NMR (300 MHz, CDCl$_3$) compound D: δ 8.01-7.93 (m, 4H), 7.56-7.48 (m, 6H), 5.53 (dd, 1H, J=24.3 Hz, 7.80 Hz), 4.97 (d, 1H, J=9.6 Hz), 4.58-4.53 (m, 2H), 4.41-4.38 (m, 1H), 3.30 (s, 3H), 1.44 (d, 3H, J=22.8); Mass: [M+Na]$^+$: 413 (80%), [M-OCH3]$^+$:357.19 (100%); IR cm$^-$: 3439, 2961, 2939, 1728, 1602, 1452, 1270, 1117, 710.

Intermediate B: $^1$H NMR (300 MHz, CDCl$_3$): δ 8.11-8.08 (m, 2H), 7.61-7.59 (m, 1H), 7.50-7.45 (m, 2H), 5.41 (dd, 1H, J=23.7 Hz, 7.50 Hz), 4.85 (d, 1H, J=10.5 Hz), 4.34-4.32 (m, 2H), 3.76-3.69 (m, 1H), 3.33 (s, 3H), 1.49 (d, 3H, J=22.8); Mass: [M+Na]$^+$: 307 (70%), [M+NH$_4$]$^+$:302 (50%), [M+1]$^+$ 285 (45%).

Intermediate 3: Synthesis of (2R 3R,4R)-4-fluoro-2-(hydroxymethyl)-5-methoxy-4-methyl-tetrahydrofuran-3-ol

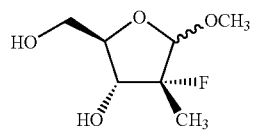

((2R,3R,4R)-3-benzoyloxy-4-fluoro-5-methoxy-4-methyl-tetrahydrofuran-2-yl)methyl benzoate (17 g, 43.8 mmol) in methanolic ammonia solution (25% w/w, 340 ml) was stirred at room temperature for about 36 hours, completion of the reaction monitored by thin-layer chromatography, methanol was removed under reduced pressure. Water added to the reaction mixture and extracted with ethyl acetate and the organic layer was dried over sodium sulphate. Concentration under reduced pressure and purification by silica gel column chromatography using 20% ethyl acetate in hexane eluded the title compound (8 g) as an off-white solid. Yield: 99%.

Intermediate 4: Synthesis of (2R,3R,4R)-4-fluoro-2-(hydroxymethyl)-5-methoxy-4-methyl-tetrahydrofuran-3-ol

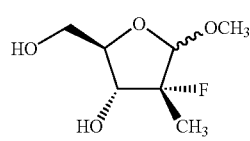

(2R,3R,4R)-4-fluoro-2-(hydroxymethyl)-5-methoxy-4-methyl-tetrahydrofuran-3-yl benzoate (about 18 g, 63.3 mmol) in methanolic ammonia solution (25% w/w, 360 ml) was stirred at room temperature for about 36 hours, completion of the reaction monitored by thin-layer chromatography and methanol was removed under reduced pressure. Water added to the reaction mixture and extracted with ethyl acetate, the organic layer was dried over sodium sulphate and concentrated under reduced pressure. Purification by silica gel column chromatography using 20% ethyl acetate: hexane eluded the title compound (8 g) as an off-white solid. Yield: 70%; $^1$H NMR (300 MHz, CDCl$_3$): δ 4.79 (d, 1H, J=10.8 Hz), 4.01-3.97 (m, 2H), 3.85 (d, 1H,), 3.71-3.66 (m, 1H), 3.44 (s, 3H), 2.05 (brs, 1H, —OH), 2.02 (brs, 1H, —OH), 1.47 (d, 3H, J=23.4 Hz); Mass: [M+Na]$^+$: 203 (100%); IR cm$^-$: 3437, 3372, 3294, 2924, 1459, 1102, 1049, 1006, 821, 731.

Intermediate 5: Synthesis of (2R,3R,4R)-2-((tert-butyldiphenylsilyloxy)methyl)-4-fluoro-5-methoxy-4-methyl-tetrahydrofuran-3-ol

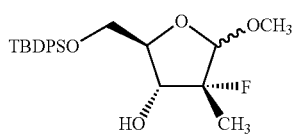

To a magnetically stirred solution of (2R,3R,4R)-4-fluoro-2-(hydroxymethyl)-5-methoxy-4-methyl-tetrahydrofuran-3-ol (about 16 g, 88.8 mmol) and Imidazole (about 9.07 g, 133.2 mmol) in dichloromethane (about 200 ml) cooled to about 0° C., tert-Butyl(chloro)diphenyl silyl chloride (about 23.1 ml, 88.8 mmol) was added and stirred for about 2 hours at room temperature. Completion of the reaction was monitored by thin-layer chromatography, water added to the reaction mixture and extracted with dichloromethane. The combined organic extracts were washed with water, brine and dried over sodium sulphate Concentration under reduced pressure and purified silica gel column chromatography using 7% ethyl acetate: hexane as eluent afforded the title compound (about 16 g) as colorless liquid. Yield: 43%; $^1$H NMR (300 MHz, CDCl$_3$): δ 7.72-7.69 (m, 4H), 7.42-7.41 (m, 6H), 4.79 (d, 1H, J=11.1.0 Hz), 3.97-3.87 (m, 4H), 3.35 (s, 3H), 1.86 (brs, 1H), 1.50 (d, 3H); Mass: [M+Na]$^+$: 441 (100%).

Intermediate 6: Synthesis of (2R,4S)-2-((tert-butyl-diphenylsilyloxy)methyl)-4-fluoro-5-methoxy-4-methyl-dihydrofuran-3(2H)-one

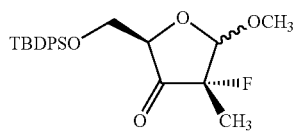

A solution of (2R,3R,4R)-2-((tert-butyldiphenylsilyloxy)methyl)-4-fluoro-5-methoxy-4-methyl-tetrahydrofuran-3-ol (about 16 g, 38.2 mmol) and Dess-Martin periodinane (about 24.3 g, 57.4 mmol) in dichloromethane (about 150 ml) stirred at about 0° C. to room temperature under Nitrogen atmosphere. Completion of the reaction monitored by thin-layer chromatography and quenched by the saturated solution of sodium sulphate and sodium bicarbonate in equal volumes (100 ml+100 ml). The aqueous layers were extracted with dichloromethane and the combined organic extracts were washed with water, brine and dried over sodium sulphate and concentrated under reduced pressure to yield the title compound (24 g as crude). $^1$H NMR (300 MHz, CDCl$_3$): δ 7.69-7.67 (m, 4H), 7.42-7.39 (m, 6H), 5.07 (d, 1H, J=12.3 Hz), 4.38 (dd, 1H, J=5.1 Hz, 3.3 Hz), 3.889-3.83 (m, 2H), 3.46 (s, 3H), 1.42 (d, 3H, J=24 Hz), 1.03 (s, 9H); Mass: [M+Na]$^+$: 439 (65%); IR cm$^-$: 2934, 2859, 1783, 1382, 1114, 998, 703.

Intermediate 7: Synthesis of (2R,4R,)-2-((tert-butyl-diphenylsilyloxy)methyl)-4-fluoro-5-methoxy-3,4-dimethyl-tetrahydrofuran-3-ol (3-R & 3-S isomers)

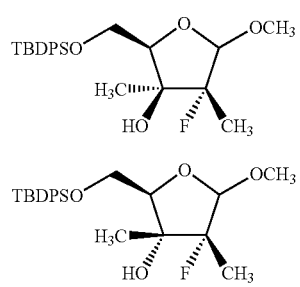

To a solution of (2R,4S)-2-((tert-butyldiphenylsilyloxy)methyl)-4-fluoro-5-methoxy-4-methyl-dihydrofuran-3(2H)-one (about 23 g, 55.2 mmol) in dry ether at about 0° C. was added methyl magnesium bromide (about 60.8 ml, 121 mmol) drop wise for about 30 minutes and stirred at room temperature for about 4 hours. Completion of the reaction monitored by thin-layer chromatography and quenched with saturated ammonium chloride solution. The aqueous layer was extracted with ethyl acetate and the combined organic layers were washed with water, brine and dried over sodium sulphate. Organic layers were concentrated under reduced pressure and purified by silica gel column chromatography using 3% & 3.5% ethyl acetate: hexane as eluent furnished title compounds A (9.1 g) and B (1.5 g) as a colorless liquid. Yield: Overall yield after two steps 64.2%.

Isomer A: ¹H NMR (300 MHz, CDCl₃): δ 7.74-7.72 (m, 4H), 7.43-7.39 (m, 6H), 4.83 (d, 1H, J=15.3 Hz), 4.08 (m, 1H), 3.84-3.80 (m, 2H), 3.39 (s, 3H), 1.34 (d, 3H, J=24.6 Hz), 1.16 (s, 3H), 1.05 (s, 9H); Mass: [M+Na]⁺: 455 (100%).

Isomer B: ¹H NMR (300 MHz, CDCl₃): δ 7.74-7.72 (m, 4H), 7.43-7.39 (m, 6H), 4.81 (d, 1H, J=11.4 Hz), 4.16-4.14 (m, 1H), 4.00-3.81 (m, 2H), 3.37 (s, 3H), 1.42 (d, 3H, J=23.4 Hz), 1.27 (s, 3H), 1.06 (s, 9H); Mass: [M+Na]⁺: 455 (100%).

Intermediate 8: Synthesis of (2R,4R)-4-fluoro-2-(hydroxymethyl)-5-methoxy-3,4-dimethyl-tetrahydrofuran-3-ol

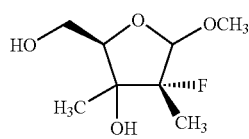

To a solution of (2R,4R)-2-((tert-butyldiphenylsilyloxy)methyl)-4-fluoro-5-methoxy-3,4-dimethyl-tetrahydrofuran-3-ol (about 6.3 g, 14.5 mmol) in tetrahydrafuran (about 100 ml) at about 0° C. was added 1N tetra butyl ammonium fluoride solution (about 14.5 ml, 14.5 mmol) drop wise for about 10 minutes and stirred at room temperature for about 1.5 hours. Completion of the reaction monitored by thin-layer chromatography and neutralized with saturated sodium bicarbonate. Aqueous layer was extracted with ethyl acetate and the combined organic extracts were washed with water, brine and dried over sodium sulphate and concentrated under reduced pressure, purified by silica gel column chromatography using 50% ethyl acetate: hexane as eluent furnished the title compound (2.8 g) as a colorless liquid. Yield: 99%; ¹H NMR (300 MHz, CDCl₃): δ 4.84 (d, 1H, J=11.1 Hz), 4.11 (m, 1H), 3.88-3.87 (m, 2H), 3.46 (s, 3H), 3.35 (s, 1H), 2.05 (m, 1H), 1.40 (d, 3H, J=23.4 Hz), 1.27 (d, 3H, J=2.1 Hz); Mass: [M+Na]⁺: 217 (100%).

Intermediate 9: Synthesis of ((2R,4R)-3-benzoyloxy-4-fluoro-5-methoxy-3,4-dimethyl-tetrahydrofuran-2-yl)methyl benzoate (A)

Synthesis of ((2R,4R)-4-fluoro-3-hydroxy-5-methoxy-3,4-dimethyl-tetrahydrofuran-2-yl)methyl benzoate (B)

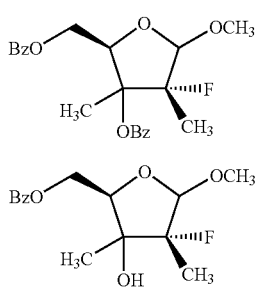

To a solution of (2R,4R)-4-fluoro-2-(hydroxymethyl)-5-methoxy-3,4-dimethyl-tetrahydrofuran-3-ol (about 2.8 g, 14.4 mmol) in dry dichloromethane (about 40 ml) at about 0° C. was added N,N-Dimethylamino-pyridine (about 2.6 g, 21.6 mmol), triethylamine (about 7.9 ml, 57.7 mmol), stirred for about 15 minutes then drop wise addition of benzoylchloride (about 10 ml, 86.4 mmol) for about 10 minutes and stirred at about 45° C. for about 48 hours. Completion of the reaction monitored by thin-layer chromatography and quenched with water. Aqueous layer was extracted with ethyl acetate and the combined organic layers were washed with saturated sodium bicarbonate solution, brine and dried over sodium sulphate. Concentration under reduced pressure and purification by silica gel column chromatography using 2% and 5% ethyl acetate: hexane as eluent furnished title compounds A and B as a colorless liquid. ¹H NMR (300 MHz, CDCl₃): δ 8.09-8.06 (m, 4H), 7.57-7.42 (m, 6H), 4.85 (d, 1H, J=10.2 Hz), 4.60-4.59 (m, 2H), 4.50-4.44 (m, 1H), 3.46 (s, 3H), 1.46 (d, 3H, J=23.4 Hz), 1.26 (s, 3H); Mass: [M+Na]⁺: 425 (100%); IR cm⁻: 3425, 2927, 1723, 1679, 1602, 1451, 1281, 1124, 710.

Intermediate 10: Synthesis of ((2R,4R)-3,5-diacetoxy-4-fluoro-3,4-dimethyl-tetrahydrofuran-2-yl) methyl benzoate

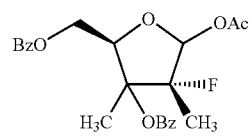

To a solution of ((2R,4R)-3-benzoyloxy-4-fluoro-5-methoxy-3,4-dimethyl-tetrahydrofuran-2-yl)methyl benzoate (about 3.3 g, 8.2 mmol) in acetic acid (about 20 ml) at about 0° C. was added sulphuric acid (about 1.8 ml, 18.0 mmol) and acetic anhydride (about 3 ml, 34.4 mmol), and stirred the reaction at room temperature for about 2 hours. Completion of the reaction was monitored by thin-layer chromatography, and quenched with water. Aqueous layer was extracted with ethyl acetate and the combined organic layers were washed with saturated sodium bicarbonate solution, brine and dried over sodium sulphate and concentrated under reduced pressure to afford the title compound (0.5 g) as a colorless liquid. ¹H NMR (300 MHz, CDCl₃): δ 8.04-7.96 (m, 4H), 7.38-7.36 (m, 6H), 6.28 (d, 1H, J=14.1 Hz), 4.86 (m, 1H), 4.57 (m, 2H), 1.98 (s, 3H), 1.58 (d, 3H, J=23.7 Hz), 1.25 (s, 3H); Mass: [M+Na]⁺: 453 (100%).

Intermediate 11: Synthesis of ((2R,4R)-3,5-diacetoxy-4-fluoro-3,4-dimethyl-tetrahydrofuran-2-yl) methyl benzoate

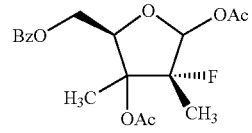

To a solution of ((2R,4R)-4-fluoro-3-hydroxy-5-methoxy-3,4-dimethyl-tetrahydrofuran-2-yl)methyl benzoate (about 6 g, 20.13 mmol) in acetic acid (about 60 ml) at about 0° C. was added sulphuric acid (about 3.2 ml, 44.2 mmol) and acetic anhydride (about 5.4 ml, 84.4 mmol), and stirred the reaction at room temperature for about 16 hours. Completion of the reaction monitored by thin-layer chromatography, reaction mixture was slowly added to ice cold water, and extracted with ethyl acetate, organic layer was washed with saturated sodium bicarbonate and dried over sodium sulphate and concentrated under reduced pressure to yield the title compound (1.5 g) as a colorless gummy mass. $^1$H NMR (300 MHz, CDCl$_3$): δ 8.06-8.04 (m, 2H), 7.57-7.55 (m, 1H), 7.47-7.42 (m, 2H), 6.19 (d, 1H, J=20.4 Hz), 4.73-4.67 (m, 1H), 4.67-4.44 (m, 2H), 2.06 (s, 3H), 1.80 (s, 3H), 1.51 (d, 3H, J=22.8 Hz), 1.43 (s, 3H); Mass: [M+Na]$^+$: 391 (100%).

Intermediate 12: Synthesis of (2R,4R)-4-fluoro-2-(hydroxymethyl)-5-methoxy-3,4-dimethyl-tetrahydrofuran-3-ol

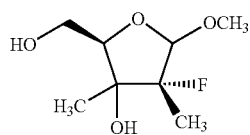

To a solution of (2R,4R)-2-((tert-butyldiphenylsilyloxy)methyl)-4-fluoro-5-methoxy-3,4-dimethyl-tetrahydrofuran-3-ol (about 1.5 g, 3.4 mmol) in tetrahydrafuran (about 25 ml) at about 0° C. was added 1M tetra butyl ammonium fluoride solution (about 3.47 ml, 3.4 mmol) drop wise for about 10 minutes and stirred at room temperature for about 1.5 hours. Completion of the reaction monitored by thin-layer chromatography and neutralized with saturated sodium bicarbonate. Aqueous layer was extracted with ethyl acetate and the combined organic extracts were washed with water, brine and dried over sodium sulphate and concentrated under reduced pressure, purified by silica gel column chromatography using 50% ethyl acetate: hexane as eluent furnished the title compound (0.5 g) as a colorless liquid. Yield: 75%; $^1$H NMR (300 MHz, CDCl$_3$): δ 4.84 (d, 1H, J=15.3 Hz), 4.00-3.98 (m, 3H), 3.45 (s, 3H), 1.34 (d, 3H, J=24.3 Hz), 1.17 (s, 3H); Mass: [M+Na]$^+$: 217 (100%).

EXAMPLES

Example 1

Preparation of ((2R,3S,4R)-3-benzoyloxy-5-(6-chloro-9H-purin-9-yl)-4-fluoro-3,4-dimethyl-tetrahydrofuran-2-yl)methyl benzoate

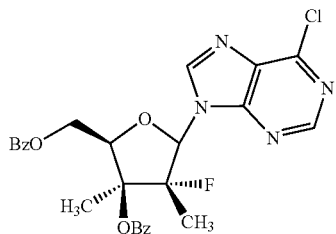

To a stirred solution of 6-chloropurine (about 0.26 g, 1.74 mmol) in Acetonitrile (about 8 ml) was added 1,8-Diazabicyclo[5.4.0]undec-7-ene (about 0.52 ml, 3.48 mmol) and Trimethylsilyl trifluoromethanesulfonate (about 0.84 ml, 4.65 mmol) at about 0° C., stirred for about 15 minutes then ((2R,3S,4R)-3,5-diacetoxy-4-fluoro-3,4-dimethyl-tetrahydrofuran-2-yl)methyl benzoate (about 0.5 g, 1.16 mmol) in Acetonitrile (about 7 ml) was added and reaction continued stirring at about 65° C. for about 8 hours. Completion of reaction monitored by thin-layer chromatography and quenched with saturated sodium bicarbonate. Aqueous layer was extracted with ethyl acetate and the combined organic layers were washed with sodium bicarbonate solution, brine and dried over sodium sulphate. Concentration under reduced pressure and purification by silica gel column chromatography using 20% ethyl acetate: hexane as eluent furnished title compounds Isomer A and B (0.24 g) as a colorless liquid. Yield: 40%

Isomer A: $^1$H NMR (300 MHz, CDCl$_3$): δ 8.77 (s, 1H), 8.38 (d, 1H, J=3.6 Hz), 8.04-7.98 (m, 4H), 7.55-7.40 (m, 6H), 6.74 (d, 1H, J=22.2 Hz), 5.00-4.93 (m, 2H), 4.65-4.60 (m, 1H), 1.58 (d, 3H, J=22.8 Hz), 1.28 (s, 3H); Mass: [M+Na]$^+$: 547 (95%), [M+Na+2]$^+$: 549 (35%), [M+1]$^+$525 (80%). HPLC: 98.34%.

Isomer B: $^1$H NMR (300 MHz, CDCl$_3$): δ 8.94 (s, 1H), 8.54 (d, 1H, J=4.2 Hz), 8.06-8.03 (m, 2H), 7.59 (m, 1H), 7.49-7.43 (m, 2H), 6.97 (d, 1H, J=21.3 Hz), 4.88-4.80 (m, 2H), 4.53-4.47 (m, 1H), 2.19 (s, 3H), 1.91 (s, 3H), 1.49 (d, 3H, J=23.1 Hz); $^{13}$C NMR: 13.61, 14.15, 29.54, 62.91, 84.42, 86.95, 88.21, 102.38, 128.37 (2), 129.35 (3), 131.24, 133.24, 144.41, 151.13, 151.71, 152.09, 166.04, 168.81; ES Mass: [M+Na]$^+$: 485 (25%), [M+1]$^+$ 463 (30%).

Example 2

Preparation of (2R,3S,4R)-5-(6-amino-9H-purin-9-yl)-4-fluoro-tetrahydro-2-(hydroxymethyl)-3,4-dimethylfuran-3-ol (Compound 2A) &

(2R,3S,4R)-4-fluoro-2-(hydroxymethyl)-5-(6-methoxy-9H-purin-9-yl)-3,4-dimethyltetrahydrofuran-3-ol (Compound 2B)

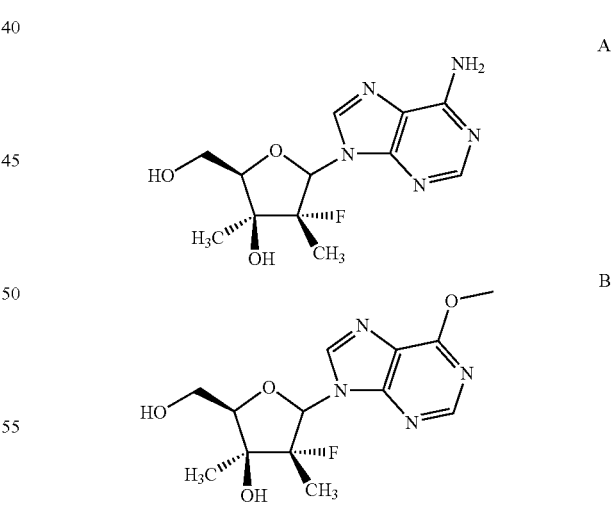

The solutions of isomers obtained in Example 1 [((2R,3S,4R)-3-benzoyloxy-5-(6-chloro-9H-purin-9-yl)-4-fluoro-3,4-dimethyl-tetrahydrofuran-2-yl)methyl benzoate (about 0.125 g, 0.02 mmol)] were independently in methanolic ammonia (25% w/w 4 ml) was stirred at room temperature for overnight. Completion of the reaction monitored by thin-layer chromatography, methanol was removed under reduced pressure. Water added to the crude and extracted with ethyl acetate, and the organic layer was dried over sodium sulphate and concentrated under reduced pressure. Purified by silica gel column chromatography using 25% ethyl acetate: hexane to elude title compound A (Isomer I and II) and 1% methanol in dichloromethane to elude title compound B (Isomer I and II) as a colorless gummy mass.

Compound A (Isomer I): $^1$H NMR (300 MHz, CDCl$_3$): δ 8.30 (s, 1H), 8.07 (s, 1H), 6.60 (d, 1H, J=22.8 Hz), 6.32 (brs, 2H —NH$_2$), 4.32 (m, 1H), 4.18-4.17 (m, 2H), 1.40 (d, 3H, J=22.8 Hz), 1.28 (s, 3H); Mass: [M+1]$^+$ 298 (100%).

Compound A (Isomer II): $^1$H NMR (300 MHz, CDCl$_3$): δ 8.79 (s, 1H), 8.47 (d, 1H, J=4.2 Hz), 6.86 (d, 1H, J=20.7 Hz), 5.64 (bs, 1H), 4.62 (bs, 1H), 4.32-4.29 (m, 1H), 4.00-3.88 (m, 2H), 1.35-1.27 (m, 6H); Mass: [M+1]$^+$ 317 (80%), [M+Na]$^+$ 339 (95%); IR cm$^-$: 3390, 2924, 1598, 1555, 1399, 1220, 1052, 973, 834; HPLC: 91.4%

Compound B (Isomer I): $^1$H NMR (300 MHz, CDCl$_3$): δ 8.54 (s, 1H), 8.17 (d, 1H, J=3.6), 6.63 (d, 1H, J=22.5 Hz), 4.96-4.94 (m, 1H), 4.34 (m, 1H), 4.20 (s, 3H), 4.13 (m, 1H), 1.40 (d, 3H, J=22.5 Hz), 1.25 (s, 3H); Mass: [M+1]$^+$ 313 (100%), [M−1]$^+$ 311 (100%).

Compound B (Isomer II): $^1$H NMR (300 MHz, CDCl$_3$): δ 8.37 (s, 1H), 8.08 (d, 1H, J=3.9), 6.38 (d, 1H, J=21.3 Hz), 5.44 (d, 1H, J=1.2 Hz), 4.61-4.57 (t, 1H), 4.14-4.13 (m, 1H), 3.92 (s, 3H), 3.77-3.71 (m, 2H), 1.15 (d, 3H, J=2.1 Hz), 1.08 (d, 3H, J=22.8 Hz); Mass: [M+1]$^+$ 313 (100%), [M+Na]$^+$ 335 (25%); IR cm$^-$: 3433, 3153, 2910, 1328, 1221, 1120, 1051, 996, 886; HPLC: 90.6%.

Example 3

Preparation of ((2R,3S,4R)-3-acetoxy-5-(6-chloro-9H-purin-9-yl)-4-fluoro-3,4-dimethyl-tetrahydrofuran-2-yl)methyl benzoate

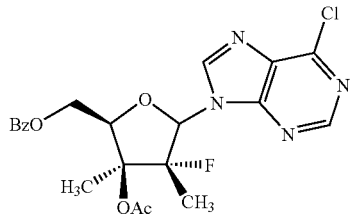

To a stirred solution of 6-chloropurine (about 0.87 g, 5.7 mmol) in acetonitrile (about 20 ml) was added 1,8-Diazabicyclo[5.4.0]undec-7-ene (about 1.7 ml, 11.4 mmol) and Trimethylsilyl trifluoromethanesulfonate (about 2.76 ml, 15.2 mmol) at about 0° C., stirred for about 15 minutes then ((2R,3S,4R)-3,5-diacetoxy-4-fluoro-3,4-dimethyl-tetrahydrofuran-2-yl)methyl benzoate (about 1.4 g, 3.8 mmol) dissolved in Acetonitrile (about 20 ml) was added and reaction continued stirring at about 65° C. for about 8 hours. Completion of reaction monitored by thin-layer chromatography and quenched with saturated sodium bicarbonate. Aqueous layer was extracted with ethyl acetate and the combined organic layers were washed with saturated sodium bicarbonate solution, brine and dried over sodium sulphate. Concentration under reduced pressure and purification by silica gel column chromatography using 20% ethyl acetate: hexane as eluent furnished title compounds Isomer A and B (0.7 g) as a colorless liquid. Yield: 57%;

Isomer A: $^1$H NMR (300 MHz, CDCl$_3$): δ 8.78 (s, 1H), 8.36 (d, 1H, J=3.6 Hz), 8.08-8.04 (m, 2H), 7.60 (m, 1H), 7.49-7.44 (m, 2H), 6.63 (d, 1H, J=22.5 Hz), 4.90-4.80 (m, 3H), 2.21 (s, 3H), 1.92 (s, 3H), 1.48 (d, 3H, J=23.1 Hz); $^{13}$C NMR: 13.72, 14.35, 29.58, 62.90, 84.39, 88.12, 88.32, 101.67, 121.86, 128.44 (2), 129.59 (3), 133.35, 141.64, 148.82, 152.55, 161.98, 166.07, 168.70; ES Mass: [M+Na]$^+$: 485 (50%), [M+1]$^+$ 463 (88%).

Isomer B: $^1$H NMR (300 MHz, CDCl$_3$): δ 8.74 (s, 1H), 8.38 (d, 1H, J=3.9 Hz), 8.06-8.03 (m, 2H), 7.58-7.56 (m, 1H), 7.47-7.42 (m, 2H), 6.46 (d, 1H, J=20.1 Hz), 4.94-4.72 (m, 2H), 4.66-4.59 (m, 1H), 2.11 (s, 3H), 1.79 (s, 3H), 1.41 (m, 3H); Mass: [M+Na]$^+$: 485 (40%), [M+1]$^+$ 463 (45%).

Example 4

Preparation of ((2R,3S,4R)-3-acetoxy-5-(6-(cyclopropylamino)-9H-purin-9-yl)-4-fluoro-3,4-dimethyl-tetrahydrofuran-2-yl)methyl benzoate

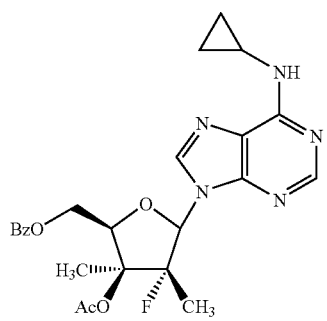

To a stirred solution of ((2R,3S,4R)-3-acetoxy-5-(6-chloro-9H-purin-9-yl)-4-fluoro-3,4-dimethyl-tetrahydrofuran-2-yl)methyl benzoate (about 0.2 g, 0.43 mmol) in ethanol (about 5 ml) was added cyclopropylamine (about 0.296 ml, 5.19 mmol) and refluxed for about 30 minutes. Completion of the reaction monitored by thin-layer chromatography, water added to the reaction mixture and the aqueous layer was extracted with ethyl acetate and the combined organic layers were washed with brine and dried over sodium sulphate. Concentration under reduced pressure and purification by silica gel column chromatography using 40% ethyl acetate in hexane as eluent furnished title compounds Isomer A and B (0.13 g) as a colorless gummy mass. Yield: 62%;

Isomer A: $^1$H NMR (300 MHz, CDCl$_3$): δ 8.74 (s, 1H), 8.38 (d, 1H, J=3.9 Hz), 8.06-8.03 (m, 2H), 7.58-7.56 (m, 1H), 7.47-7.42 (m, 2H), 6.46 (d, 1H, J=20.1 Hz), 4.94-4.72 (m, 2H), 4.66-4.59 (m, 1H), 2.11 (s, 3H), 1.79 (s, 3H), 1.41 (m, 3H); Mass: [M+Na]$^+$: 485 (40%), [M+1]$^+$ 463 (45%).

Isomer B: $^1$H NMR (300 MHz, CDCl$_3$): δ 8.64 (s, 1H), 8.08-8.04 (m, 3H), 7.61-7.58 (m, 1H), 7.49-7.44 (m, 2H), 6.37 (bs, 1H), 6.11 (d, 1H, J=22.8 Hz), 4.89-4.84 (m, 1H), 4.74-4.71 (m, 1H), 4.56-4.49 (m, 1H), 2.92-2.88 (m, 1H), 2.26 (s, 3H), 1.88 (d, 3H, J=2.1 Hz), 1.29 (d, 3H, J=20.4 Hz), 0.90-0.86 (m, 4H); Mass: [M+1]$^+$ 484 (100%), 485 (35%); IR cm$^-$: 3393, 2925, 2284, 1753, 1724, 1178, 1024, 952, 797; HPLC: 90%.

Example 5

Preparation of ((2R,4R)-3-acetoxy-4-fluoro-5-(6-(4-fluorobenzylamino)-9H-purin-9-yl)-3,4-dimethyl-tetrahydrofuran-2-yl)methyl benzoate

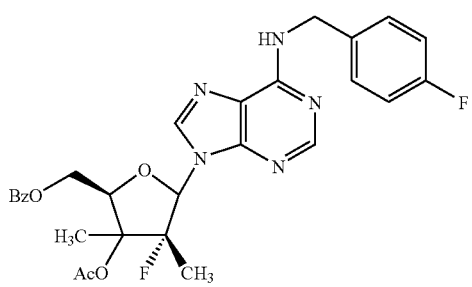

To a stirred solution of ((2R,4R)-3-acetoxy-5-(6-chloro-9H-purin-9-yl)-4-fluoro-3,4-dimethyl-tetrahydrofuran-2-yl)methyl benzoate (about 0.2 g, 0.43 mmol) in ethanol (about 5 ml) was added 4-fluorobenzylamine (about 0.39 ml, 3.46 mmol) and refluxed for about 2 hours. Completion of the reaction monitored by thin-layer chromatography and water added to the reaction mixture. The aqueous layer was extracted with ethyl acetate and the combined organic layers were washed with brine and dried over sodium sulphate. Concentration under reduced pressure and purification by silica gel column chromatography using 40% ethyl acetate in hexane as eluent furnished title compound (0.13 g) as a colorless gummy mass. Yield: 56%; $^1$H NMR (300 MHz, CDCl$_3$): δ 8.74 (s, 1H), 8.38 (d, 1H, J=3.9 Hz), 8.06-8.03 (m, 2H), 7.58-7.56 (m, 1H), 7.47-7.42 (m, 2H), 6.46 (d, 1H, J=20.1 Hz), 4.94-4.72 (m, 2H), 4.66-4.59 (m, 1H), 2.11 (s, 3H), 1.79 (s, 3H), 1.41 (m, 3H); Mass: [M+Na]$^+$: 485 (40%), [M+1]$^+$ 463 (45%).

Example 6

Preparation of ((2R,3S,4R)-3-acetoxy-5-(6-(cyclobutylamino)-9H-purin-9-yl)-4-fluoro-3,4-dimethyl-tetrahydrofuran-2-yl)methyl benzoate

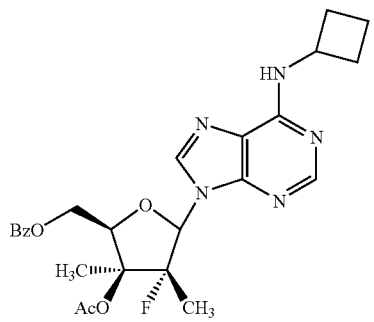

To a stirred solution of ((2R,3S,4R)-3-acetoxy-5-(6-chloro-9H-purin-9-yl)-4-fluoro-3,4-dimethyl-tetrahydrofuran-2-yl)methyl benzoate (about 0.4 g, 0.86 mmol) in ethanol (about 5 ml) was added cyclobutylamine (about 0.88 ml, 10.38 mmol) and refluxed for about 2 hours. Completion of the reaction monitored by thin-layer chromatography and water added to the reaction mixture. The aqueous layer was extracted with ethyl acetate and the combined organic layers were washed with brine and dried over sodium sulphate. Concentration under reduced pressure and purification by silica gel column chromatography using 40% ethyl acetate in hexane as eluent furnished title compounds Isomer A and B (0.20 g) as a colorless gummy mass. Yield: 46.5%.

Isomer A: $^1$H NMR (300 MHz, CDCl$_3$): δ 8.74 (s, 1H), 8.38 (d, 1H, J=3.9 Hz), 8.06-8.03 (m, 2H), 7.58-7.56 (m, 1H), 7.47-7.42 (m, 2H), 6.46 (d, 1H, J=20.1 Hz), 4.94-4.72 (m, 2H), 4.66-4.59 (m, 1H), 2.11 (s, 3H), 1.79 (s, 3H), 1.41 (m, 3H); Mass: [M+Na]$^+$: 485 (40%), [M+1]$^+$ 463 (45%).

Isomer B: $^1$H NMR (300 MHz, CDCl$_3$): δ 8.52 (s, 1H), 8.08-8.05 (m, 3H), 7.71-7.60 (m, 1H), 7.48-7.43 (m, 2H), 6.29 (d, 1H, J=7.5 Hz), 6.14 (d, 1H, J=22.8 Hz), 4.94-4.82 (m, 1H), 4.68-4.65 (m, 1H), 4.59-4.55 (m, 1H), 4.23-4.20 (m, 1H), 2.36-1.36 (m, 15H); Mass: [M+1]$^+$ 498 (60%), [M+Na]$^+$ 520 (100%); HPLC: 91.7%.

Example 7

Preparation of ((2R,4R)-3-acetoxy-4-fluoro-5-(6-(furan-2-ylmethylamino)-9H-purin-9-yl)-3,4-dimethyl-tetrahydrofuran-2-yl)methyl benzoate

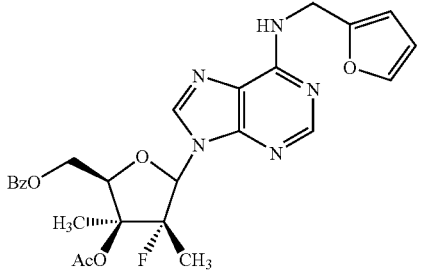

To a stirred solution of ((2R,4R)-3-acetoxy-5-(6-chloro-9H-purin-9-yl)-4-fluoro-3,4-dimethyl-tetrahydrofuran-2-yl)methyl benzoate (about 0.4 g, 0.86 mmol) in ethanol (about 5 ml) was added furfurylamine (about 0.96 ml, 10.38 mmol) and refluxed for about 30 minutes. Completion of the reaction monitored by thin-layer chromatography, water added to the reaction mixture and the aqueous layer was extracted with ethyl acetate and the combined organic layers were washed with brine and dried over sodium sulphate. Concentration under reduced pressure and purification by silica gel column chromatography using 40% ethyl acetate in hexane as eluent furnished title compounds Isomer A and B (0.20 g) as a colorless gummy mass. Yield: 44.2%.

Isomer A: $^1$H NMR (300 MHz, CDCl$_3$): δ 8.44 (s, 1H), 8.06-7.98 (m, 3H), 7.58-7.42 (m, 4H), 6.54 (d, 1H, J=24 Hz), 6.32 (d, 2H, J=3 Hz), 6.20 (bs, 1H), 4.88-4.78 (m, 4H), 4.49-4.42 (m, 1H), 2.16 (s, 3H), 1.89 (s, 3H), 1.45 (d, 3H, J=23.1 Hz). Mass: [M+1]$^+$ 524 (100%), 525 (35%); IR (Kbr, cm$^-$): 3414, 2926, 2124, 1748, 1725, 1626, 1460, 1230, 1033, 711, 523; HPLC: 92%.

Isomer B: $^1$H NMR (300 MHz, CDCl$_3$): δ 8.60 (s, 1H), 8.12-8.00 (m, 3H), 7.48-7.43 (m, 3H), 7.30 (d, 1H, J=0.9 Hz), 6.46-6.43 (m, 1H), 6.27-6.21 (m, 2H), 6.11 (d, 1H, J=22.5 Hz), 4.97-4.90 (dd, 1H, J1=15 Hz, J2=15 Hz), 4.76-4.71 (dd, 1H, J1=12 Hz, J2=12 Hz), 4.60-4.41 (m, 3H), 4.22-4.20 (m, 1H), 2.14 (s, 3H), 1.82 (d, 3H, J=2.4 Hz), 1.34 (d, 3H, J=22.2 Hz); Mass: [M+Na]$^+$ 546 (100%), 524 (40%); HPLC: 97%.

Example 8

Preparation of ((2R,4R)-3-acetoxy-4-fluoro-5-(6-(isobutyl amino)-9H-purin-9-yl)-3,4-dimethyl-tetrahydrofuran-2-yl)methyl benzoate

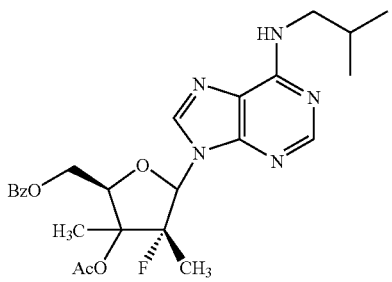

To a stirred solution of ((2R,4R)-3-acetoxy-5-(6-chloro-9H-purin-9-yl)-4-fluoro-3,4-dimethyl-tetrahydrofuran-2-yl) methyl benzoate (about 0.4 g, 0.86 mmol) in ethanol (about 5 ml) was added isobutyl amine (about 1.03 ml, 10.38 mmol) and refluxed for about 20 minutes. Completion of the reaction monitored by thin-layer chromatography, water added to the reaction mixture and the aqueous layer was extracted with ethyl acetate and the combined organic layers were washed with brine and dried over sodium sulphate. Concentration under reduced pressure and purification by silica gel column chromatography using 40% ethyl acetate in hexane as eluent furnished title compound (0.18 g) as a colorless gummy mass. Yield: 41.6%; $^1$H NMR (300 MHz, CDCl$_3$): δ 8.39 (s, 1H), 8.06-7.79 (m, 3H), 7.58-7.55 (m, 3H), 6.54 (d, 1H, J=23.4 Hz), 5.90 (bs, 1H), 4.83-4.78 (m, 2H), 4.49-4.44 (m, 1H), 3.49 (m, 2H), 2.14 (s, 3H), 2.09-1.90 (m, 1H), 1.89 (d, 3H, J=2.4 Hz), 1.45 (d, 3H, J=22.8 Hz), 1.02 (d, 6H, J=6.6 Hz); Mass: [M+1]$^+$ 500 (100%), 501 (35%); IR cm$^-$: 3372, 3141, 2927, 1752, 1622, 1274, 1063, 1026, 952, 713; HPLC: 94.7%.

Example 9

Preparation of ((2R,4R)-3-acetoxy-4-fluoro-5-(6-(3-methoxybenzylamino)-9H-purin-9-yl)-3,4-dimethyl-tetrahydrofuran-2-yl)methyl benzoate

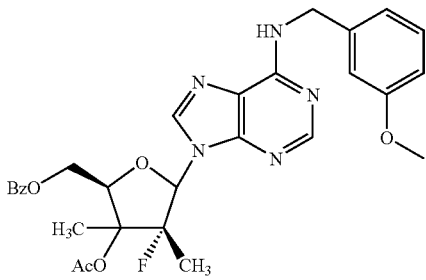

To a stirred solution of ((2R,4R)-3-acetoxy-5-(6-chloro-9H-purin-9-yl)-4-fluoro-3,4-dimethyl-tetrahydrofuran-2-yl) methyl benzoate (about 0.4 g, 0.86 mmol) in ethanol (about 5 ml) was added 3-methoxybenzylamine (about 1.34 ml, 10.38 mmol) and refluxed for about 20 minutes. Completion of the reaction monitored by thin-layer chromatography, water added to the reaction mixture and the aqueous layer was extracted with ethyl acetate and the combined organic layers were washed with brine and dried over sodium sulphate. Concentration under reduced pressure and purification by silica gel column chromatography using 40% ethyl acetate in hexane as eluent furnished title compound (0.10 g) as a colorless gummy mass. Yield: 21%; $^1$H NMR (300 MHz, CDCl$_3$): δ 8.42 (s, 1H), 8.03-7.98 (m, 3H), 7.60-7.42 (m, 3H), 6.99-6.94 (m, 2H), 6.84-6.81 (m, 2H), 6.55 (d, 1H, J=23.1 Hz), 6.31 (bs, 1H), 4.84-4.78 (m, 3H), 4.49-4.45 (m, 1H), 3.79 (s, 3H), 2.18 (s, 3H), 1.89 (d, 3H, J=2.4 Hz), 1.47 (d, 3H, J=23.1 Hz); Mass: [M+1]$^+$ 564 (100%), [M+Na]$^+$ 586 (40%); IR cm$^-$: 3430, 2928, 2381, 2170, 1734, 1624, 1461, 1053, 950, 713; HPLC: 90.1%.

Example 10

Preparation of ((2R,4R)-3-acetoxy-5-(6-(3-chlorobenzylamino)-9H-purin-9-yl)-4-fluoro-3,4-dimethyl-tetrahydrofuran-2-yl)methyl benzoate

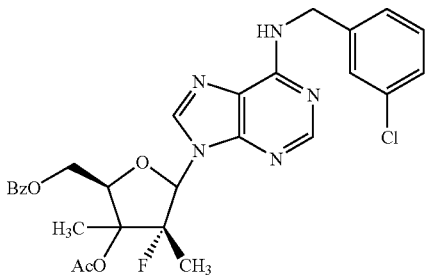

To a stirred solution of ((2R,4R)-3-acetoxy-5-(6-chloro-9H-purin-9-yl)-4-fluoro-3,4-dimethyl-tetrahydrofuran-2-yl) methyl benzoate (about 0.4 g, 0.86 mmol) in ethanol (about 5 ml) was added 3-chlorobenzylamine (about 1.26 ml, 10.38 mmol) and refluxed for about 20 minutes. Completion of the reaction mixture monitored by thin-layer chromatography, water added to the reaction mixture and the aqueous layer was extracted with ethyl acetate and the combined organic layers were washed with brine and dried over sodium sulphate. Concentration under reduced pressure and purification by silica gel column chromatography using 40% ethyl acetate in hexane as eluent furnished title compound (0.30 g) as a colorless gummy mass. Yield: 61.2%; $^1$H NMR (300 MHz, CDCl$_3$): δ 8.42 (s, 1H), 8.06-8.01 (m, 4H), 7.58-7.24 (m, 6H), 6.56 (d, 1H, J=22.8 Hz), 6.45 (bs, 1H), 4.84-4.78 (m, 3H), 4.49-4.42 (m, 1H), 2.17 (s, 3H), 1.89 (d, 3H, J=2.4 Hz), 1.46 (d, 3H, J=23.1 Hz); Mass: [M+1]$^+$ 568 (50%), [M+Na]$^+$ 590 (70%); IR cm$^-$: 3782, 3414, 2929, 2294, 2177, 1619, 1274, 1061, 712; HPLC: 96%.

Example 11

Preparation of ((2R,4R)-3-acetoxy-4-fluoro-5-(6-(2-methoxybenzylamino)-9H-purin-9-yl)-3,4-dimethyl-tetrahydrofuran-2-yl)methyl benzoate

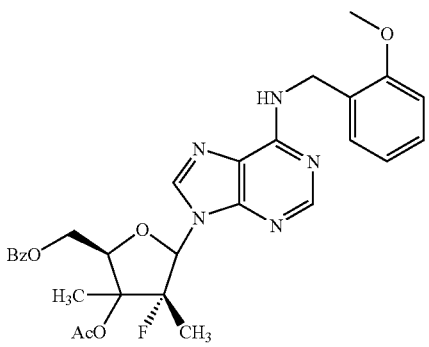

To a stirred solution of ((2R,4R)-3-acetoxy-5-(6-chloro-9H-purin-9-yl)-4-fluoro-3,4-dimethyl-tetrahydrofuran-2-yl)

methyl benzoate (about 0.2 g, 0.43 mmol) in ethanol (5 ml) was added 2-methoxybenzylamine (about 0.67 ml, 5.19 mmol) and refluxed for about 20 minutes. Completion of the reaction monitored by thin-layer chromatography, water added to the reaction mixture and the aqueous layer was extracted with ethyl acetate and the combined organic layers were washed with brine and dried over sodium sulphate. Concentration under reduced pressure and purification by silica gel column chromatography using 40% ethyl acetate in hexane as eluent furnished title compound (0.08 g) as a colorless gummy mass. Yield: 35%; $^1$H NMR (300 MHz, CDCl$_3$): δ 8.51 (s, 1H), 8.06-7.96 (m, 3H), 7.58-7.33 (m, 5H), 6.94-6.88 (m, 2H), 6.54 (d, 1H, J=23.1 Hz), 6.27 (bs, 1H), 4.85-4.78 (m, 2H), 4.48-4.44 (m, 1H), 3.88 (s, 3H), 2.16 (s, 3H), 1.88 (d, 3H, J=2.4 Hz), 1.44 (d, 3H, J=23.1 Hz); Mass: [M+1]$^+$ 564 (100%), [M+Na]$^+$ 586 (60%); IR cm$^-$: 3429, 2929, 2863, 2177, 1733, 1466, 1240, 1033, 713; HPLC: 93.1%.

Example 12

Preparation of ((2R,4R)-3-acetoxy-5-(6-(2-chlorobenzylamino)-9H-purin-9-yl)-4-fluoro-3,4-dimethyl-tetrahydrofuran-2-yl)methyl benzoate

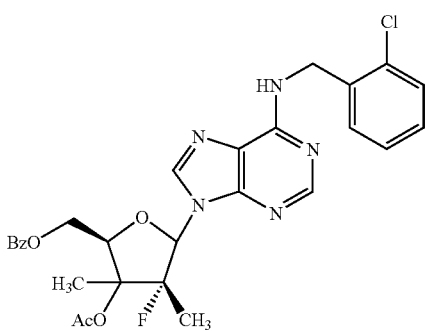

To a stirred solution of ((2R,4R)-3-acetoxy-5-(6-chloro-9H-purin-9-yl)-4-fluoro-3,4-dimethyl-tetrahydrofuran-2-yl) methyl benzoate (about 0.2 g, 0.43 mmol) in ethanol (about 5 ml) was added 2-chlorobenzylamine (about 0.62 ml, 5.19 mmol) and stirred at room temperature for about 15 hours. Completion of the reaction mixture monitored by thin-layer chromatography, water added to the reaction mixture and the aqueous layer was extracted with ethyl acetate and the combined organic layers were washed with brine and dried over sodium sulphate. Concentration under reduced pressure and purification by silica gel column chromatography using 40% ethyl acetate in hexane as eluent furnished title compound (0.1 g) as a colorless gummy mass. Yield: 41%; $^1$H NMR (300 MHz, CDCl$_3$): δ 8.42 (s, 1H), 8.06-7.99 (m, 3H), 7.47-7.02 (m, 7H), 6.55 (d, 1H, J=23.1 Hz), 6.28 (bs, 1H), 4.98-4.91 (m, 2H), 4.83-4.78 (m, 2H), 4.49-4.45 (m, 1H), 2.16 (s, 3H), 1.89 (d, 3H, J=2.4 Hz), 1.45 (d, 3H, J=23.1 Hz); Mass: [M+1]$^+$ 568 (100%); IR cm$^-$: 3414, 2931, 1751, 1619, 1276, 1230, 951, 712; HPLC: 95.2%.

Example 13

Preparation of ((2R,4R)-3-acetoxy-4-fluoro-3,4-dimethyl-5-(6-morpholino-9H-purin-9-yl)-tetrahydrofuran-2-yl)methyl benzoate

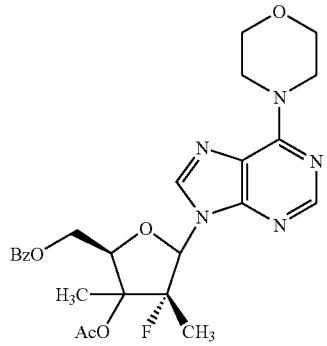

To a stirred solution of ((2R,4R)-3-acetoxy-5-(6-chloro-9H-purin-9-yl)-4-fluoro-3,4-dimethyl-tetrahydrofuran-2-yl) methyl benzoate (about 0.3 g, 0.64 mmol) in ethanol (about 5 ml) was added morpholine (about 0.56 ml, 6.49 mmol) and stirred at room temperature for about 15 hours. Completion of the reaction mixture monitored by thin-layer chromatography, water added to the reaction mixture and the aqueous layer was extracted with ethyl acetate and the combined organic layers were washed with brine and dried over sodium sulphate. Concentration under reduced pressure and purification by silica gel column chromatography using 40% ethyl acetate in hexane as eluent furnished title compounds Isomer A and B (0.1 g) as a colorless gummy mass. Yield: 30%.

Isomer A: $^1$H NMR (300 MHz, CDCl$_3$): δ 8.80 (s, 1H), 8.47 (d, 1H, J=5.1 Hz), 8.06-8.03 (m, 2H), 7.48-7.46 (m, 3H), 6.57 (d, 1H, J=23.4 Hz), 4.86-4.73 (m, 2H), 4.54-4.51 (m, 1H), 3.96-3.84 (m, 4H), 3.54-3.48 (m, 2H), 3.29-3.25 (m, 2H), 2.22 (s, 3H), 1.90 (d, 3H, J=2.4 Hz), 1.26 (d, 3H, J=22.8 Hz); Mass: [M+1]$^+$ 513 (100%), [M+Na]$^+$ 536 (35%); IR cm$^-$: 3407, 2804, 2176, 1739, 1625, 1465, 1273, 911, 713; HPLC: 72%.

Isomer B: $^1$H NMR (300 MHz, CDCl$_3$): δ 8.80 (s, 1H), 8.47 (d, 1H, J=4.1 Hz), 8.06-8.03 (m, 2H), 7.59-7.56 (m, 1H), 7.48-7.43 (m, 2H), 6.58 (d, 1H, J=23.4 Hz), 4.86-4.73 (m, 2H), 4.53-4.47 (m, 1H), 3.99-3.83 (m, 4H), 3.54-3.28 (m, 2H), 3.27-3.23 (m, 2H), 2.22 (s, 3H), 1.89 (d, 3H, J=2.1 Hz), 1.26 (d, 3H, J=22.8 Hz); ES Mass: [M+Na]$^+$: 536 (100%), [M+1]$^+$ 514 (20%); HPLC: 95.6%.

Example 14

Preparation of ((2R,4R)-3-acetoxy-5-(6-(cycloheptylamino)-9H-purin-9-yl)-4-fluoro-3,4-dimethyltetrahydrofuran-2-yl)methyl benzoate

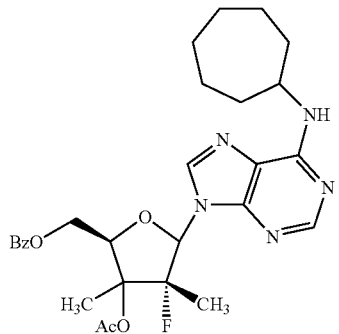

To a stirred solution of ((2R,4R)-3-acetoxy-5-(6-chloro-9H-purin-9-yl)-4-fluoro-3,4-dimethyl-tetrahydrofuran-2-yl)

methyl benzoate (about 0.55 g, 1.10 mmol) in ethanol (about 5 ml) was added cycloheptylamine (about 1.80 ml, 14.2 mmol) and refluxed for about 30 minutes. Completion of the reaction mixture monitored by thin-layer chromatography, water added to the reaction mixture and the aqueous layer was extracted with ethyl acetate and the combined organic layers were washed with brine and dried over sodium sulphate. Concentration under reduced pressure and purification by silica gel column chromatography using 40% ethyl acetate in hexane as eluent furnished title compound (0.4 g) as a colorless solid. Yield: 62%; $^1$H-NMR: $^1$H NMR (300 MHz, CDCl$_3$): δ 8.38 (s, 1H), 8.04 (d, 2H), 7.97 (s, 1H), 7.60-7.55 (m, 1H), 7.47-7.42 (m, 2H), 6.52 (d, 1H, J=22.2 Hz), 5.81 (bs, 1H), 4.83-4.77 (m, 2H), 4.48-4.41 (m, 1H), 2.15 (s, 3H), 1.89-1.88 (s, 3H), 1.62-1.11 (m, 16H); ES Mass: [M+1]$^+$ 540 (60%), [M+Na] 562 (100%); IR cm$^-$: 3430, 2924, 2853, 2348, 1753, 1725, 1617, 1451, 1274, 1060, 950, 711. HPLC: 92%.

Example 15

Preparation of (2R,4R)-5-(6-(cycloheptylamino)-9H-purin-9-yl)-4-fluoro-2-(hydroxymethyl)-3,4-dimethyl tetrahydrofuran-3-ol

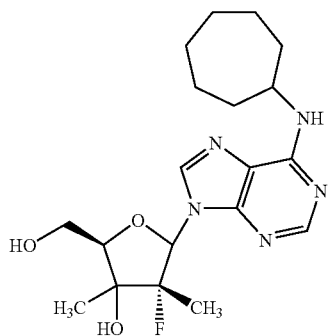

A solution of ((2R,4R)-3-acetoxy-5-(6-(cycloheptylamino)-9H-purin-9-yl)-4-fluoro-3,4-dimethyltetrahydrofuran-2-yl)methyl benzoate (about 0.3 g, 0.55 mmol) in methanolicammonia (25% w/w 10 ml) was stirred at room temperature for overnight. Completion of the reaction mixture monitored by thin-layer chromatography, water added to the reaction mixture and the aqueous layer was extracted with ethyl acetate and the combined organic layers were washed with brine and dried over sodium sulphate. Concentration under reduced pressure and purification by silica gel column chromatography using 25% ethyl acetate in hexane as eluent furnished title compound (0.17 g) as a colorless solid. Yield: 78%; $^1$H-NMR: $^1$H NMR (300 MHz, CDCl$_3$): δ 8.34 (s, 1H), 7.95 (d, 1H, J=3.6 Hz), 6.59 (d, 1H, J=22.5 Hz), 5.80 (bs, 1H), 5.24 (s, 1H), 4.28-4.20 (m, 4H), 2.14-2.09 (m, 1H), 1.59-1.25 (m, 18H); ES Mass: [M+1]$^+$ 394 (100%), 395 (30%); IR cm$^-$: 3364, 2928, 2855, 2358, 1758, 1618, 1378, 1101, 844, 750; HPLC: 98.16%.

Example 16

Preparation of (2R,4R)-5-(6-(cyclopropylamino)-9H-purin-9-yl)-4-fluoro-tetrahydro-2-(hydroxymethyl)-3,4-dimethylfuran-3-ol

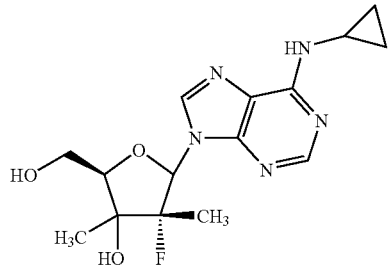

A solution of ((2R,4R)-3-acetoxy-5-(6-(cyclopropylamino)-9H-purin-9-yl)-4-fluoro-3,4-dimethyl-tetrahydrofuran-2-yl)methyl benzoate (about 0.25 g, 0.51 mmol) in methanolicammonia (25% w/w 5 ml) was stirred at room temperature for overnight. Completion of the reaction mixture monitored by thin-layer chromatography, water added to the reaction mixture and the aqueous layer was extracted with ethyl acetate and the combined organic layers were washed with brine and dried over sodium sulphate. Concentration under reduced pressure and purification by silica gel column chromatography using 25% ethyl acetate in hexane as eluent furnished title compound (0.14 g) as a colorless gummy mass. Yield: 80%; $^1$H-NMR: $^1$H NMR (300 MHz, CDCl$_3$): δ 8.45 (s, 1H), 8.01 (d, 1H, J=3.3 Hz), 6.60 (d, 1H, J=22.8 Hz), 6.36 (bs, 1H), 4.30-4.29 (m, 1H), 4.23-4.08 (m, 3H), 3.04 (m, 1H), 1.37 (s, 3H), 1.26 (d, 3H, J=2.4 Hz), 0.95-0.92 (m, 2H), 0.68 (m, 2H); ES Mass: [M+1]$^+$338 (100%); IR cm$^-$: 3512, 3055, 2933, 1745, 1384, 1113, 742, 703; HPLC: 93%.

Example 17

Preparation of ((2R,4R)-3-acetoxy-5-(6-(cyclopentylamino)-9H-purin-9-yl)-4-fluoro-3,4-dimethyltetrahydrofuran-2-yl)methyl benzoate

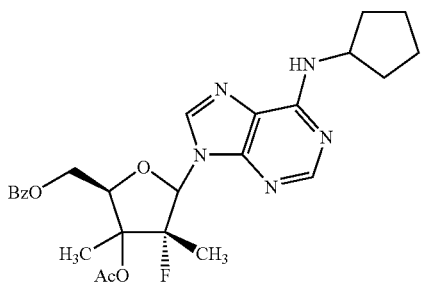

To a stirred solution of ((2R,4R)-3-acetoxy-5-(6-chloro-9H-purin-9-yl)-4-fluoro-3,4-dimethyl-tetrahydrofuran-2-yl) methyl benzoate (about 0.50 g, 1.08 mmol) in ethanol (about 5 ml) was added cyclopentylamine (about 1.28 ml, 12.9 mmol) and refluxed for about 30 minutes. Completion of the reaction mixture monitored by thin-layer chromatography, water added to the reaction mixture and the aqueous layer was extracted with ethyl acetate and the combined organic layers were washed with brine and dried over sodium sulphate. Concentration under reduced pressure and purification by silica gel column chromatography using 6% methanol in dichloromethane as eluent furnished title compound (0.42 g) as a colorless solid. Yield: 76%; $^1$H-NMR: $^1$H NMR (300 MHz, CDCl$_3$): δ 8.39 (s, 1H), 8.06-7.96 (m, 3H), 7.57-7.42

(m, 3H), 6.54 (d, 1H, J=23.1 Hz), 5.92 (d, 1H, J=7.5 Hz), 4.83-4.77 (m, 2H), 4.48-4.44 (m, 1H), 2.15 (s, 3H), 2.08-1.91 (m, 1H), 1.89-1.88 (d, 3H, J=2.1 Hz), 1.78-1.58 (m, 8H), 1.44 (d, 3H, J=23.1 Hz); ES Mass: [M+1]$^+$ 526 (20%), [M+Na] 548 (100%); IR cm$^-$: 3437, 2925, 2855, 1733, 1612, 1232, 1059, 951, 711; HPLC: 98%.

Example 18

Preparation of ((2R,4R)-3-acetoxy-5-(6-(cyclohexy-lamino)-9H-purin-9-yl)-4-fluoro-3,4-dimethyltet-rahydrofuran-2-yl)methyl benzoate

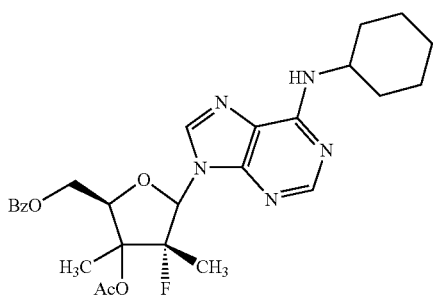

To a stirred solution of ((2R,4R)-3-acetoxy-5-(6-chloro-9H-purin-9-yl)-4-fluoro-3,4-dimethyl-tetrahydrofuran-2-yl) methyl benzoate (about 0.50 g, 1.08 mmol) in ethanol (about 5 ml) was added cyclohexylamine (about 1.48 ml, 12.9 mmol) and refluxed for about 30 minutes. Completion of the reaction mixture monitored by thin-layer chromatography, water added to the reaction mixture and the aqueous layer was extracted with ethyl acetate and the combined organic layers were washed with brine and dried over sodium sulphate. Concentration under reduced pressure and purification by silica gel column chromatography using 6% methanol in dichloromethane as eluent furnished title compound (0.42 g) as a colorless solid. Yield: 74%; $^1$H-NMR: $^1$H NMR (300 MHz, CDCl$_3$): δ 8.38 (s, 1H), 8.06-7.96 (m, 3H), 7.58-7.42 (m, 3H), 6.54 (d, 1H, J=23.1 Hz), 5.77 (d, 1H, J=8.1 Hz), 4.83-4.78 (m, 2H), 4.48-4.41 (m, 1H), 2.16 (s, 3H), 2.13-1.77 (m, 14H), 1.45 (d, 3H, J=23.1 Hz); ES Mass: [M+1]$^+$ 512 (20%), [M+Na] 534 (100%); IR cm$^-$: 3414, 2926, 2854, 1724, 1618, 1229, 1063, 950, 712; HPLC: 98%.

Example 19

Preparation of ((2R,4R)-3-acetoxy-5-(2,4-dioxo-3,4-dihydropyrimidin-1(2H)-yl)-4-fluoro-3,4-dimethyl-tetrahydrofuran-2-yl)methyl benzoate

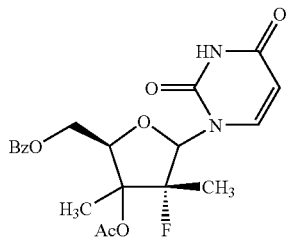

To a stirred solution of uracil (about 0.30 g, 2.71 mmol) in acetonitrile (about 7 ml) was added N,O-Bis(trimethylsilyl) acetamide at room temperature (about 4 ml, 16.3 mmol) and refluxed for about 2 hours. To this added ((2R,4R)-3,5-diacetoxy-4-fluoro-3,4-dimethyl-tetrahydrofuran-2-yl)methyl benzoate (about 0.5 gm, 1.35 mmol) in acetonitrile (about 8 ml) drop wise at about 0° C., and added SnCl$_4$ (about 0.2 ml, 2.03 mmol) and refluxed for about 15 hours, Completion of the reaction monitored by thin-layer chromatography and neutralized the reaction mixture with saturated sodium bicarbonate solution. Aqueous layer was extracted with ethyl acetate and the combined organic layers were washed with brine and dried over sodium sulphate. Concentration under reduced pressure and purification by silica gel column chromatography using 35% ethyl acetate/hexane as eluent furnished title compound (0.35 g) as a colorless solid. Yield: 61%; $^1$H-NMR: $^1$H NMR (300 MHz, CDCl$_3$): δ 8.67 (s, 1H), 8.06-8.03 (m, 2H), 7.59-7.33 (m, 4H), 6.39 (d, 1H, J=22.8 Hz), 5.76, 5.55 (dd, 1H, J=2.1 Hz, J=2.4 Hz), 4.80-4.43 (m, 3H), 2.13 (s, 3H), 1.81 (d, 3H, J=2.4 Hz), 1.49 (d, 3H, J=23.4 Hz); ES Mass: [M+Na] 443 (100%); IR cm$^-$: 3433, 2931, 2346, 1713, 1385, 1274, 952, 712; HPLC: 96%.

Example 20

Preparation of ((2R,4R)-3-acetoxy-4-fluoro-3,4-dimethyl-5-(5-methyl-2,4-dioxo-3,4-dihydropyrimidin-1(2H)-yl)-tetrahydrofuran-2-yl)methyl acetate

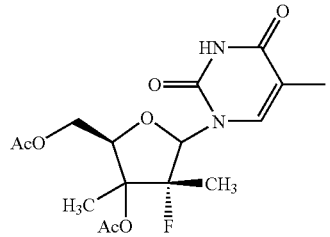

To a stirred solution of thymine (about 0.31 g, 2.48 mmol) in acetonitrile (about 6 ml) was added N,O-Bis(trimethylsilyl)acetamide at room temperature (about 3.6 ml, 16.3 mmol) and refluxed for about 2 hours. To this added ((2R,4R)-3,5-diacetoxy-4-fluoro-3,4-dimethyl-tetrahydrofuran-2-yl)methyl benzoate (about 0.38 gm, 1.24 mmol) in acetonitrile (about 6 ml) drop wise at about 0° C., and added SnCl$_4$ (about 0.2 ml, 1.86 mmol) then refluxed for about 15 hours. Completion of the reaction mixture monitored by thin-layer chromatography and neutralized the reaction mixture with saturated sodium bicarbonate solution. Aqueous layer was extracted with ethyl acetate and the combined organic layers were washed with brine, dried over sodium sulphate. Concentration under reduced pressure and purification by silica gel column chromatography using 60% ethyl acetate/hexane as eluent furnished title compound (0.14 g) as a colorless solid. Yield: 30%; $^1$H-NMR: $^1$H NMR (300 MHz, CDCl$_3$): δ 8.22 (s, 1H), 7.13-7.12 (m, 1H), 6.34 (d, 1H, J=23.4 Hz), 4.59-4.50 (m, 2H), 4.16-4.09 (m, 1H), 2.94 (d, 3H, J=22.2 Hz), 2.12 (s, 3H), 1.95 (s, 3H), 1.77 (d, 3H, J=2.4 Hz), 1.55 (d, 3H, J=30 Hz); ES Mass: [M+1] 373 (10%), [M+Na] 395 (100%).

Example 21

Preparation of ((2R,4R)-3-acetoxy-5-(4-benzamido-2-0x0pyrimidin-1(2H)-yl)-4-fluoro-3,4-dimethyl-tetrahydrofuran-2-yl)methyl benzoate

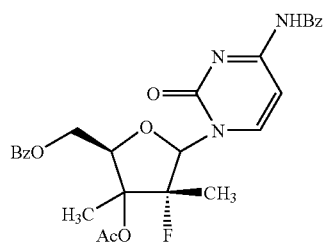

To a stirred solution of N-benzoylcytisine (about 0.40 g, 1.90 mmol) in acetonitrile (about 6 ml) was added N,O-Bis(trimethylsilyl)acetamide at room temperature (about 2.8 ml, 11.4 mmol) and refluxed for about 2 hours. To this added ((2R,4R)-3,5-diacetoxy-4-fluoro-3,4-dimethyl-tetrahydrofuran-2-yl)methyl benzoate (about 0.35 gm, 0.95 mmol) in acetonitrile (about 6 ml) drop wise at about 0° C. and added SnCl$_4$ (about 0.16 ml, 1.42 mmol) and refluxed for about 15 hours. Completion of the reaction mixture monitored by thin-layer chromatography and neutralized the reaction mixture with saturated sodium bicarbonate solution. Aqueous layer was extracted with ethyl acetate and the combined organic layers were washed with brine and dried over sodium sulphate. Concentration under reduced pressure and purification by silica gel column chromatography using 50% ethyl acetate/hexane as eluent furnished title compound (0.25 g) as a colorless solid. Yield: 50%; $^1$H-NMR: $^1$H NMR (300 MHz, CDCl$_3$): δ 8.06 (d, 2H, J=7.2 Hz), 7.90 (d, 2H, J=3.78 Hz), 7.81-7.80 (m, 2H), 7.63-7.45 (m, 9H), 6.66 (d, 1H, J=22.2 Hz), 4.81-4.49 (m, 3H), 2.31 (s, 3H), 2.12 (s, 3H), 1.83 (d, 3H, J=2.4 Hz), 1.53 (d, 3H); ES Mass: [M+Na] 546 (100%), [M+1]$^+$ 524 (50%).

Example 22

Preparation of 1-((2R,4R)-3-fluoro-tetrahydro-4-hydroxy-5-(hydroxymethyl)-3,4-dimethylfuran-2-yl)pyrimidine-2,4(1H,3H)-dione

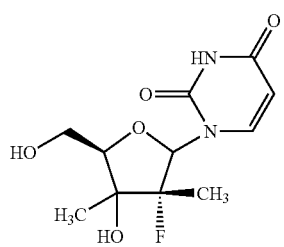

A solution of ((2R,4R)-3-acetoxy-5-(2,4-dioxo-3,4-dihydropyrimidin-1(2H)-yl)-4-fluoro-3,4-dimethyl-tetrahydrofuran-2-yl)methyl benzoate (about 0.25 g, 0.59 mmol) in methanolic ammonia (25% w/w 10 ml) was stirred at room temperature for overnight. Completion of the reaction mixture monitored by thin-layer chromatography and methanol was removed under reduced pressure. Water added to the crude and extracted with ethyl acetate and the organic layer was dried over sodium sulphate. Concentration under reduced pressure and purification by silica gel column chromatography using 5% methanol in dichloromethane to elude title compound (0.09 g). Yield: 55%; $^1$H-NMR: $^1$H NMR (300 MHz, CDCl$_3$): δ 8.57 (bs, 1H), 7.38-7.33 (m, 1H), 6.44 (d, 1H, J=22.2 Hz), 5.73 (d, 1H, J=8.1 Hz), 4.65 (bs, 1H), 4.19-4.09 (m, 3H), 2.86 (bs, 1H), 1.48 (s, 3H), 1.35 (d, 3H, J=2.6 Hz); ES Mass: [M+Na]$^+$: 297 (20%), [M+1]$^+$ 275 (20%); IR cm$^-$: 3430 2928, 2864, 2273, 1707, 1385, 1270, 1052, 821, 567; HPLC: 93.2%.

Example 23

Preparation of 4-amino1-((2R,4R)-3-fluoro-tetrahydro-4-hydroxy-5-(hydroxymethyl)-3,4-dimethylfuran-2-yl)pyrimidin-2(1H)-one

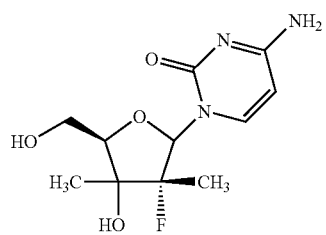

A solution of ((2R,4R)-3-acetoxy-5-(4-benzamido-2-oxopyrimidin-1(2H)-yl)-4-fluoro-3,4-dimethyl-tetrahydrofuran-2-yl)methyl benzoate (about 0.22 g, 0.42 mmol) in methanolic ammonia (25% w/w 15 ml) was stirred at room temperature for overnight. Completion of the reaction mixture monitored by thin-layer chromatography and methanol was removed under reduced pressure. Water added to the crude and extracted with ethyl acetate and the organic layer was dried over sodium sulphate. Concentration under reduced pressure and purification by silica gel column chromatography using 15% methanol in dichloromethane to elude title compound (0.047 g). Yield: 46%; $^1$H-NMR: $^1$H NMR (300 MHz, CDCl$_3$): δ 7.40 (dd, 1H, J1=7.5 Hz, J2=7.5 Hz), 7.25-7.17 (bs, 2H), 6.23 (d, 1H, J=23.4 Hz), 5.72 (d, 1H, J=7.5 Hz), 5.53 (s, 1H), 4.79 (t, 1H), 4.11-4.09 (m, 1H), 3.49-3.45 (m, 2H), 1.29-1.19 (m, 6H); ES Mass: [M+1]$^+$ 274 (100%), [M+2]$^+$ 275 (60%); IR cm$^-$: 3459, 2927, 2855, 2274, 1635, 1028, 938, 724, 471.

Example 24

Preparation of 1-((2R,4R)-3-fluoro-4-hydroxy-5-(hydroxymethyl)-3,4-dimethyl-tetrahydrofuran-2-yl)-5-methylpyrimidine-2,4(1H,3H)-dione

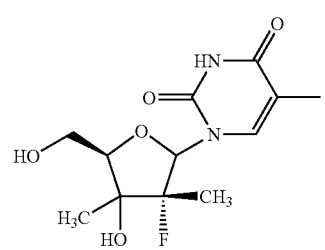

A solution of ((2R,4R)-3-acetoxy-4-fluoro-3,4-dimethyl-5-(5-methyl-2,4-dioxo-3,4-dihydropyrimidin-1(2H)-yl)-tetrahydrofuran-2-yl)methyl benzoate (about 0.11 g, 0.29 mmol) in methanolic ammonia (25% w/w 10 ml) was stirred at room temperature for overnight. Completion of the reaction mixture monitored by thin-layer chromatography and methanol was removed under reduced pressure. Water added to the crude and extracted with ethyl acetate and the organic layer was dried over sodium sulphate. Concentration under reduced pressure and purification by silica gel column chromatography using 5% methanol in dichloromethane to elude title compound (0.020 g). Yield: 23.5%; $^1$H-NMR: $^1$H NMR (300 MHz, CDCl$_3$): δ 8.18 (s, 1H), 7.18 (bs, 1H), 6.45 (d, 1H, J=21 Hz), 4.53-4.15 (m, 4H), 2.67-2.38 (m, 1H), 2.38 (s, 3H), 1.68-1.42 (m, 6H); ES Mass: [M+Na]$^+$ 311 (100%);

Example 25

Preparation of ((2R,4R)-3-acetoxy-5-(6-(cyclopropylmethylamino)-9H-purin-9-yl)-4-fluoro-3,4-dimethyltetrahydrofuran-2-yl)methyl benzoate

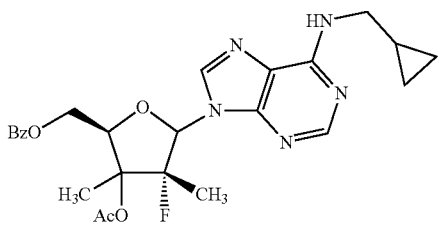

To a stirred solution of ((2R,4R)-3-acetoxy-5-(6-chloro-9H-purin-9-yl)-4-fluoro-3,4-dimethyl-tetrahydrofuran-2-yl)methyl benzoate (about 0.30 g, 0.64 mmol) in ethanol (about 5 ml) was added 1,8-Diazabicyclo[5.4.0]undec-7-ene (about 0.14 ml, 0.97 mmol) and aminomethyl cyclopropane hydrochloride (about 0.14 g, 1.2 mmol) at room temperature and refluxed for about 30 minutes. Completion of the reaction monitored by thin-layer chromatography, water added to the reaction mixture and the aqueous layer was extracted with ethyl acetate and the combined organic layers were washed with water, brine and dried over sodium sulphate. Concentration under reduced pressure and purification by silica gel column chromatography using 5% methanol in dichloromethane as eluent furnished title compound (0.23 g) as a colorless solid. Yield: 67%; $^1$H NMR (300 MHz, CDCl$_3$): δ 8.39 (s, 1H), 8.06-8.04 (m, 2H), 7.99 (d, 1H, J=3.6 Hz), 7.60-7.55 (m, 1H), 7.47-7.42 (m, 2H), 6.54 (d, 1H, J=23.1 Hz), 5.93 (bs, 1H), 4.84-4.78 (m, 2H), 4.49-4.42 (m, 1H), 3.49 (bs, 2H), 2.16 (s, 3H), 1.89 (d, 3H, J=2.4 Hz), 1.44 (d, 3H, J=23.1 Hz), 1.19-1.08 (m, 1H), 0.59-0.55 (m, 2H), 0.34-0.31 (m, 2H); ES Mass: [M+1]$^+$ 498 (100%), [M+Na] 520 (45%); HPLC: 96%.

Example 26

Preparation of ((2R,4R)-3-acetoxy-5-(2-amino-6-chloro-9H-purin-9-yl)-4-fluoro-3,4-dimethyltetrahydrofuran-2-yl)methyl benzoate

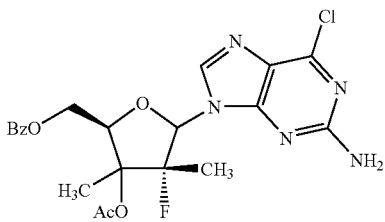

To a stirred solution of 6-chloro-9H-purin-2-amine (about 0.18 g, 1.08 mmol) in acetonitrile (about 6 ml) was added N,O-Bis(trimethylsilyl)acetamide (about 1.59 ml, 6.5 mmol) at room temperature and refluxed for about 2 hours. To this added (2R,4R)-5-(benzoyloxymethyl)-3-fluoro-3,4-dimethyltetrahydrofuran-2,4-diyl diacetate (about 0.20 g, 0.54 mmol) in acetonitrile (about 6 ml) drop wise at about 0° C., and added SnCl$_4$ (about 0.09 ml, 0.81 mmol) then refluxed for about 2 hours. Completion of the reaction monitored by thin-layer chromatography and neutralized the reaction mixture with saturated sodium bicarbonate solution. Aqueous layer was extracted with ethyl acetate and the combined organic layers were washed with water, brine and dried over sodium sulphate. Concentration under reduced pressure and purification by silica gel column chromatography using 2% methanol in dichloromethane as eluent furnished title compound (0.8 g) as a colorless solid. Yield: 33%; $^1$H NMR (300 MHz, CDCl$_3$): δ 8.29 (d, 1H, J=4.2 Hz), 8.06-8.03 (m, 2H), 7.59-7.56 (m, 1H), 7.49-7.44 (m, 2H), 6.80 (d, 1H, J=21.6 Hz), 5.09 (s, 2H), 4.83-4.78 (m, 2H), 4.51-4.44 (m, 1H), 2.17 (s, 3H), 1.89 (d, 3H, J=2.4 Hz), 1.48 (d, 3H, J=23.1 Hz); ES Mass: [M+1] 478 (30%), [M+Na] 500 (30%); HPLC:. 93.1%.

Example 27

Preparation of (2R,4R)-5-(6-(cyclopentylamino)-9H-purin-9-yl)-4-fluoro-2-(hydroxymethyl)-3,4-dimethyltetrahydrofuran-3-ol

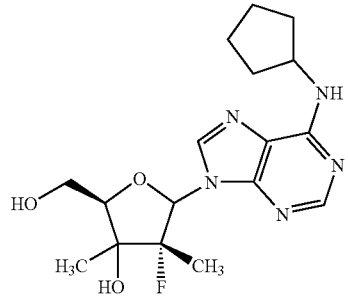

A solution of ((2R,4R)-3-acetoxy-5-(6-(cyclopentylamino)-9H-purin-9-yl)-4-fluoro-3,4-dimethyltetrahydrofuran-2-yl)methyl benzoate (about 0.31 g, 0.60 mmol) in methanolic ammonia (25% w/w 15 ml) was stirred at room temperature for overnight. Completion of the reaction monitored by thin-layer chromatography and methanol was removed under reduced pressure then water added to the crude and extracted with ethyl acetate. The organic layer was dried over sodium sulphate, concentrated under reduced pressure and purified by silica gel column chromatography using 5% methanol in dichloromethane to afford the title compound (0.2 g) as a colorless solid. Yield: 90%; $^1$H NMR (300 MHz, CDCl$_3$): δ 8.33 (s, 1H), 7.92 (d, 1H, J=3.6 Hz), 6.62 (d, 1H, J=22.2 Hz), 5.83 (bs, 1H), 5.55 (s, 1H), 5.43 (bs, 1H), 4.58 (bs, 1H), 4.25-4.21 (m, 2H), 4.14-4.10 (m, 1H), 2.15-2.09 (m, 1H), 1.78-1.52 (m, 8H), 1.42-1.25 (m, 6H); ES Mass: [M+1]$^+$ 366 (100%), 367 (45%); IR cm$^-$: 3306, 2959, 1624, 1475, 1232, 1056, 938, 812; HPLC: 98.2%.

Example 28

Preparation of (2R,4R)-5-(6-(cyclohexylamino)-9H-purin-9-yl)-4-fluoro-2-(hydroxymethyl)-3,4-dimethyltetrahydrofuran-3-ol

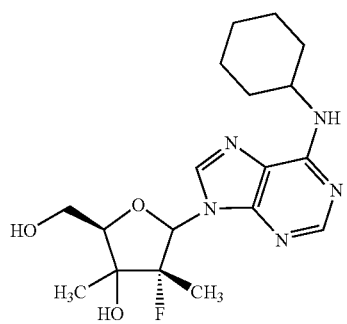

A solution of ((2R,4R)-3-acetoxy-5-(6-(cyclohexylamino)-9H-purin-9-yl)-4-fluoro-3,4-dimethyltetrahydrofuran-2-yl)methyl benzoate (about 0.32 g, 0.60 mmol) in methanolic ammonia (25% w/w 15 ml) was stirred at room temperature for overnight. Completion of the reaction monitored by thin-layer chromatography and methanol was removed under reduced pressure then water added to the crude and extracted with ethyl acetate. The organic layer was dried over sodium sulphate, concentrated under reduced pressure and purified by silica gel column chromatography using 5% Methanol in dichloromethane to elude title compound (0.2 g) as a colorless solid. Yield: 86%; $^1$H NMR (300 MHz, CDCl$_3$): δ 8.32 (s, 1H), 7.93 (d, 1H, J=3.3 Hz), 6.60 (d, 1H, J=22.5 Hz), 5.79 (bs, 1H), 5.51 (s, 1H), 5.23 (bs, 1H), 4.25-4.13 (m, 3H), 2.17-2.04 (m, 1H), 1.76-1.52 (m, 16H); ES Mass: [M+1]$^+$ 380 (100%), 381 (45%); IR cm$^-$: 3338, 2928, 2854, 1624, 1475, 1226, 1062, 938, 740; HPLC: 97.8%.

Example 29

Preparation of ((2R,4R)-3-acetoxy-5-(6-(benzylamino)-9H-purin-9-yl)-4-fluoro-3,4-dimethyltetrahydrofuran-2-yl)methyl benzoate

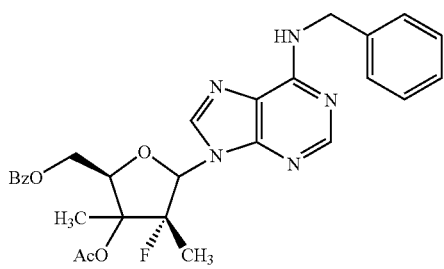

To a stirred solution of ((2R,4R)-3-acetoxy-5-(6-chloro-9H-purin-9-yl)-4-fluoro-3,4-dimethyl-tetrahydrofuran-2-yl)methyl benzoate (about 0.2 g, 0.43 mmol) in ethanol (about 8 ml) was added benzylamine (about 0.56 ml, 5.19 mmol) and refluxed for about 30 minutes. Completion of the reaction monitored by thin-layer chromatography, water added to the reaction mixture and the aqueous layer was extracted with ethyl acetate. The combined organic layers were washed with brine and dried over sodium sulphate. Concentration under reduced pressure and purification by silica gel column chromatography using 3% methanol in dichloromethane as eluent furnished title compound (0.22 g) as a colorless solid. Yield: 97%; $^1$H NMR (300 MHz, CDCl$_3$): δ 8.44 (s, 1H), 8.13-7.96 (m, 3H), 7.59-7.57 (m, 1H), 7.49-7.28 (m, 7H), 6.57 (d, 1H, J=23.1 Hz), 6.24 (bs, 1H), 4.89-4.79 (m, 3H), 4.50-4.43 (m, 1H), 2.18 (s, 3H), 1.90 (d, 3H, J=2.1 Hz), 1.47 (d, 3H, J=23.1 Hz); Mass: [M+1]$^+$ 534 (85%), [M+Na]$^+$ 556 (100%). IR cm$^-$: 3385, 1751, 1720, 1619, 1528, 1476, 1369, 1274, 1062, 712; HPLC: 95%.

Example 30

Preparation of (2R,4R)-5-(6-(cyclopropylmethylamino)-9H-purin-9-yl)-4-fluoro-2-(hydroxymethyl)-3,4-dimethyltetrahydrofuran-3-ol

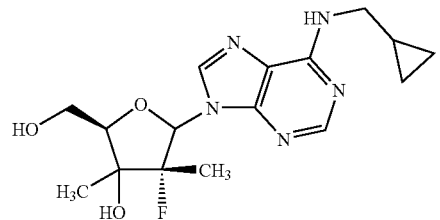

To a solution of ((2R,4R)-3-acetoxy-5-(6-(cyclopropylmethylamino)-9H-purin-9-yl)-4-fluoro-3,4-dimethyltetrahydrofuran-2-yl)methyl benzoate (about 0.13 g, 0.26 mmol) in methanolicammonia (25% w/w 5 ml) was stirred at room temperature for overnight and completion of the reaction monitored by thin-layer chromatography. Methanol was removed under reduced pressure, water added to the crude and extracted with ethyl acetate. The organic layer was dried over sodium sulphate, concentrated under reduced pressure and purified by silica gel column chromatography using 5% methanol in dichloromethane to elude title compound (0.07 g) as a colorless solid. Yield: 82%; $^1$H NMR (300 MHz, CDCl$_3$): δ 8.34 (s, 1H), 7.97 (d, 1H, J=3.3 Hz), 6.60 (d, 1H, J=22.5 Hz), 6.00 (bs, 1H), 5.34 (s, 1H), 4.49 (bs, 1H), 4.28-4.13 (m, 3H), 3.49 (bs, 2H), 1.43-1/36 (m, 6H), 1.14-1.11 (m, 1H), 0.59-0.56 (m, 2H), 0.32-0.30 (m, 2H); ES Mass: [M+1]$^+$ 352 (100%); HPLC: 93%.

Example 31

Preparation of ((2R,4R)-5-(2,4-dioxo-3,4-dihydropyrimidin-1(2H)-yl)-4-fluoro-3-hydroxy-3,4-dimethyltetrahydrofuran-2-yl)methyl butyrate

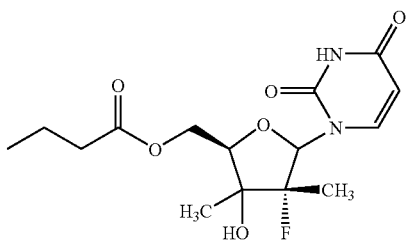

To a solution of 1-((2R,4R)-3-fluoro-4-hydroxy-5-(hydroxymethyl)-3,4-dimethyltetrahydrofuran-2-yl)pyrimidine-2,4(1H,3H)-dione (about 0.30 g, 1.09 mmol) in dichloromethane (about 5 ml) was added solution of butyroylchloride (about 0.28 ml, 2.70 mmol) in dichloromethane (about 5 ml) at about 0° C. and stirred at room temperature for overnight. Completion of the reaction monitored by thin-layer chromatography, water added to the reaction mixture and extracted with dichloromethane and the combined organic layers were washed with saturated sodium bicarbonate, dried over sodium sulphate and concentrated under reduced pressure. The residue was purified by silica gel column chromatography using 2% methanol in dichloromethane to elude title compound (0.15 g) as a colorless solid. Yield: 40%; $^1$H NMR (300 MHz, CDCl$_3$): δ 8.42 (bs, 1H), 7.39-7.35 (dd, 1H, J1=8.4 Hz, J2=8.1 Hz), 6.37 (d, 1H, J=22.8 Hz), 5.76-5.73 (dd, 1H, J1=8.4 Hz, J2=8.1 Hz), 4.58-4.52 (m, 1H), 4.39-4.37 (m, 1H), 4.26-4.20 (m, 1H), 2.68 (s, 1H), 2.38-2.33 (t, 2H), 1.69-1.61 (m, 2H), 1.48-1.25 (m, 6H), 0.99-0.94 (t, 3H); ES Mass: [M+Na]$^+$: 367 (100%), [M+1]$^+$ 345 (30%); IR cm$^-$: 3504, 3147, 1725, 1677, 1560, 1180, 1086, 1062, 994; HPLC: 99%.

Example 32

Preparation of ((2R,4R)-5-(2,4-dioxo-3,4-dihydropyrimidin-1(2H)-yl)-4-fluoro-3-hydroxy-3,4-dimethyltetrahydrofuran-2-yl)methyl pentanoate

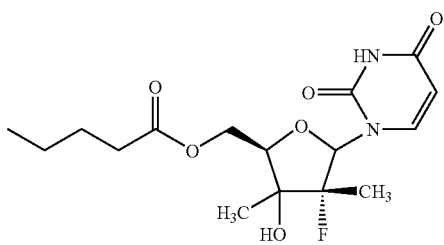

To a solution of 1-((2R,4R)-3-fluoro-4-hydroxy-5-(hydroxymethyl)-3,4-dimethyltetrahydrofuran-2-yl)pyrimidine-2,4(1H,3H)-dione (about 0.30 g, 1.09 mmol) in dichloromethane (about 5 ml) was added a solution of valeroylchloride (about 0.33 ml, 2.70 mmol) in dichloromethane (about 5 ml) at about 0° C. and stirred at room temperature for overnight. Completion of the reaction monitored by thin-layer chromatography, water added to the reaction mixture and extracted with dichloromethane and the combined organic layers were washed with saturated sodium bicarbonate, dried over sodium sulphate and concentrated under reduced pressure. The residue was purified by silica gel column chromatography using 2% methanol in dichloromethane to elude title compound (0.10 g) as a colorless solid. Yield: 27%; $^1$H NMR (300 MHz, CDCl$_3$): δ 8.31 (bs, 1H), 7.39-7.35 (dd, 1H, J1=8.1 Hz, J2=8.4 Hz), 6.36 (d, 1H, J=22.5 Hz), 5.76-5.72 (dd, 1H, J1=8.1 Hz, J2=8.4 Hz), 4.58-4.52 (m, 1H), 4.40-4.36 (m, 1H), 4.26-4.20 (m, 1H), 2.64 (s, 1H), 2.40-2.35 (t, 2H), 1.65-1.59 (m, 2H), 1.44 (d, 3H, J=23.1 Hz), 1.37-1.25 (m, 5H), 0.95-0.90 (t, 3H); ES Mass: [M+Na]$^+$: 381 (100%), [M+1]$^+$ 359 (40%); IR cm$^-$: 3504, 3145, 1710, 1676, 1560, 1265, 1180, 1039, 938, 824; HPLC: 99%.

Example 33

Preparation of ((2R,4R)-3-acetoxy-4-fluoro-3,4-dimethyl-5-(6-oxo-1H-purin-9(6H)-yl)tetrahydrofuran-2-yl)methyl benzoate

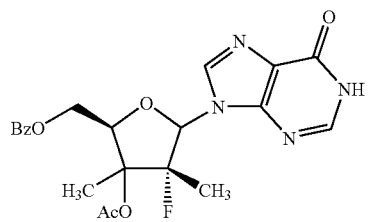

To a stirred solution of ((2R,4R)-3-acetoxy-5-(6-chloro-9H-purin-9-yl)-4-fluoro-3,4-dimethyl-tetrahydrofuran-2-yl)methyl benzoate (about 0.55 g, 1.19 mmol) in ethanol (about 15 ml) was added aminomethyl cyclopropane hydrochloride (about 1.50 g, 14.2 mmol) at room temperature and refluxed for about 24 hours. Completion of the reaction monitored by thin-layer chromatography, water added to the reaction mixture and the aqueous layer was extracted with ethyl acetate. The combined organic layers were washed with brine and dried over sodium sulphate, Concentration under reduced pressure and purification by silica gel column chromatography using 3% methanol in dichloromethane as eluent furnished title compound (0.4 g) as a colorless solid. Yield: 67%; $^1$H NMR (300 MHz, CDCl$_3$): δ 12.74 (bs, 1H), 8.16 (s, 1H), 8.06-8.03 (m, 3H), 7.65-7.50 (t, 1H), 7.48-7.45 (m, 2H), 7.47-7.42 (m, 2H), 6.45 (d, 1H, J=22.5 Hz), 4.84-4.78 (m, 2H), 4.47-4.45 (m, 1H), 2.18 (s, 3H), 1.90 (s, 3H), 1.44 (d, 3H, J=22.8 Hz), 1.19-1.08 (m, 1H), 0.59-0.55 (m, 2H), 0.34-0.31 (m, 2H); ES Mass: [M+1]$^+$ 445 (20%), [M+Na] 467 (45%); IR cm$^-$: 3431, 2920, 1746, 1726, 1588, 1372, 1278, 1113, 1094, 950, 829; HPLC: 98%.

Example 34

Preparation of 9-((3R,5R)-3-fluoro-4-hydroxy-5-(hydroxymethyl)-3,4-dimethyl-tetrahydrofuran-2-yl)-1H-purin-6(9H)-one

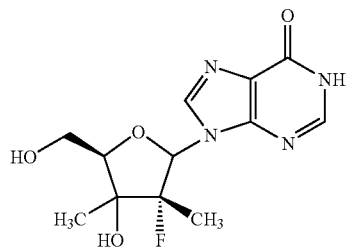

To a solution of ((2R,4R)-3-acetoxy-4-fluoro-3,4-dimethyl-5-(6-oxo-1H-purin-9(6H)-yl)tetrahydrofuran-2-yl) methyl benzoate (about 0.30 g, 0.67 mmol) in methanolic ammonia (25% w/w, 10 ml) was stirred at room temperature for overnight. Completion of the reaction monitored by thin-layer chromatography, methanol was removed under reduced pressure, water added to the crude and extracted with ethyl acetate. The organic layer was dried over sodium sulphate, concentrated under reduced pressure and purified by silica gel column chromatography using 5% methanol in dichloromethane to elude title compound (0.07 g) as a colorless solid. Yield: 35%; $^1$H NMR (300 MHz, CD$_3$OD): δ 8.14 (d, 1H, J=3.6 Hz), 8.06 (s, 1H), 6.41 (d, 1H, J=21.9 Hz), 4.43-

4.40 (m, 1H), 3.88-3.83 (m, 2H), 1.38-1.28 (m, 6H); Mass: [M+1]⁺ 299 (100%), [M+Na]⁺321 (30%); HPLC: 95.2%.

Example 35

Preparation of ((2R,4R)-3-acetoxy-4-fluoro-3,4-dimethyl-5-(5-methyl-2,4-dioxo-3,4-dihydropyrimidin-1(2H)-yl)tetrahydrofuran-2-yl)methyl benzoate

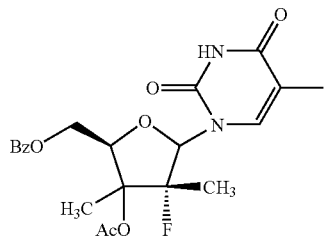

To a stirred solution of thymine (about 0.68 g, 5.43 mmol) in acetonitrile (about 15 ml) was added compound N,O-Bis-trimethylsilylacetamide (7.90 ml, 32.6 mmol) at room temperature and refluxed for about 2 hours. To this added (2R, 4R)-5-(benzoyloxymethyl)-3-fluoro-3,4-dimethyltetrahydrofuran-2,4-diyl diacetate (about 1.00 g, 2.71 mmol) in acetonitrile (about 15 ml) drop wise at about 0° C. and SnCl₄ (about 0.47 ml, 4.00 mmol) then refluxed for about 15 hours. Completion of the reaction monitored by thin-layer chromatography, neutralized the reaction mixture with saturated sodium bicarbonate, aqueous layer was extracted with ethyl acetate and the combined organic layers were washed with brine and dried over sodium sulphate. Concentrated under reduced pressure and purified by silica gel column chromatography using 3% methanol in dichloromethane as eluent furnished title compound (0.40 g) as a colorless solid. Yield: 34%; ¹H NMR (300 MHz, CDCl₃): δ 8.07 (s, 1H), 8.05-8.04 (m, 2H), 7.60-7.58 (m, 1H), 7.49-7.44 (m, 2H), 7.15-7.13 (m, 1H), 6.38 (d, 1H, J=23.1 Hz), 4.74-4.65 (m, 2H), 4.49-4.41 (m, 1H), 2.12 (s, 3H), 1.94 (d, 3H, J=0.9 Hz), 1.83 (d, 3H, J=2.4 Hz), 1.48 (d, 3H, J=23.4 Hz); ES Mass: [M+1] 435 (30%), [M+Na] 457 (100%); IR cm⁻: 3432, 2926, 1753, 1692, 1602, 1547, 1384, 1276, 1115, 954, 833; HPLC:. 92%.

The following compounds were also prepared similarly by the above procedures:

Example 36

((2R,4R)-5-(2,4-dioxo-3,4-dihydropyrimidin-1(2H)-yl)-4-fluoro-3-hydroxy-3,4-dimethyltetrahydrofuran-2-yl)methyl isobutyrate

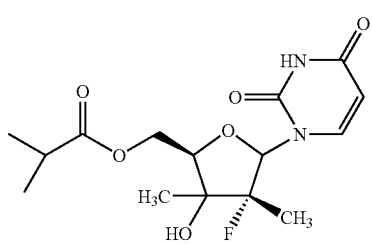

¹H NMR (300 MHz, CDCl₃): δ 8.96 (bs, 1H), 7.39-7.35 (dd, 1H, J1=8.1 Hz, J2=8.4 Hz), 6.88 (d, 1H, J=22.8 Hz), 5.75 (d, 1H, J=8.4 Hz), 4.57-4.51 (m, 1H), 4.38-4.37 (m, 1H), 4.26-4.20 (m, 1H), 3.05 (s, 1H), 2.64-2.59 (m, 1H), 1.44 (d, 3H, J=22.8 Hz), 1.35 (d, 3H, J=2.1 Hz), 1.21-1.18 (m, 6H); ES Mass: [M+Na]⁺: 367 (100%), [M+1]⁺ 345 (20%); IR cm⁻: 3594, 3414, 2871, 1721, 1688, 1619, 1216, 1062, 823, 762; HPLC: 96.8%.

Example 37

(2R,4R)-4-fluoro-2-(hydroxymethyl)-3,4-dimethyl-5-(6-morpholino-9H-purin-9-yl)tetrahydrofuran-3-ol

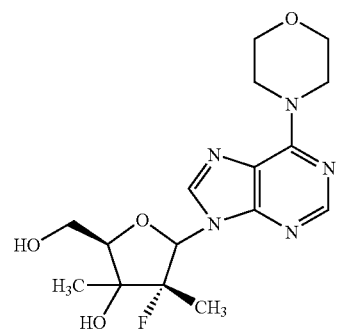

Isomer A: ¹H NMR (300 MHz, CDCl₃): δ 8.32 (s, 1H), 7.96 (d, 1H, J=3.6 Hz), 6.63 (d, 1H, J=22.8 Hz), 5.15 (s, 1H), 4.30-4.29 (m, 4H), 4.21-4.19 (m, 1H), 4.14-4.11 (m, 1H), 4.02-4.00 (m, 1H), 3.85-3.82 (m, 4H), 2.03 (s, 1H), 1.43-1.36 (m, 6H); Mass: [M+1]⁺ 368 (100%), [M+Na]⁺ 390 (80%); HPLC: 99.3%.

Isomer B: ¹H NMR (300 MHz, CDCl₃): δ 8.78 (s, 1H), 8.45 (d, 1H, J=4.5 Hz), 6.57 (d, 1H, J=22.8 Hz), 4.69 (s, 1H), 4.37-4.36 (m, 1H), 4.34-4.22 (m, 2H), 3.94-3.91 (m, 2H), 3.86-3.80 (m, 2H), 3.50-3.45 (m, 2H), 3.30-3.26 (m, 2H), 2.69 (s, 1H), 1.44 (d, 3H, J=2.1 Hz), 1.23 (d, 3H, J=22.5 Hz); ES Mass: [M+Na]⁺: 390 (80%), [M+1]⁺ 368 (100%); HPLC: 98.7%.

Example 38

((2R,4R)-3-acetoxy-4-fluoro-5-(5-fluoro-2,4-dioxo-3,4-dihydropyrimidin-1(2H)-yl)-3,4-dimethyltetrahydrofuran-2-yl)methyl benzoate

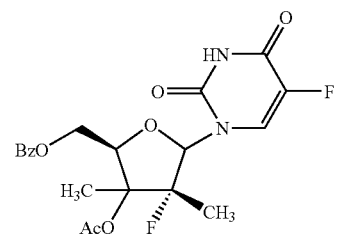

¹H-NMR: ¹H NMR (300 MHz, CDCl₃): δ 8.56 (bs, 1H), 8.06-8.04 (m, 2H), 7.63-7.58 (m, 1H), 7.50-7.45 (m, 2H), 7.42-7.39 (dd, 1H, J1=6.3 Hz, J2=6.0 Hz), 6.39-6.32 (dd, 1H, J1=22.5 Hz, J2=22.5 Hz), 4.79-4.47 (m, 1H), 4.68-4.63 (m, 1H), 4.47-4.41 (m, 1H), 2.13 (s, 3H), 1.82 (d, 3H, J=2.4 Hz), 1.50 (d, 3H, J=23.4 Hz); ES Mass: [M+Na]⁺: 461 (100%); IR cm⁻: 3550, 3479, 3414, 3227, 2283, 1723, 1275, 1113, 780; HPLC: 92.5%

Example 39

5-fluoro-1-((3R,5R)-3-fluoro-4-hydroxy-5-(hydroxymethyl)-3,4-dimethyltetrahydrofuran-2-yl)pyrimidine-2,4(1H,3H)-dione

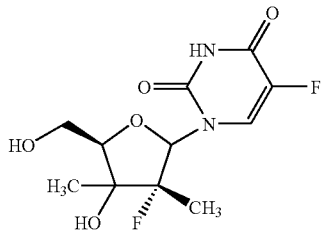

$^1$H-NMR: $^1$H NMR (300 MHz, CDCl$_3$): δ 11.44 (bs, 1H), 7.22-7.19 (dd, 1H, J1=6.6 Hz, J2=6.6 Hz), 6.14-6.06 (dd, 1H, J1=22.5 Hz, J2=22.5 Hz), 5.31 (s, 1H), 4.54-4.50 (m, 1H), 3.99-3.95 (m, 1H), 3.72-3.68 (m, 2H), 1.16 (d, 3H, J=23.1 Hz), 1.08 (d, 3H, J=2.4 Hz); ES Mass: [M+Na]$^+$: 315 (100%); HPLC: 99.4%

Example 40

((2R,4R)-4-fluoro-3-hydroxy-3,4-dimethyl-5-(6-morpholino-9H-purin-9-yl)tetrahydrofuran-2-yl)methyl pentanoate

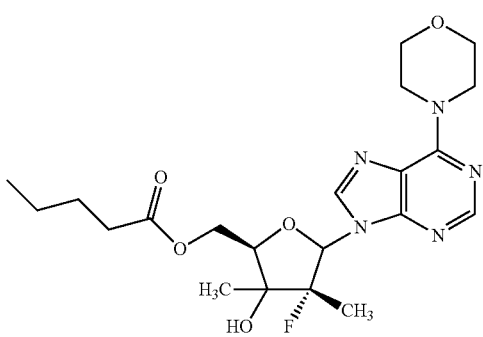

$^1$H NMR (300 MHz, CDCl$_3$): δ 8.33 (s, 1H), 7.98 (d, 1H, J=3.9 Hz), 6.58 (d, 1H, J=23.1 Hz), 4.63-4.57 (m, 2H), 4.32-4.24 (m, 5H), 3.86-3.83 (m, 4H), 3.03 (bs, 1H), 2.40-2.35 (t, 2H), 1.65-1.34 (m, 10H), 0.940.89 (t, 3H); ES Mass: [M+Na]$^+$: 474 (100%), [M+1]$^+$ 452 (20%); HPLC: 98.6%.

Example 41

((2R,4R)-4-fluoro-3-hydroxy-3,4-dimethyl-5-(6-morpholino-9H-purin-9-yl)tetrahydrofuran-2-yl)methyl butyrate

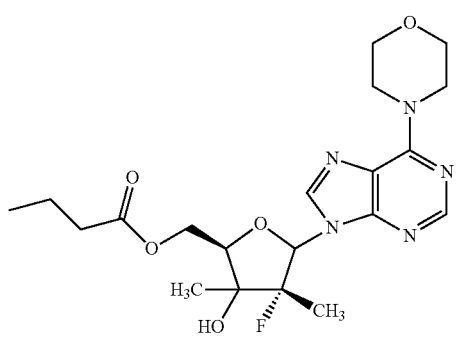

$^1$H NMR (300 MHz, CDCl$_3$): δ 8.32 (s, 1H), 7.99 (d, 1H, J=3.9 Hz), 6.60 (d, 1H, J=23.4 Hz), 4.63-4.57 (m, 2H), 4.32-4.27 (m, 5H), 3.86-3.83 (m, 4H), 2.38-2.33 (t, 2H), 1.71-1.66 (m, 2H), 1.43-1.34 (m, 6H), 1.00-0.94 (t, 3H); ES Mass: [M+Na]$^+$: 460 (100%), [M+1]$^+$ 438 (30%); IR cm$^-$: 3413, 3232, 2969, 1736, 1617, 1473, 1172, 1024, 940, 780. HPLC: 95.8%.

Example 42

((2R,4R)-4-fluoro-3-hydroxy-3,4-dimethyl-5-(6-morpholino-9H-purin-9-yl)tetrahydrofuran-2-yl)methyl isobutyrate

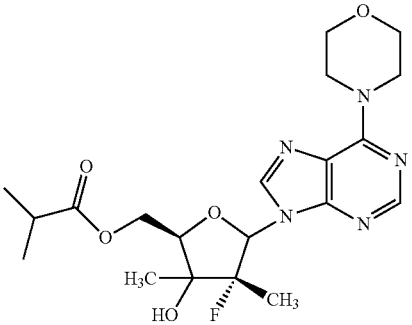

$^1$H NMR (300 MHz, CDCl$_3$): δ 8.32 (s, 1H), 7.99 (d, 1H, J=3.9 Hz), 6.61 (d, 1H, J=23.4 Hz), 4.60-4.52 (m, 2H), 4.32-4.25 (m, 5H), 3.86-3.83 (m, 4H), 3.43 (bs, 1H), 2.64-2.57 (m, 1H), 1.43-1.34 (m, 6H), 1.22-1.18 (m, 6H); ES Mass: [M+Na]$^+$: 460 (100%), [M+1]$^+$ 438 (30%); IR cm$^-$: 3414, 3227, 2964, 2849, 1735, 1637, 1387, 1280, 1023, 940; HPLC: 98%.

Example 43

(2R,4R)-5-(6-(3-chlorobenzylamino)-9H-purin-9-yl)-4-fluoro-2-(hydroxymethyl)-3,4-dimethyltetrahydrofuran-3-ol

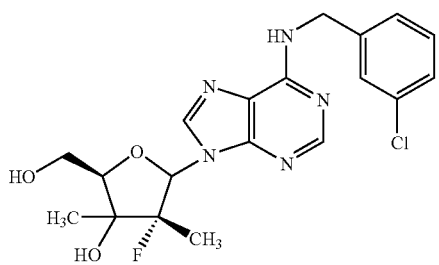

$^1$H NMR (300 MHz, CDCl$_3$): δ 8.40 (s, 1H), 7.96 (d, 1H, J=3.3 Hz), 7.39 (s, 1H), 7.30-7.11 (m, 3H), 6.63 (d, 1H, J=22.5 Hz), 6.34 (bs, 1H), 5.20 (s, 1H), 4.88 (bs, 1H), 4.42-4.12 (m, 3H), 1.46-1.38 (m, 6H); Mass: M+Na]$^+$ 444 (100%); HPLC: 99.6%.

Example 44

(2R,4R)-4-fluoro-5-(6-(furan-2-ylmethylamino)-9H-purin-9-yl)-2-(hydroxymethyl)-3,4-dimethyltetrahydrofuran-3-ol

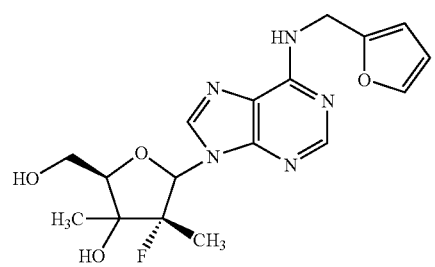

Isomer A: $^1$H NMR (300 MHz, CDCl$_3$): δ 8.37 (s, 1H), 7.95 (d, 1H, J=3.6 Hz), 7.36 (s, 1H), 6.61 (d, 1H, J=22.2 Hz), 6.31

(s, 2H), 5.55 (s, 1H), 4.85 (bs, 2H), 4.24-4.19 (m, 2H), 4.12-4.08 (m, 1H), 1.42-1.25 (m, 6H); Mass: [M+Na]$^+$ 400 (100%), 378 (30%); HPLC: 99.3%.

Isomer B: $^1$H NMR (300 MHz, CDCl$_3$): δ 8.48 (s, 1H), 8.01 (s, 1H), 7.40 (d, 1H, J=0.9 Hz), 6.51-6.50 (m, 1H), 6.39-6.32 (m, 2H), 6.22 (d, 1H, J=22.2 Hz), 5.81 (bs, 1H), 4.84-4.81 (m, 1H), 4.60-4.58 (m, 1H), 4.09-4.03 (m, 3H), 3.91-3.85 (m, 1H), 1.33-1.31 (m, 6H); Mass: [M+Na]$^+$ 400 (100%), 378 (70%); HPLC: 99%.

Example 45

(2R,4R)-5-(6-(2-chlorobenzylamino)-9H-purin-9-yl)-4-fluoro-2-(hydroxymethyl)-3,4-dimethyltetrahydrofuran-3-ol

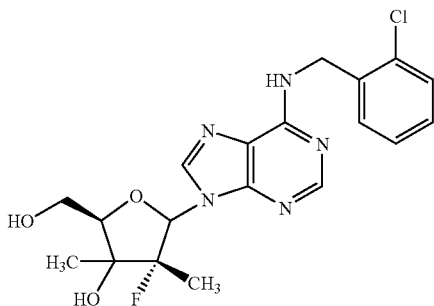

$^1$H NMR (300 MHz, CDCl$_3$): δ 8.38 (s, 1H), 7.98 (d, 1H, J=3.6 Hz), 7.50-7.47 (m, 1H), 7.40-7.18 (m, 3H), 6.61 (d, 1H, J=22.5 Hz), 6.25 (bs, 1H), 5.19 (s, 1H), 4.96 (bs, 1H), 4.22-4.02 (m, 3H), 1.43-1.25 (m, 6H); Mass: [M+Na]$^+$ 444 (100%), [M+1]$^+$ 422 (30%); HPLC: 98%.

Example 46

(2R,4R)-5-(6-(cyclobutylamino)-9H-purin-9-yl)-4-fluoro-2-(hydroxymethyl)-3,4-dimethyltetrahydrofuran-3-ol

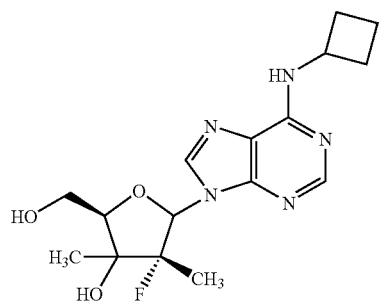

Isomer A: $^1$H NMR (300 MHz, CDCl$_3$): δ 8.33 (s, 1H), 7.96 (d, 1H, J=3.3 Hz), 6.60 (d, 1H, J=22.5 Hz), 6.04 (bs, 1H), 5.27 (s, 1H), 4.76 (bs, 1H), 4.22-4.08 (m, 3H), 2.49-2.46 (m, 1H), 2.36-2.18 (m, 3H), 2.04-1.94 (m, 3H), 1.42-1.35 (m, 6H); Mass: [M+Na]$^+$ 374 (100%); HPLC: 94%.

Isomer B: $^1$H NMR (300 MHz, CDCl$_3$): δ 8.28 (s, 1H), 8.00 (s, 1H), 6.08 (d, 1H, J=22.5 Hz), 4.57-4.52 (m, 1H), 4.28-4.27 (m, 1H), 3.92-3.91 (m, 2H), 3.26-3.18 (m, 1H), 2.37-2.35 (m, 2H), 1.85-1.79 (m, 2H), 1.73-1.66 (m, 2H), 1.31 (d, 3H, J=2.4 Hz), 1.18 (d, 3H, J=22.5 Hz); Mass: [M+1]$^+$ 352 (80%), [M+Na]$^+$ 374 (100%); HPLC: 93%.

Example 47

Preparation of (2S)-((2R,4R)-4-fluoro-3-hydroxy-3,4-dimethyl-5-(5-methyl-2,4-dioxo-3,4-dihydropyrimidin-1(2H)-yl)tetrahydrofuran-2-yl)methyl 2-(tert-butoxycarbonylamino)propanoate

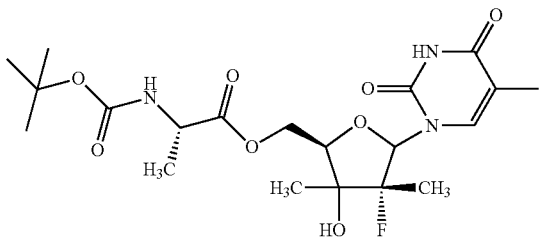

To a stirred solution of 1-((3R,5R)-3-fluoro-4-hydroxy-5-(hydroxymethyl)-3,4-dimethyltetrahydrofuran-2-yl)-5-methylpyrimidine-2,4(1H,3H)-dione (about 0.05 g, 0.17 mmol) in tetrahydrofuran (about 5 ml) was added N,N-dimethyl amino pyridine (about 0.06 g, 0.52 mmol), N,N'-methanediylidenedicyclohexanamine (about 0.071 g, 0.34 mmol) and (S)-2-(tert-butoxycarbonylamino)propanoic acid (about 0.09 g, 0.52 mmol) at about 0° C. and stirred at room temperature for about 1 hour. Completion of the reaction monitored by thin-layer chromatography and water added to the reaction mixture. The aqueous layer was extracted with ethyl acetate and the combined organic layers were washed with brine and dried over sodium sulphate. Concentration under reduced pressure and purification by silica gel column chromatography using 1.5% methanol in dichloromethane as eluent furnished title compound (0.03 g) as a colorless solid. Yield: 46.8%; $^1$H NMR (300 MHz, CDCl$_3$): δ 8.08 (bs, 1H), 7.23-7.22 (m, 1H), 6.37 (d, 1H, J=23.4 Hz), 4.95 (bs, 1H), 4.45-4.25 (m, 3H), 3.40-3.34 (m, 1H), 1.95 (s, 3H), 1.45 (d, 3H, J=22.8 Hz), 1.44 (s, 9H), 1.41 (m, 3H), 1.27 (s, 3H), ES Mass: [M+Na] 482 (100%).

Example 48

Preparation of ((2R,4R)-4-fluoro-3-hydroxy-3,4-dimethyl-5-(5-methyl-2,4-dioxo-3,4-dihydropyrimidin-1(2H)-yl)tetrahydrofuran-2-yl)methyl 2-aminopropanoate

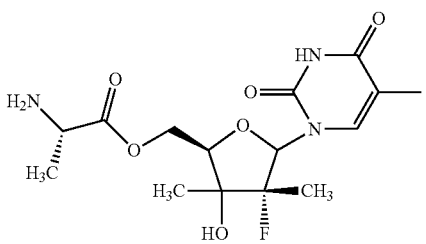

To a stirred solution of (2S)-((2R,4R)-4-fluoro-3-hydroxy-3,4-dimethyl-5-(5-methyl-2,4-dioxo-3,4-dihydropyrimidin-1(2H)-yl)tetrahydrofuran-2-yl)methyl 2-(tert-butoxycarbonylamino)propanoate (Example 47, about 0.005 g, 0.01 mmol) in dichloromethane was added trifluoroacetic acid (about 0.01 ml, 0.10 mmol) at about 0° C. and stirred at room temperature for about 1 hour. Completion of the reaction monitored by thin-layer chromatography and water added to the reaction mixture. The aqueous layer was added to saturated sodium bicarbonate and extracted with ethyl acetate, the combined organic layers were washed with brine and dried over sodium sulphate, Concentrated under reduced pressure to afford (0.02 g) crude compound. ES Mass: [M+1] 360 (100%).

Example 49

Determination of Absolute Stereochemistry

Crystal suitable for diffraction studies were grown from ethanol solvent. The crystals obtained are monoclinic,

| | | |
|---|---|---|
| Empirical formula | $C_{21}H_{20}ClFN_4O_5$ | |
| Formula weight | 462.86 | |
| Temperature | 294(2) K | |
| Wavelength | 0.71073 Å | |
| Crystal system | Monoclinic | |
| Space group | $P2_1$ | |
| Unit cell dimensions | a = 7.3691(8) Å | □ = 90°. |
| | b = 12.4257(13) Å | □ = 105.945(2)°. |
| | c = 12.1254(13) Å | □ = 90°. |
| Volume | 1067.6(2) Å$^3$ | |
| Z | 2 | |
| Density (calculated) | 1.440 Mg/m$^3$ | |
| Absorption coefficient | 0.229 mm$^{-1}$ | |
| F(000) | 480 | |
| Crystal size | 0.21 × 0.15 × 0.09 mm$^3$ | |
| θ range for data collection | 1.75 to 25.00°. | |
| Index ranges | −8 <= h <= 8, −14 <= k <= 14, −14 <= l <= 14 | |
| Reflections collected | 10277 | |
| Independent reflections | 3760 [R(int) = 0.0181] | |
| Completeness to θ = 25.00° | 99.9% | |
| Refinement method | Full-matrix least-squares on F$^2$ | |
| Data/restraints/parameters | 3760/1/292 | |
| Goodness-of-fit on F$^2$ | 1.059 | |
| Final R indices [I > 2σ(I)] | R1 = 0.0270, wR2 = 0.0703 | |
| R indices (all data) | R1 = 0.0275, wR2 = 0.0710 | |
| Absolute structure parameter | 0.03(5) | |
| Largest diff. peak and hole | 0.118 and −0.212 e · Å$^{-3}$ | |
| Measurement | Bruker Smart Apex CCD diffractometer | |
| Software Used | SHELXTL-PLUS | |

A computer generated perspective view of the molecule is shown in below Figure Lists of interatomic distances and angles are given in Table 1.

TABLE 1

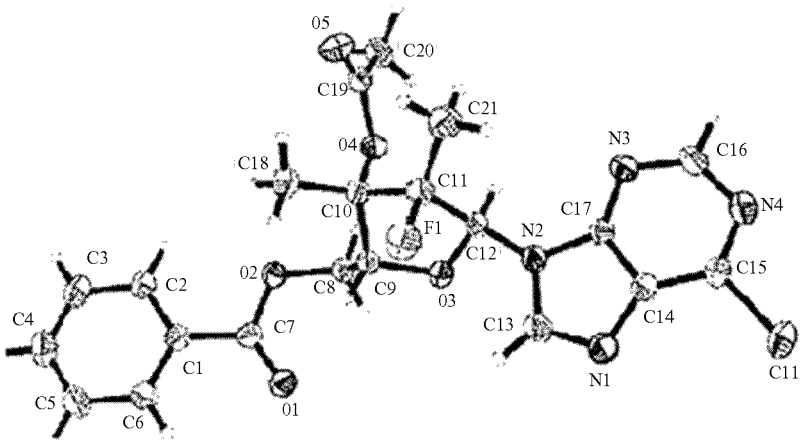

Bond lengths [Å] and angles [°] for Example 3:

| | | | |
|---|---|---|---|
| C(1)-C(6) | 1.383(2) | O(2)-C(7)-C(1) | 113.22(13) |
| C(1)-C(2) | 1.386(2) | O(2)-C(8)-C(9) | 110.05(12) |
| C(1)-C(7) | 1.478(2) | O(2)-C(8)-H(8A) | 109.7 |
| C(2)-C(3) | 1.377(3) | C(9)-C(8)-H(8A) | 109.7 |
| C(2)-H(2) | 0.9300 | O(2)-C(8)-H(8B) | 109.7 |
| C(3)-C(4) | 1.368(4) | C(9)-C(8)-H(8B) | 109.7 |
| C(3)-H(3) | 0.9300 | H(8A)-C(8)-H(8B) | 108.2 |
| C(4)-C(5) | 1.375(3) | O(3)-C(9)-C(8) | 107.07(12) |
| C(4)-H(4) | 0.9300 | O(3)-C(9)-C(10) | 106.16(11) |
| C(5)-C(6) | 1.380(3) | C(8)-C(9)-C(10) | 117.18(13) |
| C(5)-H(5) | 0.9300 | O(3)-C(9)-H(9) | 108.7 |
| C(6)-H(6) | 0.9300 | C(8)-C(9)-H(9) | 108.7 |
| C(7)-O(1) | 1.2015(19) | C(10)-C(9)-H(9) | 108.7 |
| C(7)-O(2) | 1.3464(19) | O(4)-C(10)-C(18) | 114.21(12) |
| C(8)-O(2) | 1.4400(19) | O(4)-C(10)-C(9) | 103.70(12) |
| C(8)-C(9) | 1.510(2) | C(18)-C(10)-C(9) | 113.06(13) |
| C(8)-H(8A) | 0.9700 | O(4)-C(10)-C(11) | 107.66(11) |
| C(8)-H(8B) | 0.9700 | C(18)-C(10)-C(11) | 116.64(14) |
| C(9)-O(3) | 1.4383(17) | C(9)-C(10)-C(11) | 99.91(11) |
| C(9)-C(10) | 1.534(2) | F(1)-C(11)-C(21) | 108.03(14) |
| C(9)-H(9) | 0.9800 | F(1)-C(11)-C(12) | 107.24(12) |
| C(10)-O(4) | 1.4517(17) | C(21)-C(11)-C(12) | 114.31(14) |
| C(10)-C(18) | 1.518(2) | F(1)-C(11)-C(10) | 105.12(12) |
| C(10)-C(11) | 1.536(2) | C(21)-C(11)-C(10) | 120.36(14) |
| C(11)-F(1) | 1.4062(18) | C(12)-C(11)-C(10) | 100.77(11) |

TABLE 1-continued

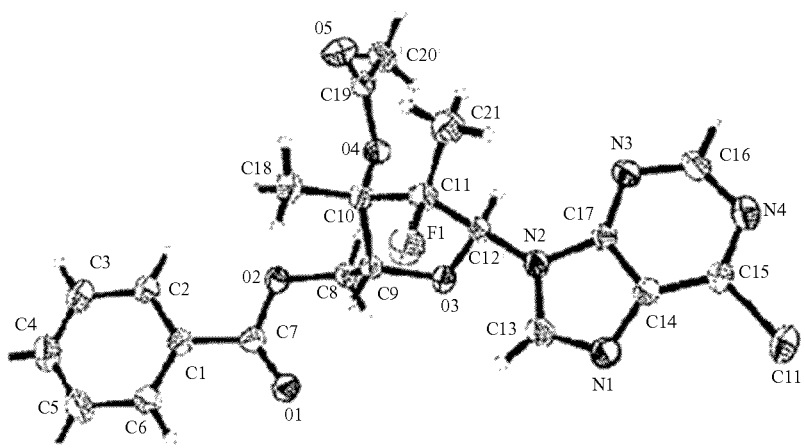

Bond lengths [Å] and angles [°] for Example 3:

| | | | |
|---|---|---|---|
| C(11)-C(21) | 1.492(3) | O(3)-C(12)-N(2) | 108.96(12) |
| C(11)-C(12) | 1.527(2) | O(3)-C(12)-C(11) | 106.29(11) |
| C(12)-O(3) | 1.4115(18) | N(2)-C(12)-C(11) | 114.62(12) |
| C(12)-N(2) | 1.4499(17) | O(3)-C(12)-H(12) | 108.9 |
| C(12)-H(12) | 0.9800 | N(2)-C(12)-H(12) | 108.9 |
| C(13)-N(1) | 1.302(2) | C(11)-C(12)-H(12) | 108.9 |
| C(13)-N(2) | 1.372(2) | N(1)-C(13)-N(2) | 114.29(15) |
| C(13)-H(13A) | 0.9300 | N(1)-C(13)-H(13A) | 122.9 |
| C(14)-C(15) | 1.375(2) | N(2)-C(13)-H(13A) | 122.9 |
| C(14)-N(1) | 1.381(2) | C(15)-C(14)-N(1) | 134.23(15) |
| C(14)-C(17) | 1.387(2) | C(15)-C(14)-C(17) | 114.55(15) |
| C(15)-N(4) | 1.309(2) | N(1)-C(14)-C(17) | 111.19(13) |
| C(15)-Cl(1) | 1.7275(17) | N(4)-C(15)-C(14) | 122.27(16) |
| C(16)-N(3) | 1.329(2) | N(4)-C(15)-Cl(1) | 118.28(13) |
| C(16)-N(4) | 1.340(2) | C(14)-C(15)-Cl(1) | 119.45(14) |
| C(16)-H(16) | 0.9300 | N(3)-C(16)-N(4) | 128.32(17) |
| C(17)-N(3) | 1.328(2) | N(3)-C(16)-H(16) | 115.8 |
| C(17)-N(2) | 1.3718(19) | N(4)-C(16)-H(16) | 115.8 |
| C(18)-H(18A) | 0.9600 | N(3)-C(17)-N(2) | 128.28(14) |
| C(18)-H(18B) | 0.9600 | N(3)-C(17)-C(14) | 126.51(14) |
| C(18)-H(18C) | 0.9600 | N(2)-C(17)-C(14) | 105.21(13) |
| C(19)-O(5) | 1.193(2) | C(10)-C(18)-H(18A) | 109.5 |
| C(19)-O(4) | 1.360(2) | C(10)-C(18)-H(18B) | 109.5 |
| C(19)-C(20) | 1.483(3) | H(18A)-C(18)-H(18B) | 109.5 |
| C(20)-H(20A) | 0.9600 | C(10)-C(18)-H(18C) | 109.5 |
| C(20)-H(20B) | 0.9600 | H(18A)-C(18)-H(18C) | 109.5 |
| C(20)-H(20C) | 0.9600 | H(18B)-C(18)-H(18C) | 109.5 |
| C(21)-H(21A) | 0.9600 | O(5)-C(19)-O(4) | 124.27(17) |
| C(21)-H(21B) | 0.9600 | O(5)-C(19)-C(20) | 125.89(17) |
| C(21)-H(21C) | 0.9600 | O(4)-C(19)-C(20) | 109.83(17) |
| C(6)-C(1)-C(2) | 119.74(16) | C(19)-C(20)-H(20A) | 109.5 |
| C(6)-C(1)-C(7) | 118.21(15) | C(19)-C(20)-H(20B) | 109.5 |
| C(2)-C(1)-C(7) | 121.92(16) | H(20A)-C(20)-H(20B) | 109.5 |
| C(3)-C(2)-C(1) | 119.45(19) | C(19)-C(20)-H(20C) | 109.5 |
| C(3)-C(2)-H(2) | 120.3 | H(20A)-C(20)-H(20C) | 109.5 |
| C(1)-C(2)-H(2) | 120.3 | H(20B)-C(20)-H(20C) | 109.5 |
| C(4)-C(3)-C(2) | 120.7(2) | C(11)-C(21)-H(21A) | 109.5 |
| C(4)-C(3)-H(3) | 119.7 | C(11)-C(21)-H(21B) | 109.5 |
| C(2)-C(3)-H(3) | 119.7 | H(21A)-C(21)-H(21B) | 109.5 |
| C(3)-C(4)-C(5) | 120.24(19) | C(11)-C(21)-H(21C) | 109.5 |
| C(3)-C(4)-H(4) | 119.9 | H(21A)-C(21)-H(21C) | 109.5 |
| C(5)-C(4)-H(4) | 119.9 | H(21B)-C(21)-H(21C) | 109.5 |
| C(4)-C(5)-C(6) | 119.8(2) | C(13)-N(1)-C(14) | 103.55(14) |
| C(4)-C(5)-H(5) | 120.1 | C(17)-N(2)-C(13) | 105.74(13) |
| C(6)-C(5)-H(5) | 120.1 | C(17)-N(2)-C(12) | 125.60(13) |
| C(5)-C(6)-C(1) | 120.10(17) | C(13)-N(2)-C(12) | 128.20(13) |
| C(5)-C(6)-H(6) | 119.9 | C(17)-N(3)-C(16) | 111.62(14) |
| C(1)-C(6)-H(6) | 119.9 | C(15)-N(4)-C(16) | 116.70(15) |
| O(1)-C(7)-O(2) | 122.50(14) | C(7)-O(2)-C(8) | 115.57(12) |
| O(1)-C(7)-C(1) | 124.28(15) | C(12)-O(3)-C(9) | 109.49(10) |
| | | C(19)-O(4)-C(10) | 123.47(13) |

Pharmacological Activity

The compounds described herein can be tested for their activity for antivirals following any procedures known to a person of ordinary skill in the art. For example, the following protocols may be employed for testing the compounds. These protocols are illustrative and do not limit to the scope of the invention.

Example 50

Screening the Activity of Antivirals Using Cell Viability Assay

Reduction of 3-(4,5-dimethylthiozol-2-yl)-2,5-diphenyltetrazolium bromide (MTT, sigma) is chosen as an optimal mend point of cell viability measurement (Mosmann, 1983; Cole, 1986; alley et al., 1988). Cells ($0.2 \times 10^6$ cells per well) were seeded in 96-well plates. Increasing concentrations of compound were added to the cells and incubated at 37° C. for about 14 hours in a $CO_2$ Incubator with 5% $CO_2$. The media was replaced with a fresh growth medium along with 20 µL of 5 mg/ml 3-(4,5-dimethylthiazol-2-yl)-2,5-diphenyltetrazolium bromide (MTT, Sigma). After incubation for about 4 hours in a humidified atmosphere, the media was removed and 200 µL of 0.1N acidic isopropyl alcohol was added to the wells to dissolve the MTT-formazan crystals. The absorbance was recorded at 570 nm, immediately after the development of purple colour. Each experiment was conducted in triplicate and the data are represented as average, with standard deviation. Percent viability of the cells was computed with reference to the absorbance of reduced MTT in the experiments conducted in absence of any compound.

P24 Assay:

Viral p24 was measured after about 72 hours of post infection in presence of drugs using ABL p24 ELISA kit. 0.5 millions cells/well were taken into the 24 well plates and added increasing concentrations of drugs. 1 ng/ml of HIV-1 virus was added to each well and incubated for overnight at 37° C. (37° C. and 5% $CO_2$). After about 16 hours incubation media was changed and added fresh media and cultured for about 72 hours. P24 was quantified at $4^{th}$ day of post-infection using ABL kit according to manufacturer's instructions.

The above described examples were tested in the two biological assays as described above and some compounds were found following results as shown in table 2.

Cell line Supt-1; Virus: HIV-1-93IN101

TABLE 2

| Example No. | Cytotoxicity concentration ($CC_{50}$) | Inhibitory concentration 50 ($IC_{50}$) | Therapeutic Index (TI): $CC_{50}/IC_{50}$ |
|---|---|---|---|
| 2A | >1 mM | >1 mM | >1 |
| 16 | 424.4 µM | 300 µM | 1.4 |
| 22 | >1 mM | >1 mM | >1 |
| 23 | >1 mM | >1 mM | >1 |
| Standard | >1 mM | 600 µM | — |

REFERENCES

1. Mosmann T, December 1983, *Journal of immunological methods,* 65 (1-2), 55-63.
2. SPC Cole, cancer chemotherapy and Pharmacology, 1986, 17, 259-263.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent applications cited in this application are herein incorporated by reference to the same extent as if each individual publication or patent application was specifically and individually indicated to be incorporated herein by reference.

We claim:

1. A compound of the formula (IA):

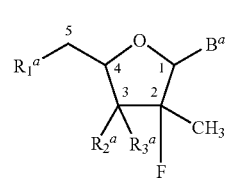

wherein, $B^a$ is Nitrogen heterocycle of from C3 to C15, selected from the group consisting of optionally substituted purine selected from adenine or guanine, pyrimidine selected from cytosine, uracil, or thymine, pteridine, triazolopyridine, imidazolopyridine, imidazolotriazine, pyrrolopyrimidine, or pyrazolopyrimidine; Nitrogen heterocycle may be bound to the sugar moiety in the nucleoside through any available ring Nitrogen atom;

$R_2^a$ and $R_3^a$ independently are selected from OH, methyl, $CH_3C(O)O$, $CH_3CH(CH_3)C(O)O$, $CH_3CH2CH2CH2C(O)O$, $PhC(O)O$, or $NH_2CH(R^a)C(O)O$, wherein $R^a$ is H, alkyl, or benezyl;

$R_1^a$ is OH, $CH_3C(O)O$, $PhC(O)O$, $CH_3CH_2CH_2C(O)O$, $CH_3CH(CH_3)C(O)O$, $CH_3CH_2CH_2CH_2C(O)O$ or $NH_2CH(R^a)C(O)O$, wherein $R^a$ is H, alkyl, or benezyl; a pharmaceutically acceptable salt thereof, a pharmaceutically acceptable solvate thereof, a pharmaceutically acceptable hydrate thereof, an N-oxide thereof, a tautomer thereof, a regioisomer thereof, a stereoisomer thereof, a prodrug thereof or a polymorph thereof.

2. A compound selected from the group consisting of:
   ((2R,4R)-3-(benzoyloxy)-5-(6-chloro-9H-purin-9-yl)-4-fluoro-3,4-dimethyltetrahydrofuran-2-yl)methyl benzoate,
   (2R,4R)-5-(6-amino-9H-purin-9-yl)-4-fluoro-2-(hydroxymethyl)-3,4-dimethyltetrahydrofuran-3-ol,
   (2R,4R)-4-fluoro-2-(hydroxymethyl)-5-(6-methoxy-9H-purin-9-yl)-3,4-dimethyltetrahydrofuran-3-ol,
   ((2R,4R)-3-acetoxy-5-(6-chloro-9H-purin-9-yl)-4-fluoro-3,4-dimethyltetrahydrofuran-2-yl)methyl benzoate,
   ((2R,4R)-3-acetoxy-5-(6-(cyclopropylamino)-9H-purin-9-yl)-4-fluoro-3,4-dimethyltetrahydrofuran-2-yl)methyl benzoate,
   ((2R,4R)-3-acetoxy-4-fluoro-5-(6-(4-fluorobenzylamino)-9H-purin-9-yl)-3,4-dimethyltetrahydrofuran-2-yl)methyl benzoate,
   ((2R,4R)-3-acetoxy-5-(6-(cyclobutylamino)-9H-purin-9-yl)-4-fluoro-3,4-dimethyltetrahydrofuran-2-yl)methyl benzoate, ((2R,4R)-3-acetoxy-4-fluoro-5-(6-(furan-2-ylmethylamino)-9H-purin-9-yl)-3,4-dimethyltetrahydrofuran-2-yl)methyl benzoate, ((2R,4R)-3-acetoxy-4-fluoro-5-(6-(isobutylamino)-9H-purin-9-yl)-3,4-dimethyltetrahydrofuran-2-yl)methyl benzoate, ((2R,4R)-3-acetoxy-4-fluoro-5-(6-(3-methoxybenzylamino)-9H-purin-9-yl)-3,4-dimethyltetrahydrofuran-2-yl)methyl benzoate, ((2R,4R)-3-acetoxy-5-(6-(3-chlorobenzylamino)-9H-purin-9-yl)-4-fluoro-3,4-dimethyltetrahydrofuran-2-yl)methyl benzoate, ((2R,4R)-3-acetoxy-4-fluoro-5-(6-(2-methoxybenzylamino)-9H-purin-9-yl)-3,4-dimethyltetrahydrofuran-2-yl)methyl benzoate, ((2R,4R)-3-acetoxy-5-(6-(2-chlorobenzylamino)-9H-purin-9-yl)-4-fluoro-3,4-dimethyltetrahydrofuran-2-yl)methyl benzoate, ((2R,4R)-3-acetoxy-4-fluoro-3,4-dimethyl-5-(6-morpholino-9H-purin-9-yl)tetrahydrofuran-2-yl)methyl benzoate, ((2R,4R)-3-acetoxy-5-(6-(cycloheptylamino)-9H-purin-9-yl)-4-fluoro-3,4-dimethyltetrahydrofuran-2-yl)methyl benzoate, (2R,4R)-5-(6-(cycloheptylamino)-9H-purin-9-yl)-4-fluoro-2-(hydroxymethyl)-3,4-dimethyltetrahydrofuran-3-ol, (2R,4R)-5-(6-(cyclopropylamino)-9H-purin-9-yl)-4-fluoro-2-(hydroxymethyl)-3,4-dimethyltetrahydrofuran-3-ol, ((2R,4R)-3-acetoxy-5-(6-(cyclopentylamino)-9H-purin-9-yl)-4-fluoro-3,4-dimethyltetrahydrofuran-2-yl)methyl benzoate, ((2R,4R)-3-acetoxy-5-(6-(cyclohexylamino)-9H-purin-9-yl)-4-fluoro-3,4-dimethyltetrahydrofuran-2-yl)methyl benzoate, ((2R,4R)-3-acetoxy-5-(2,4-dioxo-3,4-dihydropyrimidin-1(2H)-yl)-4-fluoro-3,4-dimethyltetrahydrofuran-2-yl)methyl benzoate, ((2R,4R)-3-acetoxy-4-fluoro-3,4-dimethyl-5-(5-methyl-2,4-dioxo-3,4-dihydropyrimidin-1(2H)-yl)tetrahydrofuran-2-yl)methyl acetate, ((2R,4R)-3-acetoxy-5-(4-benzamido-2-oxopyrimidin-1(2H)-yl)-4-fluoro-3,4-dimethyltetrahydrofuran-2-yl)methyl benzoate, 1-((2R,4R)-3-fluoro-4-hydroxy-5-(hydroxymethyl)-3,4-dimethyltetrahydrofuran-2-yl)pyrimidine-2,4(1H,3H)-dione, 4-amino-1-((2R,4R)-3-fluoro-4-hydroxy-5-(hydroxymethyl)-3,4-dimethyltetrahydrofuran-2-yl)pyrimidin-2(1H)-one, 1-((2R,4R)-3-fluoro-4-hydroxy-5-(hydroxymethyl)-3,4-dimethyltetrahydrofuran-2-yl)-5-methylpyrimidine-2,4(1H,3H)-dione, ((2R,4R)-3-acetoxy-5-(6-(cyclopropylmethylamino)-9H-purin-9-yl)-4-fluoro-3,4-dimethyltetrahydrofuran-2-yl)methyl benzoate, ((2R,4R)-3-acetoxy-5-(2-amino-6-chloro-9H-purin-9-yl)-4-fluoro-3,4-dimethyltetrahydrofuran-2-yl)methyl benzoate, (2R,4R)-5-(6-(cyclopentylamino)-9H-purin-9-yl)-4-fluoro-2-(hydroxymethyl)-3,4-dimethyltetrahydrofuran-3-ol, (2R,4R)-5-(6-(cyclohexylamino)-9H-purin-9-yl)-4-fluoro-2-(hydroxymethyl)-3,4-dimethyltetrahydrofuran-3-ol, ((2R,4R)-3-acetoxy-5-(6-(benzylamino)-9H-purin-9-yl)-4-fluoro-3,4-dimethyltetrahydrofuran-2-yl)methyl benzoate, (2R,4R)-5-(6-(cyclopropylmethylamino)-9H-purin-9-yl)-4-fluoro-2-(hydroxymethyl)-3,4-dimethyltetrahydrofuran-3-ol, ((2R,4R)-5-(2,4-dioxo-3,4-dihydropyrimidin-1(2H)-yl)-4-fluoro-3-hydroxy-3,4-dimethyltetrahydrofuran-2-yl)methyl butyrate, ((2R,4R)-5-(2,4-dioxo-3,4-dihydropyrimidin-1(2H)-yl)-4-fluoro-3-hydroxy-3,4-dimethyltetrahydrofuran-2-yl)methyl pentanoate, ((2R,4R)-3-acetoxy-4-fluoro-3,4-dimethyl-5-(6-oxo-1H-purin-9(6H)-yl)tetrahydrofuran-2-yl)methyl benzoate, 9-((3R,5R)-3-fluoro-4-hydroxy-5-(hydroxymethyl)-3,4-dimethyltetrahydrofuran-2-yl)-1H-purin-6(9H)-one, ((2R,4R)-3-acetoxy-4-fluoro-3,4-dimethyl-5-(5-methyl-2,4-dioxo-3,4-dihydropyrimidin-1(2H)-yl)tetrahydrofuran-2-yl)methyl benzoate, ((2R,4R)-5-(2,4-dioxo-3,4-dihydropyrimidin-1(2H)-yl)-4-fluoro-3-hydroxy-3,4-dimethyltetrahydrofuran-2-yl)methyl isobutyrat, (2R,4R)-4-fluoro-2-(hydroxymethyl)-3,4-dimethyl-5-(6-morpholino-9H-purin-9-yl)tetrahydrofuran-3-ol, ((2R,4R)-3-acetoxy-4-fluoro-5-(5-fluoro-2,4-dioxo-3,4-dihydropyrimidin-1(2H)-yl)-3,4-dimethyltetrahydrofuran-2-yl)methyl benzoate, 5-fluoro-1-((3R,5R)-3-fluoro-4-hydroxy-5-(hydroxymethyl)-3,4-dimethyltetrahydrofuran-2-yl)pyrimidine-2,4(1H,3H)-dione, ((2R,4R)-4-fluoro-3-hydroxy-3,4-dimethyl-5-(6-morpholino-9H-purin-9-yl)tetrahydrofuran-2-yl)methyl pentanoate, ((2R,4R)-4-fluoro-3-hydroxy-3,4-dimethyl-5-(6-morpholino-9H-purin-9-yl)tetrahydrofuran-2-yl)methyl butyrate, ((2R,4R)-4-fluoro-3-hydroxy-3,4-dimethyl-5-(6-morpholino-9H-purin-9-yl)tetrahydrofuran-2-yl)methyl isobutyrate, (2R,4R)-5-(6-(3-chlorobenzylamino)-9H-purin-9-yl)-4-fluoro-2-(hydroxymethyl)-3,4-dimethyltetrahydrofuran-3-ol, (2R,4R)-4-fluoro-5-(6-(furan-2-ylmethylamino)-9H-purin-9-yl)-2-(hydroxymethyl)-3,4-dimethyltetrahydrofuran-3-ol, (2R,4R)-5-(6-(2-chlorobenzylamino)-9H-purin-9-yl)-4-fluoro-2-(hydroxymethyl)-3,4-dimethyltetrahydrofuran-3-ol, (2R,4R)-5-(6-(cyclobutylamino)-9H-purin-9-yl)-4-fluoro-2-(hydroxymethyl)-3,4-dimethyltetrahydrofuran-3-ol, (2S)-((2R,4R)-4-fluoro-3-hydroxy-3,4-dimethyl-5-(5-methyl-2,4-dioxo-3,4-dihydropyrimidin-1(2H)-yl)tetrahydrofuran-2-yl)methyl 2-(tert-butoxycarbonylamino)propanoate, ((2R,4R)-4-fluoro-3-hydroxy-3,4-dimethyl-5-(5-methyl-2,4-dioxo-3,4-dihydropyrimidin-1(2H)-yl)tetrahydrofuran-2-yl)methyl 2-aminopropanoate, isomers thereof, and pharmaceutically acceptable salts thereof.

3. A compound of the formula (IIA)

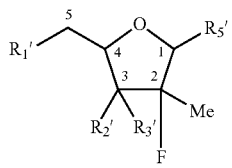

IIA wherein,
$R_1'$ is OH, O—CH2-Ph, O-t-butyldiphenylsilyl, O-Me;
$R_2'$ and $R_3'$ independently are selected from hydrogen, methyl, or hydroxyl; $R_2'$ and $R_3'$ can be together form oxo (=O) group;
$R_5'$ is hydroxyl, O—CH2-Ph, O-t-butyldiphenylsilyl, O-Me, O—C(O)CH$_3$, or O-trimethylsilyl; a pharmaceutically acceptable salt thereof, a pharmaceutically acceptable solvate thereof, a pharmaceutically acceptable hydrate thereof, an N-oxide thereof, a tautomer thereof, a regioisomer thereof, a stereoisomer thereof, a prodrug thereof or a polymorph thereof.

4. A process for the preparation of a compound of claim 3, wherein $R^4$ is alkyl group and X is halogen, which process comprises the steps of:
(a) reducing the compounds of formula (A) with a reducing agent

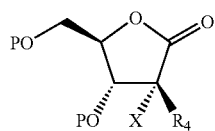

A to form a compound of formula (B)

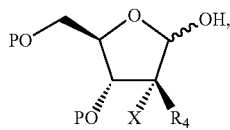

B (b) converting the compounds of formula (B) to the compounds of formula (C) and (D) by reacting with protecting agent

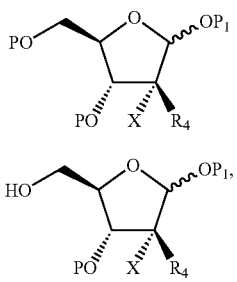

C

D (c) deprotecting the compounds of formula (C) and/or (D) under selective deprotecting conditions to form a compound of formula (E)

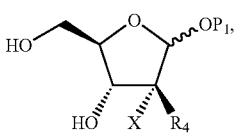

E (d) protecting the primary hydroxyl group of the compounds of formula (E) with a protecting agent to form a compound of formula (F),

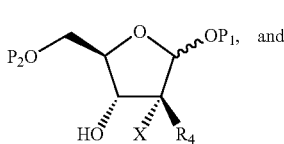

F (e) oxidising the compounds of formula (F) with an oxidising agent to form a compound of formula G

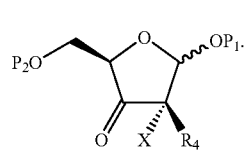

G

5. A process for the preparation of a compound of formula (I):

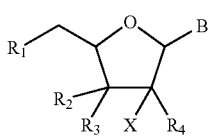

Formula (I)

wherein,
B is Nitrogen heterocycle of from C3 to C15, selected from the group consisting of optionally substituted purine, pyrimidine, pyridine, pyrrole, indole, imidazole, pyrazole, quinazoline, pyridizine, pyrezine, cinnoline, phthalazin, quinoxaline, xanthine, hypoxanthine, adenine, guanine, cytosine, uracil, thymine, pteridine, 5-azacytidine, 5-azauracil, triazolopyridine, imidazolopyridine, imidazolotriazine, pyrrolopyrimidine, pyrazolopyrimidine; the heterocycle may be bound to the sugar moiety in the nucleoside through any available atom including ring nitrogen or ring carbon atom;

X is halogen;

$R_4$ is alkyl group;

$R_2$ and $R_3$ are independently are selected from OH, alkyl, alkenyl, halogen, alkynyl, cycloalkyl, N$_3$, CF$_3$, NH$_2$, RCONHCH(Ra)C(O)O, NH$_2$CH(R$^a$)C(O)O (wherein R$^a$ can be H, alkyl or benezyl) or CN; $R_2$ and $R_3$ can be together form oxo (=O) group;

$R_1$ is H, OH, —{P(O)(OH)O-}nR, alkyl, hydrogen, acyl, aryl, alkyl carbonyloxy, aryl carbonyloxy, silyl, RCONHCH(Ra)C(O)O, NH$_2$CH(R$^a$)C(O)O wherein R$^a$ can be H, alkyl or benezyl, heterocycloalkyl, or sulfonyl;

R is alkyl, hydrogen, acyl, aryl, alkyl carbonyloxy, aryl carbonyloxy, or heterocycloalkyl;

$R_1$, $R_2$, $R_3$, $R_4$, and R are independently further substituted selected from the group consisting of halogen, alkyl, alkenyl, alkynyl, aryl, alkylaryl, aralkyl, cycloalkyl, heterocyclyl, heterocycloakyl, hydroxy, amino, cyano, azido, carbonyl, oxycarbonyl, sulfonyl, sulfonyloxy, or carbonyloxy, a pharmaceutically acceptable salt thereof, a pharmaceutically acceptable solvate thereof, a pharmaceutically acceptable hydrate thereof, an N-oxide thereof, a tautomer thereof, a regioisomer thereof, a stereoisomer thereof, a prodrug thereof or a polymorph thereof, the process comprising the steps of:

(a) reacting the compounds of formula (G)

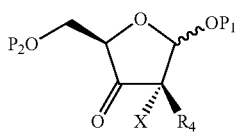
G with R$_2$—MgX to form a compound of formula (H)

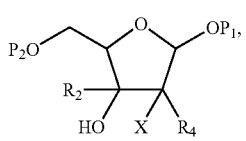
H (b) deprotecting the P$_2$ group of the compounds of formula (H) to form a compound of formula (J)

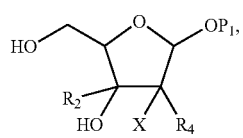
J (c) reacting the compounds of formula (J) with R$_1$/R$_3$—Cl to form a compound of formula (K)

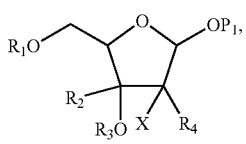
K (d) deprotecting the P$_1$ group of the compounds of formula (K) followed by reacting with a suitable reagent; L is a leaving group selected from the group consisting of O-acyl or O-silyl to form a compound of formula (L)

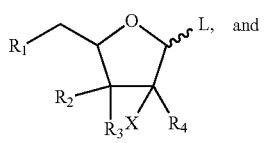
L, and (e) treating the compounds of formula (L) with suitable base (B) wherein, B is optionally substituted purine, pyrimidine, uracil, thiamine and cytosine, to form a compound of formula (I) in the presence of suitable coupling agent.

6. A process for the preparation of compounds of formula a and a':

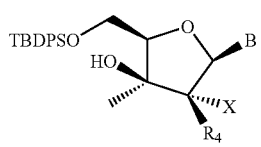
a

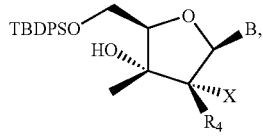
a' wherein,

B is Nitrogen heterocycle of from C3 to C15, selected from the group consisting of optionally substituted purine, pyrimidine, pyridine, pyrrole, indole, imidazole, pyrazole, quinazoline, pyridizine, pyrezine, cinnoline, phthalazin, quinoxaline, xanthine, hypoxanthine, adenine, guanine, cytosine, uracil, thymine, pteridine, 5-azacytidine, 5-azauracil, triazolopyridine, imidazolopyridine, imidazolotriazine, pyrrolopyrimidine, pyrazolopyrimidine; the heterocycle may be bound to the sugar moiety in the nucleoside through any available atom including ring nitrogen or ring carbon atom;

X is H, or halogen;

R$_4$ is H, or alkyl group;

the process comprising the steps of:

(a) reducing the compound of formula (G):

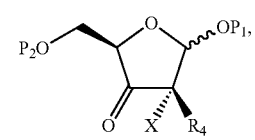
G to form diastereomers of compounds of formulae T and U:

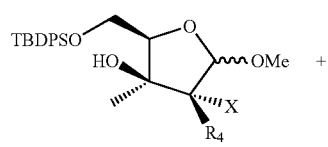
T

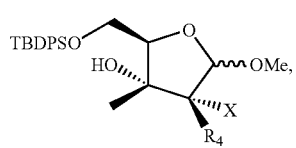
U (b) demethylating the compounds of formulae T and U to form respectively hydroxy compounds of formulae W and X in one or more base:

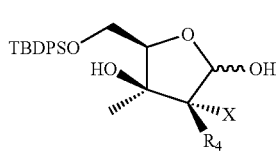
W

-continued

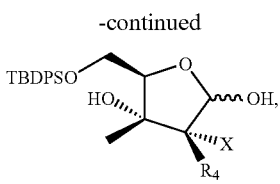
X (c) treating hydroxy compounds of formulae W and X for selective protection to form respectively selective protected compounds of formulae Y and Z in one or more protecting groups and one or more base and one or more solvent:

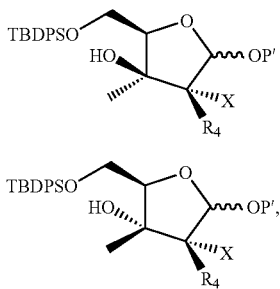

(d) reacting selective protected compounds of formulae Y and Z with suitable bases to form compounds of formulae a and a' in one or more coupling reagent and one or more solvent.

7. A compound of the formula (I):

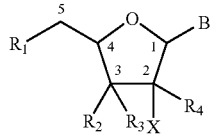
I wherein,
B is Nitrogen heterocycle of from C3 to C15, such as optionally substituted purine, pyrimidine, pyridine, pyrrole, indole, imidazole, pyrazole, quinazoline, pyridizine, pyrezine, cinnoline, phthalazin, quinoxaline, xanthine, hypoxanthine, adenine, guanine, cytosine, uracil, thymine, pteridine, 5-azacytidine, 5-azauracil, triazolopyridine, imidazolopyridine, imidazolotriazine, pyrrolopyrimidine, pyrazolopyrimidine; the heterocycle may be bound to the sugar moiety in the nucleoside through any available atom including ring nitrogen or ring carbon atom;
X is halogen;
$R_4$ is alkyl group;
$R_2$ and $R_3$ are independently are selected from OH, alkyl, alkenyl, halogen, alkynyl, cycloalkyl, $N_3$, $CF_3$, $NH_2$, RCONHCH(Ra)C(O)O, $NH_2CH(R^a)C(O)O$ (wherein $R^a$ is H, alkyl or benezyl) or CN; $R_2$ and $R_3$ can be together form oxo (=O) group;
R1 is H, OH, -{P(O)(OH)O-}nR, alkyl, hydrogen, acyl, aryl, alkyl carbonyloxy, aryl carbonyloxy, silyl, RCONHCH(Ra)C(O)O, $NH_2CH(R^a)C(O)O$ wherein $R^a$ is H, alkyl or benezyl, heterocycloalkyl, or sulfonyl;
R is alkyl, hydrogen, acyl, aryl, alkyl carbonyloxy, aryl carbonyloxy, or heterocycloalkyl;
$R_1$, $R_2$, $R_3$, $R_4$, and R are independently further substituted wherever appropriate by a group like halogen, alkyl, alkenyl, alkynyl, aryl, alkylaryl, aralkyl, cycloalkyl, heterocyclyl, heterocycloakyl, hydroxy, amino, cyano, azido, carbonyl, oxycarbonyl, sulfonyl, sulfonyloxy, or carbonyloxy, an analog thereof, a pharmaceutically acceptable salt thereof, a pharmaceutically acceptable solvate thereof, a pharmaceutically acceptable hydrate thereof, an N-oxide thereof, a tautomer thereof, a regioisomer thereof, a stereoisomer thereof, a prodrug thereof or a polymorph thereof.

8. A compound according to claim 7, wherein the compound is selected from the group consisting of:
((2R,3R,4R,5R)-3-(benzoyloxy)-5-(6-chloro-9H-purin-9-yl)-4-fluoro-3,4- dimethyltetrahydrofuran-2-yl) methyl benzoate,
((2R,3R,4R,5S)-3-(benzoyloxy)-5-(6-chloro-9H-purin-9-yl)-4-fluoro-3,4- dimethyltetrahydrofuran-2-yl) methyl benzoate,
((2R,3S,4R,5R)-3-(benzoyloxy)-5-(6-chloro-9H-purin-9-yl)-4-fluoro-3,4- dimethyltetrahydrofuran-2-yl) methyl benzoate,
((2R,3S,4R,5S)-3-(benzoyloxy)-5-(6-chloro-9H-purin-9-yl)-4-fluoro-3,4- dimethyltetrahydrofuran-2-yl) methyl benzoate,
(2R,3R,4R,5R)-5-(6-amino-9H-purin-9-yl)-4-fluoro-2-(hydroxymethyl)-3,4- dimethyltetrahydrofuran-3-ol,
(2R,3R,4R,5S)-5-(6-amino-9H-purin-9-yl)-4-fluoro-2-(hydroxymethyl)-3,4- dimethyltetrahydrofuran-3-ol,
(2R,3S,4R,5R)-5-(6-amino-9H-purin-9-yl)-4-fluoro-2-(hydroxymethyl)-3,4- dimethyltetrahydrofuran-3-ol,
(2R,3S,4R,5S)-5-(6-amino-9H-purin-9-yl)-4-fluoro-2-(hydroxymethyl)-3,4- dimethyltetrahydrofuran-3-ol,
(2R,3R,4R,5R)-4-fluoro-2-(hydroxymethyl)-5-(6-methoxy-9H-purin-9-yl)-3,4- dimethyltetrahydrofuran-3-ol,
(2R,3R,4R,5S)-4-fluoro-2-(hydroxymethyl)-5-(6-methoxy-9H-purin-9-yl)-3,4- dimethyltetrahydrofuran-3-ol,
(2R,3S,4R,5R)-4-fluoro-2-(hydroxymethyl)-5-(6-methoxy-9H-purin-9-yl)-3,4- dimethyltetrahydrofuran-3-ol,
(2R,3S,4R,5S)-4-fluoro-2-(hydroxymethyl)-5-(6-methoxy-9H-purin-9-yl)-3,4- dimethyltetrahydrofuran-3-ol,
((2R,3R,4R,5R)-3-acetoxy-5-(6-chloro-9H-purin-9-yl)-4-fluoro-3,4- dimethyltetrahydrofuran-2-yl)methyl benzoate,
((2R,3R,4R,5S)-3-acetoxy-5-(6-chloro-9H-purin-9-yl)-4-fluoro-3,4- dimethyltetrahydrofuran-2-yl)methyl benzoate,
((2R,3S,4R,5R)-3-acetoxy-5-(6-chloro-9H-purin-9-yl)-4-fluoro-3,4- dimethyltetrahydrofuran-2-yl)methyl benzoate,
((2R,3S,4R,5S)-3-acetoxy-5-(6-chloro-9H-purin-9-yl)-4-fluoro-3,4- dimethyltetrahydrofuran-2-yl)methyl benzoate,
((2R,3R,4R,5R)-3-acetoxy-5-(6-(cyclopropylamino)-9H-purin-9-yl)-4-fluoro-3,4- dimethyltetrahydrofuran-2-yl)methyl benzoate,
((2R,3R,4R,5S)-3-acetoxy-5-(6-(cyclopropylamino)-9H-purin-9-yl)-4-fluoro-3,4- dimethyltetrahydrofuran-2-yl)methyl benzoate,
((2R,3S,4R,5R)-3-acetoxy-5-(6-(cyclopropylamino)-9H-purin-9-yl)-4-fluoro-3,4- dimethyltetrahydrofuran-2-yl)methyl benzoate, ((2R,3S,4R,5S)-3-acetoxy-5-(6-(cyclopropylamino)-9H-purin-9-yl)-4-fluoro-3,4-dimethyltetrahydrofuran-2-yl)methyl benzoate,
((2R,3R,4R,5R)-3-acetoxy-4-fluoro-5-(6-(4-fluorobenzylamino)-9H-purin-9-yl)-3,4-dimethyltetrahydrofuran-2-yl)methyl benzoate,
((2R,3R,4R,5S)-3-acetoxy-4-fluoro-5-(6-(4-fluorobenzylamino)-9H-purin-9-yl)-3,4-dimethyltetrahydrofuran-2-yl)methyl benzoate,
((2R,3S,4R,5R)-3-acetoxy-4-fluoro-5-(6-(4-fluorobenzylamino)-9H-purin-9-yl)-3,4-dimethyltetrahydrofuran-2-yl)methyl benzoate,
((2R,3S,4R,5S)-3-acetoxy-4-fluoro-5-(6-(4-fluorobenzylamino)-9H-purin-9-yl)-3,4-dimethyltetrahydrofuran-2-yl)methyl benzoate,
((2R,3R,4R,5R)-3-acetoxy-5-(6-(cyclobutylamino)-9H-purin-9-yl)-4-fluoro-3,4-dimethyltetrahydrofuran-2-yl)methyl benzoate,
((2R,3R,4R,5S)-3-acetoxy-5-(6-(cyclobutylamino)-9H-purin-9-yl)-4-fluoro-3,4-dimethyltetrahydrofuran-2-yl)methyl benzoate,
((2R,3S,4R,5R)-3-acetoxy-5-(6-(cyclobutylamino)-9H-purin-9-yl)-4-fluoro-3,4-dimethyltetrahydrofuran-2-yl)methyl benzoate,
((2R,3S,4R,5S)-3-acetoxy-5-(6-(cyclobutylamino)-9H-purin-9-yl)-4-fluoro-3,4-dimethyltetrahydrofuran-2-yl)methyl benzoate,
((2R,3R,4R,5R)-3-acetoxy-4-fluoro-5-(6-(furan-2-ylmethylamino)-9H-purin-9-yl)-3,4-dimethyltetrahydrofuran-2-yl)methyl benzoate,
((2R,3R,4R,5S)-3-acetoxy-4-fluoro-5-(6-(furan-2-ylmethylamino)-9H-purin-9-yl)-3,4-dimethyltetrahydrofuran-2-yl)methyl benzoate,
((2R,3S,4R,5R)-3-acetoxy-4-fluoro-5-(6-(furan-2-ylmethylamino)-9H-purin-9-yl)-3,4-dimethyltetrahydrofuran-2-yl)methyl benzoate,
((2R,3S,4R,5S)-3-acetoxy-4-fluoro-5-(6-(furan-2-ylmethylamino)-9H-purin-9-yl)-3,4-dimethyltetrahydrofuran-2-yl)methyl benzoate,
((2R,3R,4R,5R)-3-acetoxy-4-fluoro-5-(6-(isobutylamino)-9H-purin-9-yl)-3,4-dimethyltetrahydrofuran-2-yl)methyl benzoate,
((2R,3R,4R,5S)-3-acetoxy-4-fluoro-5-(6-(isobutylamino)-9H-purin-9-yl)-3,4-dimethyltetrahydrofuran-2-yl)methyl benzoate,
((2R,3S,4R,5R)-3-acetoxy-4-fluoro-5-(6-(isobutylamino)-9H-purin-9-yl)-3,4-dimethyltetrahydrofuran-2-yl)methyl benzoate,
((2R,3S,4R,5S)-3-acetoxy-4-fluoro-5-(6-(isobutylamino)-9H-purin-9-yl)-3,4-dimethyltetrahydrofuran-2-yl)methyl benzoate,
((2R,3R,4R,5R)-3-acetoxy-4-fluoro-5-(6-(3-methoxybenzylamino)-9H-purin-9-yl)-3,4-dimethyltetrahydrofuran-2-yl)methyl benzoate,
((2R,3R,4R,5S)-3-acetoxy-4-fluoro-5-(6-(3-methoxybenzylamino)-9H-purin-9-yl)-3,4-dimethyltetrahydrofuran-2-yl)methyl benzoate,
((2R,3S,4R,5R)-3-acetoxy-4-fluoro-5-(6-(3-methoxybenzylamino)-9H-purin-9-yl)-3,4-dimethyltetrahydrofuran-2-yl)methyl benzoate,
((2R,3S,4R,5S)-3-acetoxy-4-fluoro-5-(6-(3-methoxybenzylamino)-9H-purin-9-yl)-3,4-dimethyltetrahydrofuran-2-yl)methyl benzoate,
((2R,3R,4R,5R)-3-acetoxy-5-(6-(3-chlorobenzylamino)-9H-purin-9-yl)-4-fluoro-3,4-dimethyltetrahydrofuran-2-yl)methyl benzoate,
((2R,3R,4R,5S)-3-acetoxy-5-(6-(3-chlorobenzylamino)-9H-purin-9-yl)-4-fluoro-3,4-dimethyltetrahydrofuran-2-yl)methyl benzoate,
((2R,3S,4R,5R)-3-acetoxy-5-(6-(3-chlorobenzylamino)-9H-purin-9-yl)-4-fluoro-3,4-dimethyltetrahydrofuran-2-yl)methyl benzoate,
((2R,3S,4R,5S)-3-acetoxy-5-(6-(3-chlorobenzylamino)-9H-purin-9-yl)-4-fluoro-3,4-dimethyltetrahydrofuran-2-yl)methyl benzoate,
((2R,3R,4R,5R)-3-acetoxy-4-fluoro-5-(6-(2-methoxybenzylamino)-9H-purin-9-yl)-3,4-dimethyltetrahydrofuran-2-yl)methyl benzoate,
((2R,3R,4R,5S)-3-acetoxy-4-fluoro-5-(6-(2-methoxybenzylamino)-9H-purin-9-yl)-3,4-dimethyltetrahydrofuran-2-yl)methyl benzoate,
((2R,3S,4R,5R)-3-acetoxy-4-fluoro-5-(6-(2-methoxybenzylamino)-9H-purin-9-yl)-3,4-dimethyltetrahydrofuran-2-yl)methyl benzoate,
((2R,3S,4R,5S)-3-acetoxy-4-fluoro-5-(6-(2-methoxybenzylamino)-9H-purin-9-yl)-3,4-dimethyltetrahydrofuran-2-yl)methyl benzoate,
((2R,3R,4R,5R)-3-acetoxy-5-(6-(2-chlorobenzylamino)-9H-purin-9-yl)-4-fluoro-3,4-dimethyltetrahydrofuran-2-yl)methyl benzoate,
((2R,3R,4R,5S)-3-acetoxy-5-(6-(2-chlorobenzylamino)-9H-purin-9-yl)-4-fluoro-3,4-dimethyltetrahydrofuran-2-yl)methyl benzoate,
((2R,3S,4R,5R)-3-acetoxy-5-(6-(2-chlorobenzylamino)-9H-purin-9-yl)-4-fluoro-3,4-dimethyltetrahydrofuran-2-yl)methyl benzoate,
((2R,3S,4R,5S)-3-acetoxy-5-(6-(2-chlorobenzylamino)-9H-purin-9-yl)-4-fluoro-3,4-dimethyltetrahydrofuran-2-yl)methyl benzoate,
((2R,3R,4R,5R)-3-acetoxy-4-fluoro-3,4-dimethyl-5-(6-morpholino-9H-purin-9-yl)tetrahydrofuran-2-yl)methyl benzoate,
((2R,3R,4R,5S)-3-acetoxy-4-fluoro-3,4-dimethyl-5-(6-morpholino-9H-purin-9-yl)tetrahydrofuran-2-yl)methyl benzoate,
((2R,3S,4R,5R)-3-acetoxy-4-fluoro-3,4-dimethyl-5-(6-morpholino-9H-purin-9-yl)tetrahydrofuran-2-yl)methyl benzoate,
((2R,3S,4R,5S)-3-acetoxy-4-fluoro-3,4-dimethyl-5-(6-morpholino-9H-purin-9-yl)tetrahydrofuran-2-yl)methyl benzoate,
((2R,3R,4R,5R)-3-acetoxy-5-(6-(cycloheptylamino)-9H-purin-9-yl)-4-fluoro-3,4-dimethyltetrahydrofuran-2-yl)methyl benzoate,
((2R,3R,4R,5S)-3-acetoxy-5-(6-(cycloheptylamino)-9H-purin-9-yl)-4-fluoro-3,4-dimethyltetrahydrofuran-2-yl)methyl benzoate,
((2R,3S,4R,5R)-3-acetoxy-5-(6-(cycloheptylamino)-9H-purin-9-yl)-4-fluoro-3,4-dimethyltetrahydrofuran-2-yl)methyl benzoate,
((2R,3S,4R,5S)-3-acetoxy-5-(6-(cycloheptylamino)-9H-purin-9-yl)-4-fluoro-3,4-dimethyltetrahydrofuran-2-yl)methyl benzoate,
(2R,3R,4R,5R)-5-(6-(cycloheptylamino)-9H-purin-9-yl)-4-fluoro-2-(hydroxymethyl)-3,4-dimethyltetrahydrofuran-3-ol,
(2R,3R,4R,5S)-5-(6-(cycloheptylamino)-9H-purin-9-yl)-4-fluoro-2-(hydroxymethyl)-3,4-dimethyltetrahydrofuran-3-ol,
(2R,3S,4R,5R)-5-(6-(cycloheptylamino)-9H-purin-9-yl)-4-fluoro-2-(hydroxymethyl)-3,4-dimethyltetrahydrofuran-3-ol, (2R,3S,4R,5S)-5-(6-(cycloheptylamino)-9H-purin-9-yl)-4-fluoro-2-(hydroxymethyl)-3,4-dimethyltetrahydrofuran-3-ol, (2R,3R,4R,5R)-5-(6-(cyclopropylamino)-9H-purin-9-yl)-4-fluoro-2-(hydroxymethyl)-3,4-dimethyltetrahydrofuran-3-ol, (2R,3R,4R,5S)-5-(6-(cyclopropylamino)-9H-purin-9-yl)-4-fluoro-2-(hydroxymethyl)-3,4-dimethyltetrahydrofuran-3-ol, (2R,3S,4R,5R)-5-(6-(cyclopropylamino)-9H-purin-9-yl)-4-fluoro-2-(hydroxymethyl)-3,4-dimethyltetrahydrofuran-3-ol, (2R,3S,4R,5S)-5-(6-(cyclopropylamino)-9H-purin-9-yl)-4-fluoro-2-(hydroxymethyl)-3,4-dimethyltetrahydrofuran-3-ol, ((2R,3R,4R,5R)-3-acetoxy-5-(6-(cyclopentylamino)-9H-purin-9-yl)-4-fluoro-3,4-dimethyltetrahydrofuran-2-yl)methyl benzoate, ((2R,3R,4R,5S)-3-acetoxy-5-(6-(cyclopentylamino)-9H-purin-9-yl)-4-fluoro-3,4-dimethyltetrahydrofuran-2-yl)methyl benzoate, ((2R,3S,4R,5R)-3-acetoxy-5-(6-(cyclopentylamino)-9H-purin-9-yl)-4-fluoro-3,4-dimethyltetrahydrofuran-2-yl)methyl benzoate, ((2R,3S,4R,5S)-3-acetoxy-5-(6-(cyclopentylamino)-9H-purin-9-yl)-4-fluoro-3,4-dimethyltetrahydrofuran-2-yl)methyl benzoate, ((2R,3R,4R,5R)-3-acetoxy-5-(6-(cyclohexylamino)-9H-purin-9-yl)-4-fluoro-3,4-dimethyltetrahydrofuran-2-yl)methyl benzoate, ((2R,3R,4R,5S)-3-acetoxy-5-(6-(cyclohexylamino)-9H-purin-9-yl)-4-fluoro-3,4- dimethyltetrahydrofuran-2-yl)methyl benzoate, ((2R,3S,4R,5R)-3-acetoxy-5-(6-(cyclohexylamino)-9H-purin-9-yl)-4-fluoro-3,4- dimethyltetrahydrofuran-2-yl)methyl benzoate, ((2R,3S,4R,5S)-3-acetoxy-5-(6-(cyclohexylamino)-9H-purin-9-yl)-4-fluoro-3,4- dimethyltetrahydrofuran-2-yl)methyl benzoate, ((2R,3R,4R,5R)-3-acetoxy-5-(2,4-dioxo-3,4-dihydropyrimidin-1 (2H)-yl)-4-fluoro-3,4-dimethyltetrahydrofuran-2-yl)methyl benzoate, ((2R,3R,4R,5S)-3-acetoxy-5-(2,4-dioxo-3,4-dihydropyrimidin-1 (2H)-yl)-4-fluoro-3,4-dimethyltetrahydrofuran-2-yl)methyl benzoate, (2R,3S,4R,5S)-5-(6-(cycloheptylamino)-9H-purin-9-yl)-4-fluoro-2-(hydroxymethyl)-3,4-dimethyltetrahydrofuran-3-ol, (2R,3R,4R,5R)-5-(6-(cyclopropylamino)-9H-purin-9-yl)-4-fluoro-2-(hydroxymethyl)-3,4-dimethyltetrahydrofuran-3-ol, (2R,3R,4R,5S)-5-(6-(cyclopropylamino)-9H-purin-9-yl)-4-fluoro-2-(hydroxymethyl)-3,4-dimethyltetrahydrofuran-3-ol, (2R,3S,4R,5R)-5-(6-(cyclopropylamino)-9H-purin-9-yl)-4-fluoro-2-(hydroxymethyl)-3,4-dimethyltetrahydrofuran-3-ol, (2R,3S,4R,5S)-5-(6-(cyclopropylamino)-9H-purin-9-yl)-4-fluoro-2-(hydroxymethyl)-3,4-dimethyltetrahydrofuran-3-ol, ((2R,3R,4R,5R)-3-acetoxy-5-(6-(cyclopentylamino)-9H-purin-9-yl)-4-fluoro-3,4-dimethyltetrahydrofuran-2-yl)methyl benzoate, ((2R,3R,4R,5S)-3-acetoxy-5-(6-(cyclopentylamino)-9H-purin-9-yl)-4-fluoro-3,4-dimethyltetrahydrofuran-2-yl)methyl benzoate, ((2R,3S,4R,5R)-3-acetoxy-5-(6-(cyclopentylamino)-9H-purin-9-yl)-4-fluoro-3,4-dimethyltetrahydrofuran-2-yl)methyl benzoate, ((2R,3S,4R,5S)-3-acetoxy-5-(6-(cyclopentylamino)-9H-purin-9-yl)-4-fluoro-3,4-dimethyltetrahydrofuran-2-yl)methyl benzoate, ((2R,3R,4R,5R)-3-acetoxy-5-(6-(cyclohexylamino)-9H-purin-9-yl)-4-fluoro-3,4-dimethyltetrahydrofuran-2-yl)methyl benzoate, ((2R,3R,4R,5S)-3-acetoxy-5-(6-(cyclohexylamino)-9H-purin-9-yl)-4-fluoro-3,4-dimethyltetrahydrofuran-2-yl)methyl benzoate, ((2R,3S,4R,5R)-3-acetoxy-5-(6-(cyclohexylamino)-9H-purin-9-yl)-4-fluoro-3,4-dimethyltetrahydrofuran-2-yl)methyl benzoate, ((2R,3S,4R,5S)-3-acetoxy-5-(6-(cyclohexylamino)-9H-purin-9-yl)-4-fluoro-3,4-dimethyltetrahydrofuran-2-yl)methyl benzoate, ((2R,3R,4R,5R)-3-acetoxy-5-(2,4-dioxo-3,4-dihydropyrimidin-1(2H)-yl)-4-fluoro-3,4-dimethyltetrahydrofuran-2-yl)methyl benzoate, ((2R,3R,4R,5S)-3-acetoxy-5-(2,4-dioxo-3,4-dihydropyrimidin-1(2H)-yl)-4-fluoro-3,4-dimethyltetrahydrofuran-2-yl)methyl benzoate, ((2R,3S,4R,5R)-3-acetoxy-5-(2,4-dioxo-3,4-dihydropyrimidin-1 (2H)-yl)-4-fluoro-3,4-dimethyltetrahydrofuran-2-yl)methyl benzoate, ((2R,3S,4R,5S)-3-acetoxy-5-(2,4-dioxo-3,4-dihydropyrimidin-1 (2H)-yl)-4-fluoro-3,4-dimethyltetrahydrofuran-2-yl)methyl benzoate, ((2R,3R,4R,5R)-3-acetoxy-4-fluoro-3,4-dimethyl-5-(5-methyl-2,4-dioxo-3,4- dihydropyrimidin- 1 (2H)-yl)tetrahydrofuran-2-yl)methyl acetate, ((2R,3R,4R,5S)-3-acetoxy-4-fluoro-3,4-dimethyl-5-(5-methyl-2,4-dioxo-3,4-dihydropyrimidin-1(2H)-yl)tetrahydrofuran-2-yl)methyl acetate, ((2R,3S,4R,5R)-3-acetoxy-4-fluoro-3,4-dimethyl-5-(5-methyl-2,4-dioxo-3,4-dihydropyrimidin-1(2H)-yl)tetrahydrofuran-2-yl)methyl acetate, ((2R,3S,4R,5S)-3-acetoxy-4-fluoro-3,4-dimethyl-5-(5-methyl-2,4-dioxo-3,4-dihydropyrimidin-1(2H)-yl)tetrahydrofuran-2-yl)methyl acetate, ((2R,3R,4R,5R)-3-acetoxy-5-(4-benzamido-2-oxopyrimidin-1(2H)-yl)-4-fluoro-3,4-dimethyltetrahydrofuran-2-yl)methyl benzoate, ((2R,3R,4R,5S)-3-acetoxy-5-(4-benzamido-2-oxopyrimidin-1(2H)-yl)-4-fluoro-3,4-dimethyltetrahydrofuran-2-yl)methyl benzoate, ((2R,3S,4R,5R)-3-acetoxy-5-(4-benzamido-2-oxopyrimidin-1(2H)-yl)-4-fluoro-3,4-dimethyltetrahydrofuran-2-yl)methyl benzoate, ((2R,3S,4R,5S)-3-acetoxy-5-(4-benzamido-2-oxopyrimidin-1(2H)-yl)-4-fluoro-3,4-dimethyltetrahydrofuran-2-yl)methyl benzoate, 1-((2R,3R,4R,5R)-3-fluoro-4-hydroxy-5-(hydroxymethyl)-3,4-dimethyltetrahydrofuran-2-yl)pyrimidine-2,4(1 H,3H)-dione, 1-((2R,3R,4R,5S)-3-fluoro-4-hydroxy-5-(hydroxymethyl)-3,4-dimethyltetrahydrofuran-2-yl)pyrimidine-2,4(1 H,3H)-dione, 1-((2R,3S,4R,5R)-3-fluoro-4-hydroxy-5-(hydroxymethyl)-3,4-dimethyltetrahydrofuran-2-yl)pyrimidine-2,4(1 H,3H)-dione, 1-((2R,3S,4R,5S)-3-fluoro-4-hydroxy-5-(hydroxymethyl)-3,4-dimethyltetrahydrofuran-2-yl)pyrimidine-2,4(1 H,3H)-dione, 4-amino-1-((2R,3R,4R,5R)-3-fluoro-4-hydroxy-5-(hydroxymethyl)-3,4-dimethyltetrahydrofuran-2-yl)pyrimidin-2(1H)-one,
4-amino-1-((2R,3R,4R,5S)-3-fluoro-4-hydroxy-5-(hydroxymethyl)-3,4-dimethyltetrahydrofuran-2-yl)pyrimidin-2(1H)-one,
4-amino-1-((2R,3S,4R,5R)-3-fluoro-4-hydroxy-5-(hydroxymethyl)-3,4-dimethyltetrahydrofuran-2-yl)pyrimidin-2(1H)-one,
4-amino-1-((2R,3S,4R,5S)-3-fluoro-4-hydroxy-5-(hydroxymethyl)-3,4-dimethyltetrahydrofuran-2-yl)pyrimidin-2(1H)-one,
1-((2R,3R,4R,5R)-3-fluoro-4-hydroxy-5-(hydroxymethyl)-3,4-dimethyltetrahydrofuran-2-yl)-5-methylpyrimidine-2,4(1H,3H)-dione,
1-((2R,3R,4R,5S)-3-fluoro-4-hydroxy-5-(hydroxymethyl)-3,4-dimethyltetrahydrofuran-2-yl)-5-methylpyrimidine-2,4(1H,3H)-dione,
1-((2R,3S,4R,5R)-3-fluoro-4-hydroxy-5-(hydroxymethyl)-3,4-dimethyltetrahydrofuran-2-yl)-5-methylpyrimidine-2,4(1H,3H)-dione,
1-((2R,3S,4R,5S)-3-fluoro-4-hydroxy-5-(hydroxymethyl)-3,4-dimethyltetrahydrofuran-2-yl)-5-methylpyrimidine-2,4(1H,3H)-dione,
((2R,3R,4R,5R)-3-acetoxy-5-(6-(cyclopropylmethylamino)-9H-purin-9-yl)-4-fluoro-3,4-dimethyltetrahydrofuran-2-yl)methyl benzoate,
((2R,3R,4R,5S)-3-acetoxy-5-(6-(cyclopropylmethylamino)-9H-purin-9-yl)-4-fluoro-3,4-dimethyltetrahydrofuran-2-yl)methyl benzoate,
((2R,3S,4R,5R)-3-acetoxy-5-(6-(cyclopropylmethylamino)-9H-purin-9-yl)-4-fluoro-3,4-dimethyltetrahydrofuran-2-yl)methyl benzoate,
((2R,3S,4R,5S)-3-acetoxy-5-(6-(cyclopropylmethylamino)-9H-purin-9-yl)-4-fluoro-3,4-dimethyltetrahydrofuran-2-yl)methyl benzoate,
((2R,3R,4R,5R)-3-acetoxy-5-(2-amino-6-chloro-9H-purin-9-yl)-4-fluoro-3,4-dimethyltetrahydrofuran-2-yl)methyl benzoate,
((2R,3R,4R,5S)-3-acetoxy-5-(2-amino-6-chloro-9H-purin-9-yl)-4-fluoro-3,4-dimethyltetrahydrofuran-2-yl)methyl benzoate,
((2R,3S,4R,5R)-3-acetoxy-5-(2-amino-6-chloro-9H-purin-9-yl)-4-fluoro-3,4-dimethyltetrahydrofuran-2-yl)methyl benzoate,
((2R,3S,4R,5S)-3-acetoxy-5-(2-amino-6-chloro-9H-purin-9-yl)-4-fluoro-3,4-dimethyltetrahydrofuran-2-yl)methyl benzoate,
(2R,3R,4R,5R)-5-(6-(cyclopentylamino)-9H-purin-9-yl)-4-fluoro-2-(hydroxymethyl)-3,4-dimethyltetrahydrofuran-3-ol,
(2R,3R,4R,5S)-5-(6-(cyclopentylamino)-9H-purin-9-yl)-4-fluoro-2-(hydroxymethyl)-3,4-dimethyltetrahydrofuran-3-ol,
(2R,3S,4R,5R)-5-(6-(cyclopentylamino)-9H-purin-9-yl)-4-fluoro-2-(hydroxymethyl)-3,4-dimethyltetrahydrofuran-3-ol,
(2R,3S,4R,5S)-5-(6-(cyclopentylamino)-9H-purin-9-yl)-4-fluoro-2-(hydroxymethyl)-3,4-dimethyltetrahydrofuran-3-ol,
(2R,3R,4R,5R)-5-(6-(cyclohexylamino)-9H-purin-9-yl)-4-fluoro-2-(hydroxymethyl)-3,4-dimethyltetrahydrofuran-3-ol,
(2R,3R,4R,5S)-5-(6-(cyclohexylamino)-9H-purin-9-yl)-4-fluoro-2-(hydroxymethyl)-3,4-dimethyltetrahydrofuran-3-ol,
(2R,3S,4R,5R)-5-(6-(cyclohexylamino)-9H-purin-9-yl)-4-fluoro-2-(hydroxymethyl)-3,4-dimethyltetrahydrofuran-3-ol,
(2R,3S,4R,5S)-5-(6-(cyclohexylamino)-9H-purin-9-yl)-4-fluoro-2-(hydroxymethyl)-3,4-dimethyltetrahydrofuran-3-ol,
((2R,3R,4R,5R)-3-acetoxy-5-(6-(benzylamino)-9H-purin-9-yl)-4-fluoro-3,4-dimethyltetrahydrofuran-2-yl)methyl benzoate,
((2R,3R,4R,5S)-3-acetoxy-5-(6-(benzylamino)-9H-purin-9-yl)-4-fluoro-3,4-dimethyltetrahydrofuran-2-yl)methyl benzoate,
((2R,3S,4R,5R)-3-acetoxy-5-(6-(benzylamino)-9H-purin-9-yl)-4-fluoro-3,4-dimethyltetrahydrofuran-2-yl)methyl benzoate,
((2R,3S,4R,5S)-3-acetoxy-5-(6-(benzylamino)-9H-purin-9-yl)-4-fluoro-3,4-dimethyltetrahydrofuran-2-yl)methyl benzoate,
(2R,3R,4R,5R)-5-(6-(cyclopropylmethylamino)-9H-purin-9-yl)-4-fluoro-2-(hydroxymethyl)-3,4-dimethyltetrahydrofuran-3-ol,
(2R,3R,4R,5S)-5-(6-(cyclopropylmethylamino)-9H-purin-9-yl)-4-fluoro-2-(hydroxymethyl)-3,4-dimethyltetrahydrofuran-3-ol,
(2R,3S,4R,5R)-5-(6-(cyclopropylmethylamino)-9H-purin-9-yl)-4-fluoro-2-(hydroxymethyl)-3,4-dimethyltetrahydrofuran-3-ol,
(2R,3S,4R,5S)-5-(6-(cyclopropylmethylamino)-9H-purin-9-yl)-4-fluoro-2-(hydroxymethyl)-3,4-dimethyltetrahydrofuran-3-ol,
((2R,3R,4R,5R)-5-(2,4-dioxo-3,4-dihydropyrimidin-1(2H)-yl)-4-fluoro-3-hydroxy-3,4-dimethyltetrahydrofuran-2-yl)methyl butyrate,
((2R,3R,4R,5S)-5-(2,4-dioxo-3,4-dihydropyrimidin-1(2H)-yl)-4-fluoro-3-hydroxy-3,4-dimethyltetrahydrofuran-2-yl)methyl butyrate,
((2R,3S,4R,5R)-5-(2,4-dioxo-3,4-dihydropyrimidin-1(2H)-yl)-4-fluoro-3-hydroxy-3,4-dimethyltetrahydrofuran-2-yl)methyl butyrate,
((2R,3S,4R,5S)-5-(2,4-dioxo-3,4-dihydropyrimidin-1(2H)-yl)-4-fluoro-3-hydroxy-3,4-dimethyltetrahydrofuran-2-yl)methyl butyrate,
((2R,3R,4R,5R)-5-(2,4-dioxo-3,4-dihydropyrimidin-1(2H)-yl)-4-fluoro-3-hydroxy-3,4-dimethyltetrahydrofuran-2-yl)methyl pentanoate,
((2R,3R,4R,5S)-5-(2,4-dioxo-3,4-dihydropyrimidin-1(2H)-yl)-4-fluoro-3-hydroxy-3,4-dimethyltetrahydrofuran-2-yl)methyl pentanoate,
((2R,3S,4R,5R)-5-(2,4-dioxo-3,4-dihydropyrimidin-1(2H)-yl)-4-fluoro-3-hydroxy-3,4-dimethyltetrahydrofuran-2-yl)methyl pentanoate,
((2R,3S,4R,5S)-5-(2,4-dioxo-3,4-dihydropyrimidin-1(2H)-yl)-4-fluoro-3-hydroxy-3,4-dimethyltetrahydrofuran-2-yl)methyl pentanoate,
((2R,3R,4R,5R)-3-acetoxy-4-fluoro-3,4-dimethyl-5-(6-oxo-1H-purin-9(6H)-yl)tetrahydrofuran-2-yl)methyl benzoate,
((2R,3R,4R,5S)-3-acetoxy-4-fluoro-3,4-dimethyl-5-(6-oxo-1H-purin-9(6H)-yl)tetrahydrofuran-2-yl)methyl benzoate,
((2R,3S,4R,5R)-3-acetoxy-4-fluoro-3,4-dimethyl-5-(6-oxo-1H-purin-9(6H)-yl)tetrahydrofuran-2-yl)methyl benzoate,
((2R,3S,4R,5S)-3-acetoxy-4-fluoro-3,4-dimethyl-5-(6-oxo-1H-purin-9(6H)-yl)tetrahydrofuran-2-yl)methyl benzoate, 9-((2R,3R,4R,5R)-3-fluoro-4-hydroxy-5-(hydroxymethyl)-3,4-dimethyltetrahydrofuran-2-yl)-1 H-purin-6 (9H)-one, 9-((2R,3R,4S,5R)-3-fluoro-4-hydroxy-5-(hydroxymethyl)-3,4-dimethyltetrahydrofuran-2-yl)-1 H-purin-6 (9H)-one, 9-((2S,3R,4R,5R)-3-fluoro-4-hydroxy-5-(hydroxymethyl)-3,4-dimethyltetrahydrofuran-2-yl)-1 H-purin-6 (9H)-one, 9-((2S,3R,4S,5R)-3-fluoro-4-hydroxy-5-(hydroxymethyl)-3,4-dimethyltetrahydrofuran-2-yl)-1 H-purin-6 (9H)-one, ((2R,3R,4R,5R)-3-acetoxy-4-fluoro-3,4-dimethyl-5-(5-methyl-2,4-dioxo-3,4-dihydropyrimidin-1(2H)-yl)tetrahydrofuran-2-yl)methyl benzoate, ((2R,3R,4R,5S)-3-acetoxy-4-fluoro-3,4-dimethyl-5-(5-methyl-2,4-dioxo-3,4-dihydropyrimidin-1(2H)-yl)tetrahydrofuran-2-yl)methyl benzoate, ((2R,3S,4R,5R)-3-acetoxy-4-fluoro-3,4-dimethyl-5-(5-methyl-2,4-dioxo-3,4-dihydropyrimidin-1(2H)-yl)tetrahydrofuran-2-yl)methyl benzoate, ((2R,3S,4R,5S)-3-acetoxy-4-fluoro-3,4-dimethyl-5-(5-methyl-2,4-dioxo-3,4-dihydropyrimidin-1(2H)-yl)tetrahydrofuran-2-yl)methyl benzoate, ((2R,3R,4R,5R)-5-(2,4-dioxo-3,4-dihydropyrimidin-1(2H)-yl)-4-fluoro-3-hydroxy-3,4-dimethyltetrahydrofuran-2-yl)methyl isobutyrate, ((2R,3R,4R,5S)-5-(2,4-dioxo-3,4-dihydropyrimidin-1(2H)-yl)-4-fluoro-3-hydroxy-3,4-dimethyltetrahydrofuran-2-yl)methyl isobutyrate, ((2R,3S,4R,5R)-5-(2,4-dioxo-3,4-dihydropyrimidin-1(2H)-yl)-4-fluoro-3-hydroxy-3,4-dimethyltetrahydrofuran-2-yl)methyl isobutyrate, ((2R,3S,4R,5S)-5-(2,4-dioxo-3,4-dihydropyrimidin-1(2H)-yl)-4-fluoro-3-hydroxy-3,4-dimethyltetrahydrofuran-2-yl)methyl isobutyrate, (2R,3R,4R,5R)-4-fluoro-2-(hydroxymethyl)-3,4-dimethyl-5-(6-morpholino-9H-purin-9-yl)tetrahydrofuran-3-ol, (2R,3R,4R,5S)-4-fluoro-2-(hydroxymethyl)-3,4-dimethyl-5-(6-morpholino-9H-purin-9-yl)tetrahydrofuran-3-ol, (2R,3S,4R,5R)-4-fluoro-2-(hydroxymethyl)-3,4-dimethyl-5-(6-morpholino-9H-purin-9-yl)tetrahydrofuran-3-ol, (2R,3S,4R,5S)-4-fluoro-2-(hydroxymethyl)-3,4-dimethyl-5-(6-morpholino-9H-purin-9-yl)tetrahydrofuran-3-ol, ((2R,3R,4R,5R)-3-acetoxy-4-fluoro-5-(5-fluoro-2,4-dioxo-3,4-dihydropyrimidin-1(2H)-yl)-3,4-dimethyltetrahydrofuran-2-yl)methyl benzoate, ((2R,3R,4R,5S)-3-acetoxy-4-fluoro-5-(5-fluoro-2,4-dioxo-3,4-dihydropyrimidin-1(2H)-yl)-3,4-dimethyltetrahydrofuran-2-yl)methyl benzoate, ((2R,3S,4R,5R)-3-acetoxy-4-fluoro-5-(5-fluoro-2,4-dioxo-3,4-dihydropyrimidin-1(2H)-yl)-3,4-dimethyltetrahydrofuran-2-yl)methyl benzoate, ((2R,3S,4R,5S)-3-acetoxy-4-fluoro-5-(5-fluoro-2,4-dioxo-3,4-dihydropyrimidin-1(2H)-yl)-3,4-dimethyltetrahydrofuran-2-yl)methyl benzoate, 5-fluoro-1-((2R,3R,4R,5R)-3-fluoro-4-hydroxy-5-(hydroxymethyl)-3,4-dimethyltetrahydrofuran-2-yl)pyrimidine-2,4(1H,3H)-dione, 5-fluoro-1-((2R,3R,4S,5R)-3-fluoro-4-hydroxy-5-(hydroxymethyl)-3,4-dimethyltetrahydrofuran-2-yl)pyrimidine-2,4(1H,3H)-dione, 5-fluoro-1-((2S,3R,4R,5R)-3-fluoro-4-hydroxy-5-(hydroxymethyl)-3,4-dimethyltetrahydrofuran-2-yl)pyrimidine-2,4(1H,3H)-dione, 5-fluoro-1-((2S,3R,4S,5R)-3-fluoro-4-hydroxy-5-(hydroxymethyl)-3,4-dimethyltetrahydrofuran-2-yl)pyrimidine-2,4(1H,3H)-dione, ((2R,3R,4R,5R)-4-fluoro-3-hydroxy-3,4-dimethyl-5-(6-morpholino-9H-purin-9-yl)tetrahydrofuran-2-yl)methyl pentanoate, ((2R,3R,4R,5S)-4-fluoro-3-hydroxy-3,4-dimethyl-5-(6-morpholino-9H-purin-9-yl)tetrahydrofuran-2-yl)methyl pentanoate, ((2R,3S,4R,5R)-4-fluoro-3-hydroxy-3,4-dimethyl-5-(6-morpholino-9H-purin-9-yl)tetrahydrofuran-2-yl)methyl pentanoate, ((2R,3S,4R,5S)-4-fluoro-3-hydroxy-3,4-dimethyl-5-(6-morpholino-9H-purin-9-yl)tetrahydrofuran-2-yl)methyl pentanoate, ((2R,3R,4R,5R)-4-fluoro-3-hydroxy-3,4-dimethyl-5-(6-morpholino-9H-purin-9-yl)tetrahydrofuran-2-yl)methyl butyrate, ((2R,3R,4R,5S)-4-fluoro-3-hydroxy-3,4-dimethyl-5-(6-morpholino-9H-purin-9-yl)tetrahydrofuran-2-yl)methyl butyrate, ((2R,3S,4R,5R)-4-fluoro-3-hydroxy-3,4-dimethyl-5-(6-morpholino-9H-purin-9-yl)tetrahydrofuran-2-yl)methyl butyrate, ((2R,3S,4R,5S)-4-fluoro-3-hydroxy-3,4-dimethyl-5-(6-morpholino-9H-purin-9-yl)tetrahydrofuran-2-yl)methyl butyrate, ((2R,3R,4R,5R)-4-fluoro-3-hydroxy-3,4-dimethyl-5-(6-morpholino-9H-purin-9-yl)tetrahydrofuran-2-yl) methylisobutyrate, ((2R,3R,4R,5S)-4-fluoro-3-hydroxy-3,4-dimethyl-5-(6-morpholino-9H-purin-9-yl)tetrahydrofuran-2-yl)methyl isobutyrate, ((2R,3S,4R,5R)-4-fluoro-3-hydroxy-3,4-dimethyl-5-(6-morpholino-9H-purin-9-yl)tetrahydrofuran-2-yl)methyl isobutyrate, ((2R,3S,4R,5S)-4-fluoro-3-hydroxy-3,4-dimethyl-5-(6-morpholino-9H-purin-9-yl)tetrahydrofuran-2-yl)methyl isobutyrate, (2R,3R,4R,5R)-5-(6-(3-chlorobenzylamino)-9H-purin-9-yl)-4-fluoro-2-(hydroxymethyl)-3,4-dimethyltetrahydrofuran-3-ol, (2R,3R,4R,5S)-5-(6-(3-chlorobenzylamino)-9H-purin-9-yl)-4-fluoro-2-(hydroxymethyl)-3,4-dimethyltetrahydrofuran-3-ol, (2R,3S,4R,5R)-5-(6-(3-chlorobenzylamino)-9H-purin-9-yl)-4-fluoro-2-(hydroxymethyl)-3,4-dimethyltetrahydrofuran-3-ol, (2R,3S,4R,5S)-5-(6-(3-chlorobenzylamino)-9H-purin-9-yl)-4-fluoro-2-(hydroxymethyl)-3,4-dimethyltetrahydrofuran-3-ol, (2R,3R,4R,5R)-4-fluoro-5-(6-(furan-2-ylmethylamino)-9H-purin-9-yl)-2-(hydroxymethyl)-3,4-dimethyltetrahydrofuran-3-ol, (2R,3R,4R,5S)-4-fluoro-5-(6-(furan-2-ylmethylamino)-9H-purin-9-yl)-2-(hydroxymethyl)-3,4-dimethyltetrahydrofuran-3-ol, (2R,3S,4R,5R)-4-fluoro-5-(6-(furan-2-ylmethylamino)-9H-purin-9-yl)-2-(hydroxymethyl)-3,4-dimethyltetrahydrofuran-3-ol, (2R,3S,4R,5S)-4-fluoro-5-(6-(furan-2-ylmethylamino)-9H-purin-9-yl)-2-(hydroxymethyl)-3,4-dimethyltetrahydrofuran-3-ol, (2R,3R,4R,5R)-5-(6-(2-chlorobenzylamino)-9H-purin-9-yl)-4-fluoro-2-(hydroxymethyl)-3,4-dimethyltetrahydrofuran-3-ol, (2R,3R,4R,5S)-5-(6-(2-chlorobenzylamino)-9H-purin-9-yl)-4-fluoro-2-(hydroxymethyl)-3,4-dimethyltetrahydrofuran-3-ol, (2R,3S,4R,5R)-5-(6-(2-chlorobenzylamino)-9H-purin-9-yl)-4-fluoro-2-(hydroxymethyl)-3,4-dimethyltetrahydrofuran-3-ol,
(2R,3S,4R,5S)-5-(6-(2-chlorobenzylamino)-9H-purin-9-yl)-4-fluoro-2-(hydroxymethyl)-3,4-dimethyltetrahydrofuran-3-ol,
(2R,3R,4R,5R)-5-(6-(cyclobutylamino)-9H-purin-9-yl)-4-fluoro-2-(hydroxymethyl)-3,4-dimethyltetrahydrofuran-3-ol,
(2R,3R,4R,5S)-5-(6-(cyclobutylamino)-9H-purin-9-yl)-4-fluoro-2-(hydroxymethyl)-3,4-dimethyltetrahydrofuran-3-ol,
(2R,3S,4R,5R)-5-(6-(cyclobutylamino)-9H-purin-9-yl)-4-fluoro-2-(hydroxymethyl)-3,4-dimethyltetrahydrofuran-3-ol,
(2R,3S,4R,5S)-5-(6-(cyclobutylamino)-9H-purin-9-yl)-4-fluoro-2-(hydroxymethyl)-3,4-dimethyltetrahydrofuran-3-ol,
(2S)-((2R,3R,4R,5R)-4-fluoro-3-hydroxy-3,4-dimethyl-5-(5-methyl-2,4-dioxo-3,4-dihydropyrimidin-1(2H)-yl) tetrahydrofuran-2-yl)methyl 2-(tert-butoxycarbonylamino)propanoate,
(2S)-((2R,3R,4R,5S)-4-fluoro-3-hydroxy-3,4-dimethyl-5-(5-methyl-2,4-dioxo-3,4-dihydropyrimidin-1(2H)-yl) tetrahydrofuran-2-yl)methyl 2-(tert-butoxycarbonylamino)propanoate,
(2S)-((2R,3S,4R,5R)-4-fluoro-3-hydroxy-3,4-dimethyl-5-(5-methyl-2,4-dioxo-3,4-dihydropyrimidin-1(2H)-yl) tetrahydrofuran-2-yl)methyl 2-(tert-butoxycarbonylamino)propanoate,
(2S)-((2R,3S,4R,5S)-4-fluoro-3-hydroxy-3,4-dimethyl-5-(5-methyl-2,4-dioxo-3,4-dihydropyrimidin-1(2H)-yl) tetrahydrofuran-2-yl)methyl 2-(tert-butoxycarbonylamino)propanoate,
((2R,3R,4R,5R)-4-fluoro-3-hydroxy-3,4-dimethyl-5-(5-methyl-2,4-dioxo-3,4-dihydropyrimidin-1(2H)-yl)tetrahydrofuran-2-yl) methyl 2aminopropanoate,
((2R,3R,4R,5S)-4-fluoro-3-hydroxy-3,4-dimethyl-5-(5-methyl-2,4-dioxo-3,4-dihydropyrimidin-1(2H)-yl)tetrahydrofuran-2-yl) methyl 2-aminopropanoate,
((2R,3S,4R,5R)-4-fluoro-3-hydroxy-3,4-dimethyl-5-(5-methyl-2,4-dioxo-3,4-dihydropyrimidin-1(2H)-yl)tetrahydrofuran-2-yl) methyl 2-aminopropanoate,
((2R,3S,4R,5S)-4-fluoro-3-hydroxy-3,4-dimethyl-5-(5-methyl-2,4-dioxo-3,4-dihydropyrimidin-1(2H)-yl)tetrahydrofuran-2-yl) methyl 2-aminopropanoate,
and pharmceutically acceptable salts thereof.

9. A compound of the formula (II):

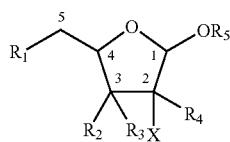

II wherein,
$R_5$ is alkyl, hydrogen, acyl, aryl, alkyl carbonyloxy, aryl carbonyloxy, silyl, sulfonyl, or $OR_5$ together represent as halogen;
X is halogen;
$R_4$ is alkyl group;
$R_2$ and $R_3$ independently are selected from OH, alkyl, alkenyl, halogen, alkynyl, cycloalkyl, $N_3$, $CF_3$, $NH_2$, or CN;
$R_2$ and $R_3$ can be together form oxo (=O) group;

R1 is H, OH, -{P(O)(OH)O-}nR, alkyl, hydrogen, acyl, benzoyl, aryl, alkyl carbonyloxy, aryl carbonyloxy, silyl, heterocycloalkyl, sulfonyl, RCONHCH(Ra)C(O)O, or $NH_2CH(R^a)C(O)O$ wherein $R^a$ is H, alkyl, or benezyl;
R is alkyl, hydrogen, acyl, aryl, alkyl carbonyloxy, aryl carbonyloxy, or heterocycloalkyl;
$R_1$, $R_2$, $R_3$, $R_4$, $R_5$ and R are independently further substituted wherever appropriate from the group consisting of halogen, alkyl, alkenyl, alkynyl, aryl, alkylaryl, aralkyl, cycloalkyl, heterocyclyl, heterocycloakyl, hydroxy, amino, cyano, azido, carbonyl, oxycarbonyl, sulfonyl, sulfonyloxy, or carbonyloxy, an analog thereof, a pharmaceutically acceptable salt thereof, a pharmaceutically acceptable solvate thereof, a pharmaceutically acceptable hydrate thereof, an N-oxide thereof, a tautomer thereof, a regioisomer thereof, a stereoisomer thereof, a prodrug thereof or a polymorph thereof.

10. A method of treating bacterial infection in a subject in need thereof comprising administering to the subject a therapeutically effective amount of a compound according to any one of claims 2, 3, 6, 7, 8, or 9.

11. A compound according to any one of claims 2, 3, 6, 7, 8, or 9 wherein the salt is (a) an inorganic acid addition salt selected from hydrochloride, sulphate, phosphate and nitrate, or (b) an organic acid addition salt selected from acetate, oxalate, maleate, tartarate, citrate, mesylate, succinate, and cinnamate.

12. A pharmaceutical composition comprising a compound according to any one of claims 2, 3, 6, 7, 8, or 9 and a pharmaceutically acceptable excipient.

13. The pharmaceutical composition according to claim 12, wherein the pharmaceutically acceptable excipient is a carrier or diluent.

14. A method for ameliorating or treating a viral mediated disease, disorder or syndrome in a subject in need thereof comprising administering to the subject a therapeutically effective amount of a compound according to any one of claims 2, 3, 6, 7, 8, or 9.

15. The method according to claim 14, wherein the viral mediated disease, disorder or syndrome is selected from the group consisting of HIV infection, HBV, HCV, a retroviral infection genetically related to AIDS, respiratory disorders, adult respiratory distress syndrome (ARDS), and inflammatory disease.

16. The method according to claim 14, wherein the disease, disorder or syndrome is selected from the group consisting of HIV infection, HBV, HCV, a retroviral infection genetically related to 11W, AIDS, inflammatory disease, respiratory disorders, adult respiratory distress syndrome (ARDS), bronchitis, chronic bronchitis, chronic obstructive pulmonary disease, cystic fibrosis, asthma, emphysema, rhinitis and chronic sinusitis, inflammatory bowel disease, Crohn's disease and ulcerative colitis, multiple sclerosis, rheumatoid arthritis, graft rejection, endometriosis, type I diabetes, renal diseases, chronic pancreatitis, inflammatory lung conditions, chronic heart failure and bacterial infections.

17. A method of treating HCV in a subject in need thereof comprising administering to the subject a therapeutically effective amount of a compound according to any one of claims 2, 3, 6, 7, 8, or 9.

18. A method of treating HBV in a subject in need thereof comprising administering to the subject a therapeutically effective amount of a compound according to any one of claims 2, 3, 6, 7, 8, or 9.

* * * * *